US011712182B2

(12) United States Patent
Parker et al.

(10) Patent No.: US 11,712,182 B2
(45) Date of Patent: Aug. 1, 2023

(54) MULTI-STATE ENGAGEMENT WITH CONTINUOUS GLUCOSE MONITORING SYSTEMS

(71) Applicant: DexCom, Inc., San Diego, CA (US)

(72) Inventors: Andrew Scott Parker, San Diego, CA (US); Annika Emilie Kristina Jimenez, Carlsbad, CA (US); Chad Patterson, San Diego, CA (US); Subrai Girish Pai, San Diego, CA (US); Apurv Ullas Kamath, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 196 days.

(21) Appl. No.: 17/114,204

(22) Filed: Dec. 7, 2020

(65) Prior Publication Data

US 2021/0177317 A1    Jun. 17, 2021

Related U.S. Application Data

(60) Provisional application No. 62/948,724, filed on Dec. 16, 2019.

(51) Int. Cl.
*A61B 5/145* (2006.01)
*G06N 3/08* (2023.01)
(Continued)

(52) U.S. Cl.
CPC ........ *A61B 5/14532* (2013.01); *A61B 5/0004* (2013.01); *A61B 5/0022* (2013.01);
(Continued)

(58) Field of Classification Search
CPC . A61B 5/14532; A61B 5/0004; A61B 5/0022; G06N 3/08
See application file for complete search history.

(56) References Cited

U.S. PATENT DOCUMENTS

2016/0210427 A1    7/2016 Mynhier et al.
2017/0220750 A1*   8/2017 Davis .................... G06N 20/00
(Continued)

FOREIGN PATENT DOCUMENTS

CN         202393731 U      8/2012

OTHER PUBLICATIONS

International Search Report and Written Opinion dated Mar. 8, 2021 for Application No. PCT/US2020/063655, filed Dec. 7, 2020; 9 pages.
(Continued)

*Primary Examiner* — Navin Natnithithadha
*Assistant Examiner* — Meghan R Kumar
(74) *Attorney, Agent, or Firm* — Patterson + Sheridan, LLP

(57) ABSTRACT

Multi-state engagement with continuous glucose monitoring (CGM) systems is described. Given the number of people that wear CGM systems and because CGM systems produce measurements continuously, a platform that provides a CGM system may have an enormous amount of data. This amount of data is practically, if not actually, impossible for humans to process. In implementations, a CGM platform includes a data analytics platform that obtains packages of glucose measurements provided by a CGM system and also obtains additional data associated with a user. The data analytics platform generates state information for the user by processing these CGM packages and the additional data, at least in part, by using one or more models. Based on this state information, the data analytics platform controls communication with the user, which may include generating intervention strategies to prevent users from transitioning to a negative state such as discontinuing use of the CGM system.

24 Claims, 22 Drawing Sheets

(51) Int. Cl.
| | |
|---|---|
| A61B 5/00 | (2006.01) |
| G16H 40/67 | (2018.01) |
| G16H 50/50 | (2018.01) |
| G16H 10/60 | (2018.01) |
| G16H 50/30 | (2018.01) |
| G16H 50/70 | (2018.01) |
| G16H 50/20 | (2018.01) |
| A61B 5/16 | (2006.01) |
| G06Q 30/0201 | (2023.01) |

(52) U.S. Cl.
CPC ............ *A61B 5/167* (2013.01); *A61B 5/4833* (2013.01); *A61B 5/4842* (2013.01); *A61B 5/7264* (2013.01); *A61B 5/7275* (2013.01); *A61B 5/742* (2013.01); *A61B 5/7475* (2013.01); *G06N 3/08* (2013.01); *G06Q 30/0201* (2013.01); *G16H 10/60* (2018.01); *G16H 40/67* (2018.01); *G16H 50/20* (2018.01); *G16H 50/30* (2018.01); *G16H 50/50* (2018.01); *G16H 50/70* (2018.01)

(56) References Cited

U.S. PATENT DOCUMENTS

| | | |
|---|---|---|
| 2018/0353698 A1 | 12/2018 | Saint et al. |
| 2019/0252079 A1 | 8/2019 | Constantin et al. |
| 2019/0262536 A1 | 8/2019 | O'Connell et al. |
| 2020/0085300 A1 | 3/2020 | Kwatra et al. |
| 2021/0177316 A1 | 6/2021 | Parker et al. |
| 2021/0183508 A1 | 6/2021 | Parker et al. |

OTHER PUBLICATIONS

Luo Y., "Machine Learning of Lifestyle Data for Diabetes," Electronic Thesis and Dissertation Repository, 2016, 110 pages.

* cited by examiner

2000 ⟶

2002
Maintain at least continuous glucose monitoring (CGM) packages and additional data of a user population of users of the CGM system

2004
Generate state information for users of the user population by processing at least a portion of the CGM packages and the additional data using one or more models, the state information including transition probabilities that respective users of the user population will transition from a current state to a negative state and driving factors that are likely to drive the transition

2006
Identify users of the user population that are likely to transition to the negative state based on the transition probabilities

2008
Generate intervention strategies to prevent the users from transitioning to the negative state based on the transition probabilities and the driving factors

Fig. 20

MULTI-STATE ENGAGEMENT WITH CONTINUOUS GLUCOSE MONITORING SYSTEMS

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Patent Application No. 62/948,724, filed Dec. 16, 2019, and titled "Recommendations Based on Continuous Glucose Monitoring". The aforementioned application is incorporated by reference herein in its entirety, and is hereby expressly made a part of this specification.

BACKGROUND

Diabetes is a metabolic condition affecting hundreds of millions of people, and is one of the leading causes of death worldwide. For people living with diabetes, access to treatment is critical to their survival. With proper treatment, serious damage to the heart, blood vessels, eyes, kidneys, and nerves, due to diabetes can be largely avoided. Proper treatment for a person with Type I diabetes oftentimes involves monitoring glucose levels throughout the day and regulating those levels—with some combination of insulin, eating, and exercise—so that the levels stay within a desired range.

One of the challenges of developing a treatment plan for a person with diabetes is that different people who have diabetes may be affected differently by various factors, such as the foods they eat and stress. There may be a wide variance, for example, in how glucose levels of different people are affected when those people eat the same meal. Stress can also affect people differently, by elevating their hormone levels differently which impacts control of their glucose. Accordingly, a treatment plan that works for one person with diabetes may not work for another. Medical professionals and people with diabetes may thus work through iterations of treatment plans, adjusting various aspects of those plans as responses to treatment are observed. Regulating glucose levels therefore often involves a degree of customization. Common to treatment plans, though, is monitoring glucose levels. With advances in medical technologies a variety of systems for monitoring glucose levels have been developed.

Some of these systems include assemblies for pricking a body part of a person (e.g., the person's finger in many cases) to draw blood and also sensors for detecting analytes in the drawn blood indicative of a glucose level. Other systems detect analytes indicative of glucose levels with sensors in substantially real-time and produce measurements of those glucose levels over a period of time—referred to as continuous glucose monitoring (CGM). Both types of systems are configured to output (e.g., display) these measurements so that users and medical professionals can decide how best to regulate the users' glucose levels. The sheer volume of glucose measurements produced and output by CGM systems shows users how their glucose levels have been trending and enables them to make better informed decisions regarding treatment.

SUMMARY

Multi-state engagement with continuous glucose monitoring (CGM) systems is described herein. Given the number of people that wear CGM systems and because CGM systems produce measurements continuously, a CGM platform that provides a CGM system with a sensor for detecting glucose levels, and maintains data describing the detection of those glucose levels may have an enormous amount of data, e.g., tens of millions of patient days' worth of data points. However, this amount of data is practically, if not actually, impossible for a human to process to reliably identify patterns not only in data packages that include the glucose measurements but also in connection with a wealth of additional data, which can be correlated with the packages to accurately predict states of engagement with the CGM system, e.g., whether a user will discontinue use of the CGM system.

In one or more implementations, a CGM platform includes a data analytics platform that obtains packages of glucose measurements provided by a CGM system worn by a user. The data analytics platform also obtains additional data associated with the user. However, the data analytics platform obtains the additional data from one or more sources different from the CGM system, such as from a user profile that maintains a purchase history of the user describing purchases of the CGM system or its components (e.g. a sensor application assembly), purchases of services from the CGM platform, pharmaceutical purchases, and so on. The additional data may also include physiological data additional to the glucose measurements, socioeconomic data, attitudinal data, behavioral data, and complaint data, to name just a few.

The data analytics platform generates state information for the user by processing these CGM packages and the additional data, at least in part, by using one or more models, e.g., unsupervised learning models, supervised learning models, reinforcement learning models, and so on. This state information may indicate a current state of the user's engagement with the CGM system and the CGM platform or predict a transition to a different, new state. The data analytics platform generates these models based on historical CGM packages and historical additional data of a user population, e.g., a plurality of users that also wear or have worn the CGM system. Based on this state information, the data analytics platform controls communication with the user, which may include generating intervention strategies to prevent users from transitioning to a negative state such as discontinuing use of the CGM system.

This Summary introduces a selection of concepts in a simplified form that are further described below in the Detailed Description. As such, this Summary is not intended to identify essential features of the claimed subject matter, nor is it intended to be used as an aid in determining the scope of the claimed subject matter.

BRIEF DESCRIPTION OF THE DRAWINGS

The detailed description is described with reference to the accompanying figures.

FIG. 20 depicts a procedure in an example implementation in which intervention strategies are generated to prevent users from transitioning to a negative state.

DETAILED DESCRIPTION

Overview

Figure 1:
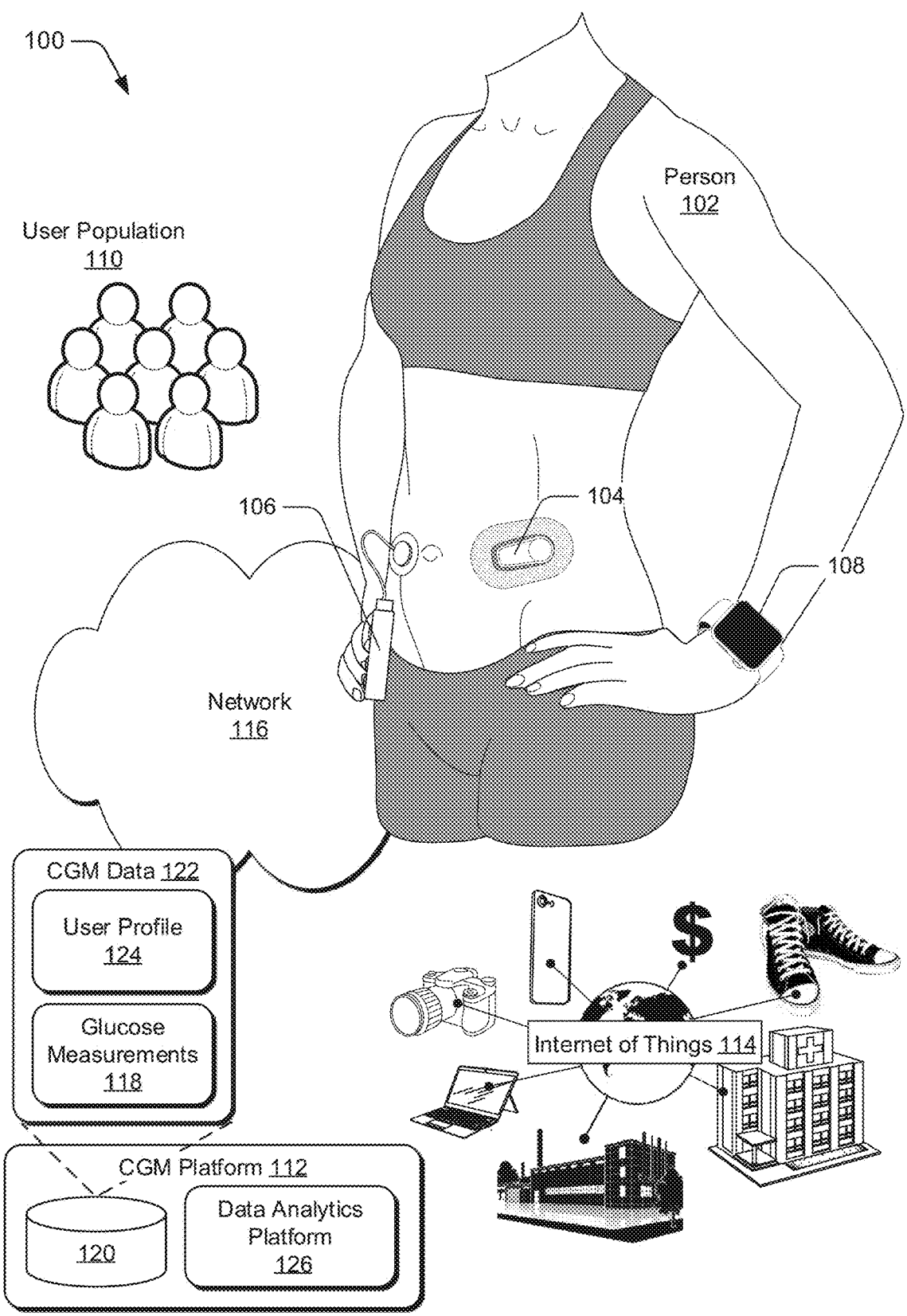
FIG. 1 is an illustration of an environment in an example implementation that is operable to employ techniques described herein.

Multi-state engagement with continuous glucose monitoring (CGM) systems is described herein. Given the number of people that wear CGM systems and because CGM systems produce measurements continuously, a CGM platform that provides a CGM system with a sensor for detecting glucose levels, and maintains data describing the detection of those glucose levels may have an enormous amount of data, e.g., tens of millions of patient days' worth of data points. However, this amount of data is practically, if not actually, impossible for a human to process to reliably identify patterns not only in data packages that include the glucose measurements but also in connection with a wealth of additional data, which can be correlated with the packages to accurately predict states of engagement with the CGM system, e.g., whether a user will discontinue use of the CGM system.

To overcome these problems, multi-state engagement with CGM systems is leveraged. In one or more implementations, a CGM platform obtains glucose measurements from various CGM systems and computing devices of users in a user population. In accordance with the described techniques, a CGM system is configured to monitor blood glucose of a person continuously. The CGM system may be configured with a CGM sensor, for instance, that is inserted subcutaneously into skin of a person and detects analytes indicative of the person's blood glucose. The CGM system can generate glucose measurements based on the detected analytes continuously. As used herein, the term "continuously" means near-continuously, such that continuous glucose monitoring produces measurements at intervals of time that are supported by resources of a CGM system (e.g., battery life, processing capabilities, communication capabilities, etc.) and without requiring manual interaction of a user such as finger pricks. By monitoring glucose levels continuously, the CGM system not only allows users to make better informed decisions about their treatment but also continues to monitor glucose levels while allowing them to participate in activities where manually pricking a finger could be dangerous, e.g., driving a car.

The CGM system transmits glucose measurements to a computing device that is communicatively coupled to the CGM system, such as a smart watch worn by the person, the person's smartphone, or a dedicated device associated with the CGM system. The CGM system may communicate the glucose measurements in real-time, at set time intervals, or responsive to a request from the computing device. The computing device then provides the glucose measurements to the CGM platform, such as by communicating the glucose measurements over a network to a cloud-based service that hosts the CGM platform.

The CGM platform may also obtain additional data of users in the user population which originate from various devices, sensors, applications, or services. The additional data may include, by way of example and not limitation, health-related data, application interaction data, environmental data, demographic data, device data in addition to the glucose measurements (e.g., sensor identification data, incident reports), supplemental data added by the computing device, third party data, and so forth. Health-related data may include activity data (e.g., steps, exercise frequency, sleep data), biometric data (e.g., insulin level, ketone levels, heart rate, temperature, stress), nutrition data (e.g., food and drink logs, scanned restaurant receipts, carbohydrate consumption, fasting), medical records (e.g., A1C, cholesterol, electrocardiogram results, and data related to other medical tests or history), to name just a few. Application interaction data may include data extracted from application logs describing user interactions with particular applications, clickstream data describing clicks, taps, and presses performed in relation to input/output interfaces of the computing device, gaze data describing where a user is looking (e.g., in relation to a display device associated with the computing device or when the user is looking away from the device), voice data describing audible commands and other spoken phrases of the user or other users (e.g., including passively listening to users), and so forth. Environmental data may include data describing various environmental aspects associated with the user, such as the user's location, a temperature and/or weather at the user's location, altitude of the user, barometric pressure, and so forth. Demographic data may include data describing the user, such as age, sex, height, weight, and so forth. The above-discussed types of additional data are merely examples and the additional data may include more, fewer, or different types of data without departing from the spirit or scope of the techniques described herein.

The CGM platform stores and aggregates glucose measurements and additional data collected from the various respective users of the user population. In some cases, the glucose measurements and the additional data may be time stamped which enables the glucose measurements and additional data of a respective user to be stored in a way which maintains a time-based relationship, or sequence, between the various pieces of data. This allows the CGM platform to make a variety of different predictions and inferences based on distinct data sets which have simply not been analyzed together at such a massive scale by conventional systems.

In order to generate predictions and inferences using the aggregated data, the CGM platform leverages the wealth of aggregated data maintained by the CGM platform to build various models, such as a statistical model, a machine learning model configured as a neural network, and/or other machine learning model. For instance, the system can build statistical models, build other machine learning models, train the other machine learning models (or otherwise learn a policy deployed by such machine learning models), and update these models using the glucose measurements and the additional data of the user population.

Notably, unlike conventional systems, the CGM platform may have access to glucose measurements obtained using the CGM system for hundreds of thousands of users of the user population (e.g., 500,000 or more). Moreover, these measurements are taken by sensors of the CGM system at a continuous rate. As a result, the glucose measurements available to the system for model building and training may number in the millions, or even billions. With such a robust amount of data, the system can build and train the models to accurately mimic real-life effects of different behaviors on glucose levels. Absent the robustness of this aggregated data, conventional systems simply cannot build or train models to cover state spaces in a manner that suitably represents how various user behaviors and actions affect glucose levels. Failure to suitably cover these state spaces can result in glucose predictions or predictions of other health indicators that are inaccurate, which can lead to recommending unsafe actions or behaviors that could cause death. Given the gravity of generating inaccurate predictions, it is important to build the models using an amount of glucose measurements that is robust against rare events.

The CGM platform uses the models built and/or trained using the aggregated data in order to generate various predictions for users wearing the CGM system, as well as recommendations to improve predicted health conditions. The predictions may correspond to or otherwise include health indicators. As used herein, the term "health indicator" may refer to a predicted health condition, which can be "negative" or "positive." Examples of negative health conditions, for example, include pre-diabetes, Type I diabetes, Type II diabetes, neuropathy, Alzheimer's disease, and heart disease, to name just a few. In contrast, examples of "positive" health conditions, may include improved bloodwork, body composition, cardiovascular capacity, and so forth.

Moreover, predictions generated by the system may include generalized predictions or trends for the user population as a whole (e.g., drinking soda causes high blood glucose spikes which results in long term neuropathy, or eating a low carb diet lowers A1C), as well as specific predictions for individual users. For example, the system can apply a trained machine learning model to an individual user's glucose measurements and additional data over a particular time period in order to generate a user-specific prediction of a health indicator or event for the user, such as by predicting that the user will develop Type II diabetes or heart disease in the future. The system may generate an accuracy or probability associated with the prediction, as well as a time period associated with the prediction (e.g., 75% chance of developing Type II diabetes within 40 months). In some cases, the system may also generate short-term predictions for individual users based on real-time data. For example, a trained model may be applied to glucose measurements, heart rate, insulin level, and the like in real-time as the data is being captured in order to generate a predicted blood glucose level of the user in the near future (e.g., the next thirty minutes).

Based on these predictions, the CGM platform generates various recommendations. In some cases, a recommendation is generated based on logic that associates a predicted negative health condition with one or more actions or behaviors that mitigate the predicted negative health condition (e.g., reduce the probability of occurrence of the negative health condition). As such, the recommendation may include the one or more actions or behaviors intended to mitigate the predicted negative health condition. The recommendation, for instance, may instruct a user to perform an action (e.g., download an app to the computing device, seek medical attention immediately, dose insulin, go for a walk, consume a particular food or drink), continue a behavior (e.g., continue eating a certain way or exercising a certain way), change a behavior (e.g., change eating habits or exercise habits), and so on.

For example, based on the prediction that the user's blood glucose level will rise to a hyperglycemic level in the next 30 minutes, the CGM platform may generate a recommendation that includes actions intended to lower the user's blood glucose level, such as by recommending that the user dose insulin or go for a brisk walk. Conversely, based on a prediction that the user's glucose will decrease to a hypoglycemic level overnight, the CGM platform may generate a recommendation that the user eat a banana before going to sleep in order to keep the user's blood sugar level above the hypoglycemic level. As another example, based on a prediction that the user will develop Type II diabetes within 40 months, the CGM platform may generate a recommendation to adjust the user's diet or increase activity levels.

The predictions and recommendations generated by the CGM platform may be provided directly to the user, or to other parties or platforms associated with the user, such as a health care provider, a family member, third party services, and so forth. Such predictions and recommendations, for example, may be communicated to the user or other parties as electronic communications (e.g., email messages or text messages), notifications (e.g., in-app or on-device notifications), or uploaded to secure platforms or websites accessible via credentials.

In accordance with various implementations, the CGM platform includes one or more application programming interfaces (APIs) to enable the communication of glucose measurements and additional data back-and-forth between the CGM platform and one or more third parties. Such APIs may include an "egress" API which enables glucose measurements to be communicated from the CGM platform to various third parties which provide applications and services that utilize the glucose measurements collected by the CGM system. For example, users may be able to download such third party applications, and authorize these third party applications to access the user's glucose measurements. Doing so enables third party applications to leverage the glucose measurements in a variety of different ways to improve the user's health. In this way, third party service providers may be able to provide various services that use the glucose measurements, even though such third party service providers may not manufacture and deploy their own CGM systems.

The CGM platform may also include an "ingress" API which enables the CGM platform to receive "third party" data from the third party service providers. Such third party data may include application interaction data describing user interactions with third party services or applications. The CGM platform can aggregate the application interaction data, along with the user's glucose measurements and other data in order to determine whether the interaction with a particular application is improving the user's health. Based on this, the CGM platform may recommend that other users of the user population also utilize the particular application.

As part of this, the system may collect demographic data of a particular user, such as age, gender, location, and so forth. The glucose measurements collected from the user can be combined with the demographic data and additional data in order to generate a similarity score with other users in the user population. For example, a user who is 22 years old, female, has a mean glucose of 162 mg/dL, and experiences patterns of nighttime low glucose measurements, may have a high similarity score with other users in that age, gender, mean glucose measurement, and pattern experience. In this scenario, recommendations to utilize a particular application may be based on the user's similarity to other users in the population. For instance, if use of the particular application improves the glycemia of a subset of users in the user population, then the CGM platform can recommend use of the particular application to similar users in the user population.

In one or more implementations, the CGM platform includes a multi-state engagement system to generate state information identifying multiple, different states of engagement with CGM systems, e.g., with the CGM systems of the user population. These states may correspond to roles of users in relation to the CGM platform, e.g., patient, caregiver, health care provider, customer service representative, third-party service provider, commercial user (e.g., athlete, life hacker, etc.), performance coach, and so forth. These states may also correspond to stages of one or more sequences of engagement with CGM systems. In the context of a patient, a sequence of engagement may include, for instance, an inquiry stage (e.g., where a user inquires about or otherwise demonstrates interest in the CGM system or inquires about medical conditions related to diabetes), a selection stage (e.g., where the user is actively selecting among glucose monitoring solutions), a prescribed stage, an active use stage (e.g., where the user actively uses the CGM system along with functionality of the CGM platform), an erratic use stage (e.g., where a user's activity level declines some amount from a previous active use level and/or drops below a threshold amount of use), a discontinued use stage (e.g., where the user discontinues use of the CGM system and/or the CGM platform), a subsequent solution stage (e.g., where the user uses a different CGM system deployed by an entity that is different from the CGM platform), and so on.

Generally, the multi-state engagement system generates the state information identifying such states using one or more models (e.g., machine learning models). The multi-state engagement system may identify these states with such models using data captured about the user population, such as the CGM packages and additional data. Generally, the CGM packages may include data collected by the CGM system (e.g., glucose measurements sensed by the sensor and an identifier of the sensor) as well as supplemental data generated by a device that acts as an intermediary between the CGM system and the CGM platform. For example, the intermediary device, such as the user's mobile phone or smart watch, may generate a variety of supplemental data to supplement the CGM device data included in the CGM package. As described throughout, the additional data may include third party data, data from the IoT, physiological data, socioeconomic data, attitudinal data, behavioral data, purchase history data, complaint data, and payment data, to name just a few. In addition to identifying different states from this data describing the user population, the multi-state engagement system is also configured to determine which of these identified states correspond to a particular user at a given time, such as determining that a current state of the user includes a role as a patient that is currently in an erratic use stage with the CGM system. The multi-state engagement system may determine such states by providing data (e.g., a feature vector) describing the user as input to the machine learning models and receive output from these models indicating the state information indicative of the current state.

The state information generated by the multi-stage engagement system can be used to control communication with users of the CGM platform. For instance, when the state information includes a probability (e.g., of a user being in an erratic use stage at a current time) that is higher than a threshold probability, an intervention platform may deliver one or more communications to the user and/or deliver them to a customer service representative, e.g., notifications alerting the representative of erratic use. In this way, the intervention platform may communicate with the user (e.g., intervene) to determine if use of the CGM system has actually become erratic (or there is some error causing the use to appear erratic), why use has become erratic, and provide information to cause use to return to the "active" level.

In some cases, the multi-state engagement system can predict a transition to a negative state (e.g., a discontinued use stage) before the transition actually occurs so that the intervention system can attempt to prevent the transition to the negative state. To do so, the state information generated by the multi-state engagement system may include transition probabilities indicative of a probability that the user will transition from the current state to a different state in the near future, e.g., the probability that a user will transition from an active use stage to an erratic use stage or from an erratic use stage to a discontinued use stage. The state information may also include driving factors predicted by the multi-state engagement system as likely to drive the transition to the new state. Based on the transition probabilities and the driving factors, the intervention platform generates various intervention strategies to prevent the transition. In some cases, such intervention strategies may include exposing the state information to a user that has been authorized to intervene in certain scenarios by communicating with users, e.g., a customer service representative, clinician, and so forth. By way of example, the intervention platform may provide the state information (or notifications derived based on the state information) through an intervention portal, e.g., where a customer service representative can review state information for multiple users. The exposed state information may enable an authorized user of the intervention platform to determine whether to communicate with a user associated with the state information or not, such as whether to initiate a telephone call to the user, send an email to the user, send an SMS message to the user and so forth. Alternately or additionally, the intervention platform may be configured to automatically generate and communicate the communication based on the state information, such as according to logic that instructs the intervention platform to communicate in particular ways depending on the state information.

Regardless of whether the intervention strategy includes exposing transition information to a human or is automated, the intervention platform can customize the intervention strategy based on the determined factors driving the predicted transition from the current state to the new state. By way of example, if the state information indicates that faulty equipment (e.g., a faulty sensor) is being used and an amount of use has dropped since beginning use of the faulty equipment, a customer service representative may deploy a strategy specific to replacing the faulty equipment, e.g., sending new, properly working equipment. As another example, if the state information indicates abnormally high blood glucose readings are causing user frustration which will likely lead to discontinued use, then the intervention system may communicate a message to the user that includes success stories of other users in the population who have reduced their blood glucose levels while wearing the CGM system through diet and exercise.

It is to be appreciated that unlike conventional systems, the CGM platform has access to CGM packages for hundreds of thousands of users of the user population (e.g., 500,000 or more). Moreover, the CGM measurements included in these CGM packages are taken by sensors of the CGM system at a continuous rate. As a result, the glucose measurements, and the data describing these measurements (e.g., the CGM packages), available to the engagement state model manager for building and training machine learning models amounts to millions, or even billions of data points. With such a robust amount of data, the system can build and train the various models to accurately identify multiple, different states of engagement by the user population with the CGM system and the CGM platform.

Absent the robustness of the CGM platform's glucose measurements—as well as data describing characteristics of these measurements and receipt by the CGM platform of the CGM packages—conventional systems simply cannot build or train models to cover state spaces in a manner that suitably represents how users actually engage in the real world with the CGM system and the CGM platform. Failure to suitably cover these state spaces can result in predicting states of use with the CGM system and the CGM platform that are inaccurate, which can lead to intervention that is too late (or is never carried out) to prevent potentially unsafe conditions with the CGM system or prevent discontinued use of the CGM system and the CGM platform. Given the gravity of inaccurately identifying states which indicate how users actually interact with the CGM system, it is important to build the engagement state models using an amount of CGM packages that is robust enough to capture patterns of any spurious correlations or hidden relationships in the data.

In the following discussion, an example environment is first described that may employ the techniques described herein. Example implementation details and procedures are then described which may be performed in the example environment as well as other environments. Performance of the example procedures is not limited to the example environment and the example environment is not limited to performance of the example procedures.

Example Environment

FIG. 1 is an illustration of an environment 100 in an example implementation that is operable to employ multi-state engagement with continuous glucose monitoring (CGM) systems as described herein. The illustrated environment 100 includes person 102, who is depicted wearing a CGM system 104, insulin delivery system 106, and computing device 108. The illustrated environment 100 also includes other users in a user population 110 of the CGM system, CGM platform 112, and Internet of Things 114 (IoT 114). The CGM system 104, insulin delivery system 106, computing device 108, user population 110, CGM platform 112, and IoT 114 are communicatively coupled, one to another, via a network 116.

Alternately or additionally, one or more of the CGM system 104, the insulin delivery system 106, and the computing device 108 may be communicatively coupled in other ways, such as using one or more short range communication protocols or techniques. For example, the CGM system 104, the insulin delivery system 106, and the computing device 108 may communicate with one another using one or more of Bluetooth, near-field communication (NFC), 5G, and so forth. The CGM system 104, the insulin delivery system 106, and the computing device 108 may leverage these types of communication to form a closed-loop system between one another. In this way, the insulin delivery system 106 may deliver insulin based on glucose predictions computed in real-time (e.g., by the computing device 108) as glucose measurements are obtained by the CGM system 104.

In accordance with the described techniques, the CGM system 104 is configured to monitor glucose of the person 102 continuously. The CGM system 104 may be configured with a CGM sensor, for instance, that continuously detects analytes indicative of the person 102's glucose and enables generation of glucose measurements. In the illustrated environment 100 these measurements are represented as glucose measurements 118. This functionality along with further aspects of the CGM system 104's configuration are discussed in more detail in relation to FIG. 2.

In one or more implementations, the CGM system 104 transmits the glucose measurements 118 to the computing device 108, such as via Bluetooth. The CGM system 104 may communicate these measurements in real-time, e.g., as they are produced using a CGM sensor. Alternately or in addition, the CGM system 104 may communicate the glucose measurements 118 to the computing device 108 at set time intervals, e.g., every 30 seconds, every minute, every hour, every 6 hours, every day, and so forth. Further still, the CGM system 104 may communicate these measurements responsive to a request from the computing device 108, e.g., communicated to the CGM system 104 when the computing device 108 causes display of a user interface having information about the person 102's glucose level, updates such a display, predicts the person 102's upcoming glucose level for the purpose of delivering insulin, and so forth. Accordingly, the computing device 108 may maintain the glucose measurements 118 of the person 102 at least temporarily, e.g., in computer readable storage media of the computing device 108.

Although illustrated as a wearable device (e.g., a smart watch), the computing device 108 may be configured in a variety of ways without departing from the spirit or scope of the described techniques. By way of example and not limitation, the computing device 108 may be configured as a different type of mobile device (e.g., a mobile phone or tablet device). In one or more implementations, the computing device 108 may be configured as a dedicated device associated with the CGM platform 112, e.g., with functionality to obtain the glucose measurements 118 from the CGM system 104, perform various computations in relation to the glucose measurements 118, display information related to the glucose measurements 118 and the CGM platform 112, communicate the glucose measurements 118 to the CGM platform 112, and so forth. In contrast to implementations where the computing device 108 is configured as a mobile phone, however, the computing device 108 may not include some functionality available with mobile phone or wearable configurations when configured as a dedicated CGM device, such as the ability to make phone calls, camera functionality, the ability to utilize social networking applications, and so on.

Additionally, the computing device 108 may be representative of more than one device in accordance with the described techniques. In one or more scenarios, for instance, the computing device 108 may correspond to both a wearable device (e.g., a smart watch) and a mobile phone. In such scenarios, both of these devices may be capable of performing at least some of the same operations, such as to receive the glucose measurements 118 from the CGM system 104, communicate them via the network 116 to the CGM platform 112, display information related to the glucose measurements 118, and so forth. Alternately or in addition, different devices may have different capabilities that other devices do not have or that are limited through computing instructions to specified devices. In the scenario where the computing device 108 corresponds to a separate smart watch and a mobile phone, for instance, the smart watch may be configured with various sensors and functionality to measure a variety of physiological markers (e.g., heartrate, breathing, rate of blood flow, and so on) and activities (e.g., steps) of the person 102. In this scenario, the mobile phone may not be configured with these sensors and functionality or may include a limited amount of that functionality—although in other scenarios a mobile phone may be able to provide the same functionality. Continuing with this particular scenario, the mobile phone may have capabilities that the smart watch does not have, such as an amount of computing resources (e.g., battery and processing speed) that enables the mobile phone to more efficiently carry out computations in relation to the glucose measurements 118. Even in scenarios where a smart watch is capable of carrying out such computations, computing instructions may limit performance of those computations to the mobile phone so as not to burden both devices and to utilize available resources efficiently. To this extent, the computing device 108 may be configured in different way and represent different numbers of devices than discussed herein without departing from the spirit and scope of the described techniques.

As mentioned above, the computing device 108 communicates the glucose measurements 118 to the CGM platform 112. In the illustrated environment 100, the glucose measurements 118 are shown stored in storage device 120 of the CGM platform 112 as part of CGM data 122. The storage device 120 may represent one or more databases and also other type of storage capable of storing the CGM data 122. The CGM data 122 also includes user profile 124. In accordance with the described techniques, the person 102 corresponds to a user of at least the CGM platform 112 and may also be a user of one or more other, third party service providers. To this end, the person 102 may be associated with a username and be required, at some time, to provide authentication information (e.g., password, biometric data, and so forth) to access the CGM platform 112 using the username. This information may be captured in the user profile 124. The user profile 124 may also include a variety of other information about the user, such as demographic information describing the person 102, information about a health care provider, payment information, prescription information, determined health indicators, user preferences, account information for other service provider systems (e.g., a service provider associated with a wearable, social networking systems, and so on), and so forth. The user profile 124 may include different information about a user within the spirit and scope of the described techniques.

Further, the CGM data 122 not only represents data of a user that corresponds to the person 102, but also represents data of the other users in the user population 110. Given this, the glucose measurements 118 in the storage device 120 include the glucose measurements from a CGM sensor of the CGM system 104 worn by the person 102 and also include glucose measurements from CGM sensors of CGM systems worn by persons corresponding to the other users in the user population 110. It follows also that the glucose measurements 118 of these other users are communicated by their respective devices via the network 116 to the CGM platform 112 and that these other users have respective user profiles 124 with the CGM platform 112.

The data analytics platform 126 represents functionality to process the CGM data 122 to generate a variety of predictions, such as by using various machine learning models. Based on these predictions, the CGM platform 112 may provide recommendations and/or other information about the predictions. For instance, the CGM platform 112 may provide the recommendations or other information directly to the user, to a medical professional associated with the user, and so forth. The specific types of predictions, recommendations, and other information are described in more detail below. Although depicted as separate from the computing device 108, portions or an entirety of the data analytics platform 126 may alternately or additionally be implemented at the computing device 108. The data analytics platform 126 is also configured to generate these predictions using data in addition to the glucose measurements 118, such as additional data obtained via the IoT 114.

It is to be appreciated that the IoT 114 represents various sources capable of providing data that describes the person 102 and the person 102's activity as a user of one or more service providers and activity with the real world. By way of example, the IoT 114 may include various devices of the user, e.g., cameras, mobile phones, laptops, and so forth. To this end, the IoT 114 may provide information about interaction of the user with various devices, e.g., interaction with web-based applications, photos taken, communications with other users, and so forth. The IoT 114 may also include various real-world articles (e.g., shoes, clothing, sporting equipment, appliances, automobiles, etc.) configured with sensors to provide information describing behavior, such as steps taken, force of a foot striking the ground, length of stride, temperature of a user (and other physiological measurements), temperature of a user's surroundings, types of food stored in a refrigerator, types of food removed from a refrigerator, driving habits, and so forth. The IoT 114 may also include third parties to the CGM platform 112, such as medical providers (e.g., a medical provider of the person 102) and manufacturers (e.g., a manufacturer of the CGM system 104, the insulin delivery system 106, or the computing device 108) capable of providing medical and manufacturing data, respectively, that can be leveraged by the data analytics platform 126. Certainly, the IoT 114 may include devices and sensors capable of providing a wealth of data in connection with recommendations based on CGM without departing from the spirit or scope of the described techniques. In the context of measuring glucose, e.g., continuously, and obtaining data describing such measurements, consider the following discussion of FIG. 2.

Figure 2:
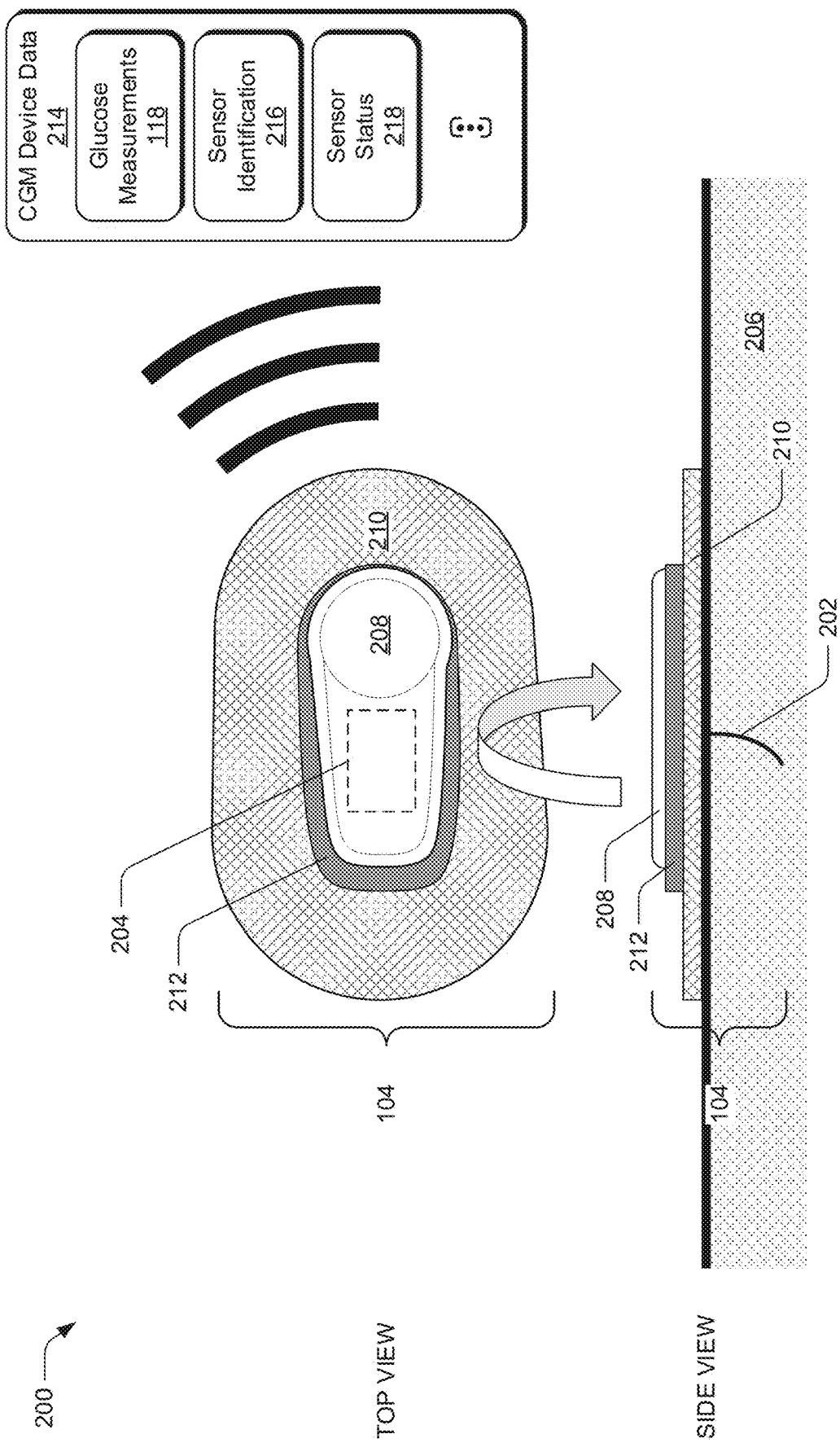
FIG. 2 depicts an example of the continuous glucose monitoring (CGM) system of FIG. 1 in greater detail.

FIG. 2 depicts an example implementation 200 of the CGM system 104 of FIG. 1 in greater detail. In particular, the illustrated example 200 includes a top view and a corresponding side view of the CGM system 104.

The CGM system 104 is illustrated to include a sensor 202 and a sensor module 204. In the illustrated example 200, the sensor 202 is depicted in the side view having been inserted subcutaneously into skin 206, e.g., of the person 102. The sensor module 204 is depicted in the top view as a dashed rectangle. The CGM system 104 also includes a transmitter 208 in the illustrated example 200. Use of the dashed rectangle for the sensor module 204 indicates that it may be housed or otherwise implemented within a housing of the transmitter 208. In this example 200, the CGM system 104 further includes adhesive pad 210 and attachment mechanism 212.

In operation, the sensor 202, the adhesive pad 210, and the attachment mechanism 212 may be assembled to form an application assembly, where the application assembly is configured to be applied to the skin 206 so that the sensor 202 is subcutaneously inserted as depicted. In such scenarios, the transmitter 208 may be attached to the assembly after application to the skin 206 and via the attachment mechanism 212. Additionally or alternatively, the transmitter 208 may be incorporated as part of the application assembly, such that the sensor 202, the adhesive pad 210, the attachment mechanism 212, and the transmitter 208 (with the sensor module 204) can all be applied at once to the skin 206. In one or more implementations, this application assembly is applied to the skin 206 using a separate applicator (not shown). This application assembly may also be removed by peeling the adhesive pad 210 off of the skin 206. It is to be appreciated that the CGM system 104 and its various components as illustrated are simply one example form factor, and the CGM system 104 and its components may have different form factors without departing from the spirit or scope of the described techniques.

In operation, the sensor 202 is communicatively coupled to the sensor module 204 via at least one communication channel which can be a "wireless" connection or a "wired" connection. Communications from the sensor 202 to the sensor module 204 or from the sensor module 204 to the sensor 202 can be implemented actively or passively and these communications can be continuous (e.g., analog) or discrete (e.g., digital).

The sensor 202 may be a device, a molecule, and/or a chemical which changes or causes a change in response to an event which is at least partially independent of the sensor 202. The sensor module 204 is implemented to receive indications of changes to the sensor 202 or caused by the sensor 202. For example, the sensor 202 can include glucose oxidase which reacts with glucose and oxygen to form hydrogen peroxide that is electrochemically detectable by the sensor module 204 which may include an electrode. In this example, the sensor 202 may be configured as or include a glucose sensor configured to detect analytes in blood or interstitial fluid that are indicative of glucose level using one or more measurement techniques.

In another example, the sensor 202 (or an additional sensor of the CGM system 104—not shown) can include a first and second electrical conductor and the sensor module 204 can electrically detect changes in electric potential across the first and second electrical conductor of the sensor 202. In this example, the sensor module 204 and the sensor 202 are configured as a thermocouple such that the changes in electric potential correspond to temperature changes. In some examples the sensor module 204 and the sensor 202 are configured to detect a single analyte, e.g., glucose. In other examples, the sensor module 204 and the sensor 202 are configured to detect multiple analytes, e.g., sodium, potassium, carbon dioxide, and glucose. Alternately or additionally, the CGM system 104 includes multiple sensors to detect not only one or more analytes (e.g., sodium, potassium, carbon dioxide, and glucose) but also one or more environmental conditions (e.g., temperature). Thus, the sensor module 204 and the sensor 202 (as well as any additional sensors) may detect the presence of one or more analytes, the absence of one or more analytes, and/or changes in one or more environmental conditions.

In one or more implementations, the sensor module 204 may include a processor and memory (not shown). The sensor module 204, by leveraging the processor, may generate the glucose measurements 118 based on the communications with the sensor 202 that are indicative of the above-discussed changes. Based on these communications from the sensor 202, the sensor module 204 is further configured to generate CGM device data 214. The CGM device data 214 is a communicable package of data that includes at least one glucose measurement 118. Alternately or additionally, the CGM device data 214 includes other data, such as multiple glucose measurements 118, sensor identification 216, sensor status 218, and so forth. In one or more implementations, the CGM device data 214 may include other information such as one or more of temperatures that correspond to the glucose measurements 118 and measurements of other analytes. It is to be appreciated that the CGM device data 214 may include a variety of data in addition to at least one glucose measurement 118 without departing from the spirit or scope of the described techniques.

In operation, the transmitter 208 may transmit the CGM device data 214 wirelessly as a stream of data to the computing device 108. Alternately or additionally, the senor module 204 may buffer the CGM device data 214 (e.g., in memory of the sensor module 204) and cause the transmitter 208 to transmit the buffered CGM device data 214 at various intervals, e.g., time intervals (every second, every thirty seconds, every minute, every hour, and so on), storage intervals (when the buffered CGM device data 214 reaches a threshold amount of data or a number of instances of CGM device data 214), and so forth.

In addition to generating the CGM device data 214 and causing it to be communicated to the computing device 108, the sensor module 204 may include additional functionality in accordance with the described techniques. This additional functionality may include generating predictions of glucose levels of the person 102 in the future and communicating notifications based on the predictions, such as by communicating warnings when the predictions indicate that the person 102's level of glucose is likely to be dangerously low in the near future. This computational ability of the sensor module 204 may be advantageous especially where connectivity to services via the network 116 is limited or non-existent. In this way, a person may be alerted to a dangerous condition without having to rely on connectivity, e.g., to the Internet. This additional functionality of the sensor module 204 may also include calibrating the sensor 202 initially or on an ongoing basis as well as calibrating any other sensors of the CGM system 104.

With respect to the CGM device data 214, the sensor identification 216 represents information that uniquely identifies the sensor 202 from other sensors, such as other sensors of other CGM systems 104, other sensors implanted previously or subsequently in the skin 206, and so on. By uniquely identifying the sensor 202, the sensor identification 216 may also be used to identify other aspects about the sensor, 202 such as a manufacturing lot of the sensor 202, packaging details of the sensor 202, shipping details of the sensor 202, and so on. In this way, various issues detected for sensors manufactured, packaged, and/or shipped, in a similar manner as the sensor 202 may be identified and used in different ways, e.g., to calibrate the glucose measurements 118, to notify users to change defective sensors or dispose of them, to notify manufacturing facilities of machining issues, and so forth.

The sensor status 218 represents a state of the sensor 202 at a given time, e.g., a state of the sensor at a same time one of the glucose measurements 118 is produced. To this end, the sensor status 218 may include an entry for each of the glucose measurements 118, such that there is a one-to-one relationship between the glucose measurements 118 and statuses captured in the sensor status 218 information. Generally speaking, the sensor status 218 describes an operational state of the sensor 202. In one or more implementations, the sensor module 204 may identify one of a number of predetermined operational states for a given glucose measurement 118. The identified operational state may be based on the communications from the sensor 202 and/or characteristics of those communications.

By way of example, the sensor module 204 may include (e.g., in memory or other storage) a lookup table having the predetermined number of operational states and bases for selecting one state from another. For instance, the predetermined states may include a "normal" operation state where the basis for selecting this state may be that the communications from the sensor 202 fall within thresholds indicative of normal operation, e.g., within a threshold of an expected time, within a threshold of expected signal strength, an environmental temperature is within a threshold of suitable temperatures to continue operation as expected, and so forth. The predetermined states may also include operational states that indicate one or more characteristics of the sensor 202's communications are outside of normal activity and may result in potential errors in the glucose measurements 118.

For example, bases for these non-normal operational states may include receiving the communications from the sensor 202 outside of a threshold expected time, detecting a signal strength of the sensor 202 outside a threshold of expected signal strength, detecting an environmental temperature outside of suitable temperatures to continue operation as expected, detecting that the person 102 has rolled (e.g., in bed) onto the CGM system 104, and so forth. The sensor status 218 may indicate a variety of aspects about the sensor 202 and the CGM system 104 without departing from the spirit or scope of the described techniques.

Having considered an example environment and example CGM system, consider now a discussion of some example details of the techniques for multi-state engagement with CGM systems in a digital medium environment in accordance with one or more implementations.

Multi-State Engagement with CGM Systems

Figure 3:
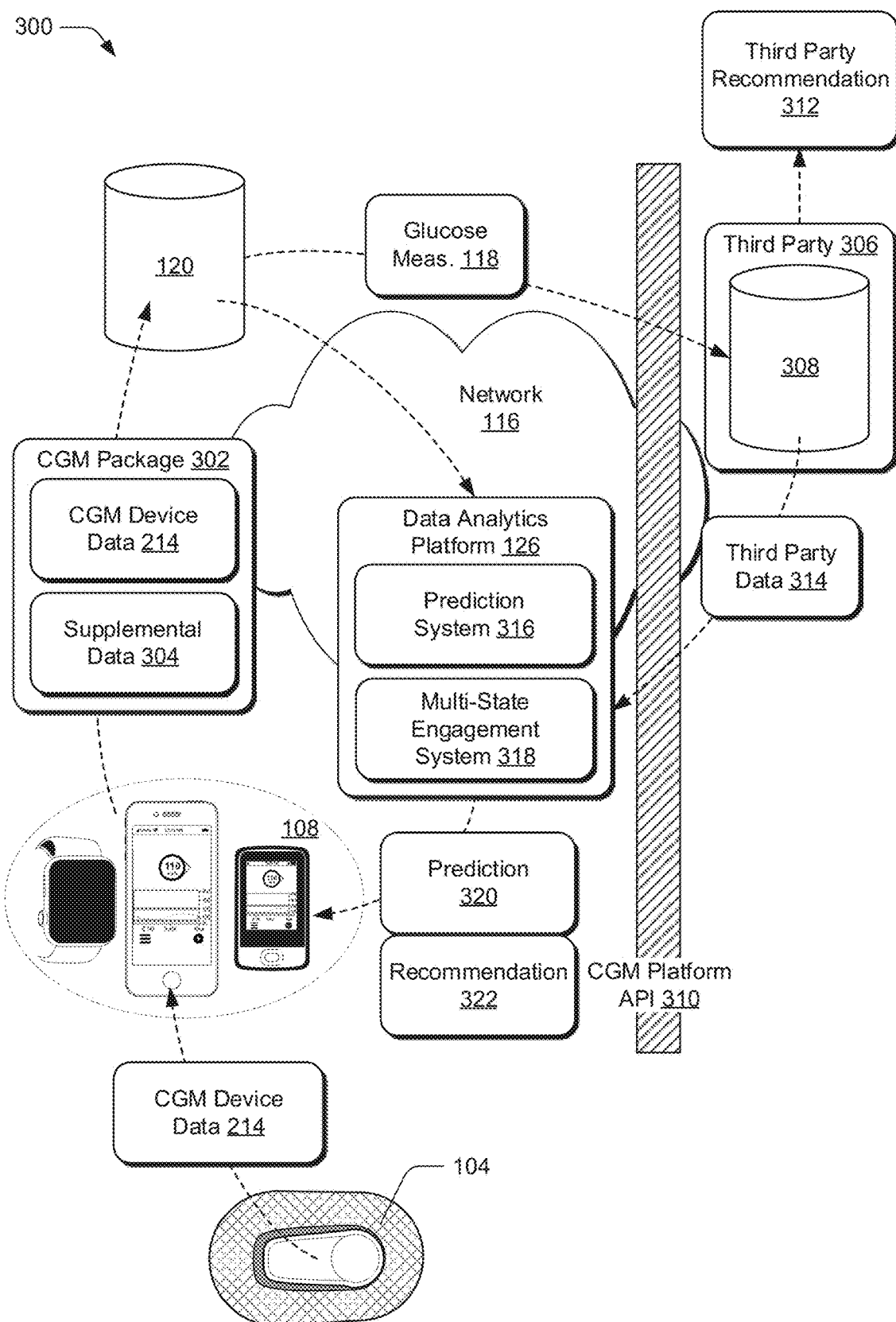
FIG. 3 depicts an example implementation in which CGM device data, including glucose measurements, is routed to different systems to enable provision of CGM-related services.

FIG. 3 depicts an example implementation 300 in which CGM device data, including glucose measurements, is routed to different systems to enable provision of CGM-related services.

The illustrated example 300 includes from FIG. 1 the CGM system 104 and examples of the computing device 108. The illustrated example 300 also includes the data analytics platform 126 and the storage device 120, which, as discussed above, stores the CGM data 122, including the glucose measurements 118. In this example 300, the CGM system 104 is depicted transmitting the CGM device data 214 to the computing device 108. As discussed above in relation to FIG. 2, the CGM device data 214 includes the glucose measurements 118 along with other data. The CGM system 104 may transmit the CGM device data 214 to the computing device 108 in a variety of ways.

The illustrated example 300 also includes CGM package 302. The CGM package 302 may include the CGM device data 214 (e.g., glucose measurements 118, sensor identification 216, and sensor status 218), supplemental data 304, or portions thereof. In this example 300, the CGM package 302 is depicted being routed from the computing device 108 to the storage device 120 of the CGM platform 112. Broadly speaking, the computing device 108 includes functionality to generate the supplemental data 304 based, at least in part, on the CGM device data 214, package the supplemental data 304 together with the device data 214 to form the CGM package 302, and communicate the CGM package 302 to the CGM platform 112 for storage in the storage device 120, e.g., via the network 116. It is to be appreciated, therefore, that the CGM package 302 may include data collected by the CGM system 104 (e.g., glucose measurements 118 sensed by the sensor 202) as well as supplemental data 304 generated by computing device 108 that acts as an intermediary between the CGM system 104 and the CGM platform 112, such as a mobile phone or a smart watch of the user.

With respect to the supplemental data 304, the computing device 108 may generate a variety of supplemental data to supplement the CGM device data 214 included in the CGM package 302. In accordance with the described techniques, the supplemental data 304 may describe one or more aspects of a user's context, such that correspondences of the user's context with CGM device data 214 (e.g., glucose measurements 118) can be identified. By way of example, the supplemental data 304 may describe user interaction with the computing device 108, and include, for instance, data extracted from application logs describing interaction (e.g., selections made, operations performed) for particular applications. The supplemental data 304 may also include clickstream data describing clicks, taps, and presses performed in relation to input/output interfaces of the computing device 108. As another example, the supplemental data 304 may include gaze data describing where a user is looking (e.g., in relation to a display device associated with the computing device 108 or when the user is looking away from the device), voice data describing audible commands and other spoken phrases of the user or other users (e.g., including passively listening to users), device data describing the device (e.g., make, model, operating system and version, camera type, apps the computing device 108 is running), and so on. The supplemental data 304 may also describe other aspects of a user's context, such as environmental aspects including, for example, a location of the user, a temperature at the location (e.g., outdoor generally, proximate the user using temperature sensing functionality), weather at the location, an altitude of the user, barometric pressure, context information obtained in relation to the user via the IoT 114 (e.g., food the user is eating, a manner in which a user is using sporting equipment, clothes the user is wearing), and so forth. The supplemental data 304 may also describe health-related aspects detected about a user including, for example, steps, heart rate, perspiration, a temperature of the user (e.g., as detected by the computing device 108), and so forth. To the extent that the computing device 108 may include functionality to detect, or otherwise measure, some of the same aspects as the CGM system 104, the data from these two sources may be compared, e.g., for accuracy, fault detection, and so forth. The above-discussed types of the supplemental data 304 are merely examples and the supplemental data 304 may include more, fewer, or different types of data without departing from the spirit or scope of the techniques described herein.

Regardless of how robustly the supplemental data 304 describes a context of a user, the computing device 108 may communicate CGM packages 302, containing the CGM device data 214 and supplemental data 304, to the CGM platform 112 for processing at various intervals. In one or more implementations, the computing device 108 may stream CGM packages 302 to the CGM platform 112 substantially in real-time, e.g., as the CGM system 104 provides the CGM device data 214 continuously to the computing device 108. The computing device 108 may alternately or additionally communicate one or more of the CGM packages 302 to the CGM platform 112 at a predetermined interval, e.g., every second, every 30 seconds, every hour, and so on.

Although not depicted in the illustrated example 300, the CGM platform 112 may process these CGM packages 302 and cause at least some of the CGM device data 214 and the supplemental data 304 to be stored in the storage device 120. From the storage device 120, this data may be provided to, or otherwise accessed by, the data analytics platform 126, e.g., to generate various predictions and provide recommendations, as described in more detail below. Alternately or additionally, the data may be provided to a third party 306, such as a third party service provider. In this way, third party service providers may be able to provide various services that use the glucose measurements 118, even though such third party service providers may not manufacture and deploy their own CGM systems.

In the illustrated example 300, the glucose measurements 118 are depicted being communicated from the storage device 120 of the CGM platform 112 to storage device 308 (or other types of storage) of the third party 306 over the network 116. In particular, the glucose measurements 118 are depicted being communicated across CGM platform application programming interface (API) 310. In this type of scenario, the CGM platform API 310 may be considered an "egress" for data, such as the glucose measurements 118. By "egress" it is meant that a flow of data is generally outward from the CGM platform 112 to the third party 306.

In one or more implementations, the CGM platform 112 provides access to data from the storage device 120 via the CGM platform API 310. In the context of data provision, the CGM platform API 310 may expose one or more "calls" (e.g., specific formats for data requests) to the third party 306. By way of example, the CGM platform API 310 may expose calls to the third party 306 after the third party 306 enters into an agreement, e.g., with a business corresponding to the CGM platform 112, that allows the third party 306 to obtain data from the storage device 120 via the CGM platform API 310. As part of this agreement, the third party 306 may agree to exchange payment in order to obtain data from the CGM platform 112. Alternately or additionally, the third party 306 may agree to exchange data that it produces, e.g., via an associated device, in order to obtain data from the CGM platform 112. Parties that enter into agreements to obtain data (e.g., the glucose measurements 118) from the CGM platform 112 via the CGM platform API 310 may be referred to as "data partners."

Broadly speaking, the CGM platform API 310 allows the third party 306 to make a request for data (e.g., glucose measurements 118) in a specific request format, and if the request is made in the specific format, then the CGM platform API 310 provides the requested data in a specific response format. In other words, the CGM platform API 310 is configured to receive requests for the glucose measurements 118 in a specific request format from the third party 306, obtain the requested glucose measurements 118 from the storage device 120, and provide the requested glucose measurements 118 in a formatted response to the third party 306. The CGM platform API 310 may expose calls that enable the third party 306 to request one or more periods of time of the glucose measurements 118 (e.g., the last 10 days), the glucose measurements 118 for particular users or segments of users, the glucose measurements 118 for a number of users (e.g., 10,000 users) and over a specified period of time (e.g., the last 10 days), and so on. The CGM platform 310 may expose a variety of calls that enable third parties to request glucose measurements 118 meeting specified criteria in a variety of ways without departing from the spirit or scope of the described techniques. In operation, the CGM platform API 310 may limit which data is accessible to different third parties depending on terms of a corresponding agreement, such as to limit a frequency at which the glucose measurements 118 can be obtained, introduce latency to provision of the glucose measurements 118 after those measurements are obtained from the CGM system 104 and the computing devices 108, and so forth.

Once the third party 306 obtains the glucose measurements 118, the third party 306 may generate one or more third party recommendations 312 based on the obtained glucose measurements 118. By way of example, the third party 306 may provide a lifestyle application to users and use the glucose measurements 118 to provide the third party recommendation 312 in relation to one or more lifestyle behaviors tracked via such an application, such as a recommendation to exercise more, a recommendation to exercise less, a recommendation to continue certain behaviors (e.g., steps, eating certain foods, sleeping), recommendations to decrease or eliminate certain behaviors (e.g., eating certain foods, drinking alcohol, sleeping), and so forth. Examples of lifestyle applications may include exercise applications, health measurement applications, food tracking applications, sport-specific applications, and so forth.

As noted above, the third party 306 may produce its own, additional data, such as via devices that the third party 306 manufactures and/or deploys, e.g., wearable devices. Given this, the third party 306 may generate the third party recommendation 312 based not only on the glucose measurements 118 but also on the additional data the third party 306 produces. For instance, the third party 306 may provide the obtained glucose measurements 118 and this additional data as input to one or more machine learning models trained using historical glucose measurements 118 and historical additional data. Responsive to this input, the third party 306 obtains at least one prediction generated by the one or more models as output. The third party 306 may use such predictions as a basis for the third party recommendation 312. The third party recommendations 312 are illustrated being output by the third party 306. This represents that the third party 306 may deliver a third party recommendation 312 by communicating it over the network 116 to the computing device 108 or to other computing devices, e.g., computing devices of the user population 110. The third party recommendation 312 may then be output by a receiving computing device, such as by displaying the recommendation, outputting the recommendation audibly, and so forth.

The illustrated example 300 also includes third party data 314, which is shown being communicated from the third party to the data analytics platform 126. As mentioned above, the third party 306 may manufacture and/or deploy associated devices. Additionally or alternately, the third party 306 may obtain data through other sources, such as corresponding applications. This data may thus include user-entered data entered via corresponding third party applications, e.g., social networking applications, lifestyle applications, and so forth. Given this, the data produced by the third party 306 may be configured in various ways, including as proprietary data structures, text files, images obtained via mobile devices of users, formats indicative of text entered to exposed fields or dialog boxes, formats indicative of option selections, and so forth. The third party data 314 may describe various aspects related to one or more services provided by a third party without departing from the spirit or scope of the described techniques. The third party data 314 may include, for instance, application interaction data which describes usage or interaction by users with a particular application provided by the third party 306. Generally, the application interaction data enables the data analytics platform 126 to determine usage, or an amount of usage, of a particular application by users of the user population 110. Such data, for example, may include data extracted from application logs describing user interactions with a particular application, clickstream data describing clicks, taps, and presses performed in relation to input/output interfaces of the application, and so forth. In one or more implementations, the data analytics platform 126 may thus receive the third party data 314 produced or otherwise obtained by the third party 306.

In the illustrated example 300, the third party data 314 is depicted being communicated across the CGM platform API 310. In this type of scenario, the CGM platform API 310 may be considered an "ingress" for the third party data 314. By "ingress" it is meant that a flow of data is generally inward to the CGM platform 112 from the third party 306. Although the CGM platform API 310 is illustrated as supporting both egress and ingress data flows, in one or more implementations, the functionality to allow egress of data from the CGM platform 112 and ingress of data to the CGM platform 112 may be handled by different APIs. For example, the ingress functionality may be handled by an API that corresponds to the third party 306 rather than the CGM platform 112's API. Regardless, in addition to the data of the CGM platform 112—the glucose measurements 118 and the supplemental data 304—the data analytics platform 126 may utilize third party data 314 in one or more scenarios.

The data analytics platform 126 is illustrated with prediction system 316 and multi-state engagement system 318. In accordance with the described systems, the prediction system 316 is configured to generate predictions 320 based on at least the glucose measurements 118. In one or more implementations, for instance, the prediction system 316 generates predictions 320 based on both the glucose measurements 118 and additional data, where the additional data may include one or more portions of the CGM device data 214 additional to the glucose measurements 118, the supplemental data 304, the third party data 314, data from the IoT 114, and so forth. As discussed below, the prediction system 316 may generate such predictions 320 by using one or more machine learning models. These models may be trained or otherwise built using the glucose measurements 118 and additional data obtained from the user population 110.

In one or more implementations, the predictions 320 may correspond to or otherwise include health indicators. As used herein, the term "health indicator" may refer to a predicted health condition, which can be "negative" or "positive." Examples of negative health conditions, for example, include pre-diabetes, Type I diabetes, Type II diabetes, neuropathy, Alzheimer's disease, and heart disease, to name just a few. In contrast, examples of "positive" health conditions, may include predicting a decreased risk of developing a negative health condition, or a positive health condition related to bodyfat, cardiovascular capability, and so forth. In some cases, the health indicator may refer to a predicted medical state, such as a predicted A1C. Notably, the predictions 320 are based on glucose measurements 118 and additional data collected during a certain time period. Thus, in some cases, the predictions 320 predict that the user currently has the predicted health condition based on the aggregated data. Alternately, the predicted health condition may correspond to a time period that occurs after the certain time period during which the aggregated data is collected (e.g., a prediction of Type II diabetes in 40 months). Some additional types of predictions and the specific types of information used to generate these predictions is also discussed in further detail below.

Based on the generated predictions 320, the data analytics platform 126 generates recommendation 322. The recommendation 322, for instance, may instruct a user to perform an action (e.g., download an app to the computing device 108, seek medical attention immediately, dose insulin, go for a walk, consume a particular food or drink), continue a behavior (e.g., continue eating a certain way or exercising a certain way), change a behavior (e.g., change eating habits or exercise habits), and so on. In such scenarios, the prediction 320 and/or the recommendation 322 is communicated from the data analytics platform 126 and output via the computing device 108. In the illustrated example 300, the prediction 320 is also illustrated being communicated to the computing device 108. It is to be appreciated that either or both of the prediction 320 and the recommendation 322 may be communicated to the computing device 108. Additionally or alternately the prediction 320 and/or the recommendation 322 may be routed to a decision support platform and/or a validation platform, e.g., before the prediction 320 and/or recommendation 322 are allowed to be delivered to the computing device 108.

Turning now to a discussion of the multi-state engagement system 318, in accordance with the described techniques. Broadly speaking, the multi-state engagement system 318 is configured to identify multiple, different states of engagement with CGM systems, e.g., with the CGM systems 104 of the user population 110. These states may correspond to roles of users in relation to the CGM platform 112. As used herein, a "role" may refer to a manner in which a user interacts with the CGM platform 112, including which functionality of the CGM platform 112 is accessible to and/or used by the user. In other words, roles may correspond, at least in part, to whether a user wears particular systems deployed by the CGM platform 112, uses particular applications deployed by the CGM platform 112, uses particular functionality of those applications, and so on. Some example roles may include, for instance, patient, caregiver (e.g., parent or guardian), health care provider, customer service representative, third-party service provider, commercial user (e.g., athlete, life hacker, etc.), and performance coach, to name just a few. A "current role", therefore, corresponds to a role of the user at a current time period. To this extent, the role of a user may change over time, such that a user has different roles at different times and also such that a user may have one or more previous roles and one or more subsequent roles.

These states may also correspond to stages of one or more sequences of engagement with CGM systems. In the context of a patient, a sequence of engagement may include, for instance, an inquiry stage (e.g., where a user inquires about or otherwise demonstrates interest in the CGM system 104 or inquires about medical conditions related to diabetes), a selection stage (e.g., where the user is actively selecting among glucose monitoring solutions), a prescribed stage, an active use stage (e.g., where the user actively uses the CGM system 104 along with functionality of the CGM platform 112), an erratic use stage (e.g., where a user's activity level declines some amount from a previous active use level and/or drops below a threshold amount of use), a discontinued use stage (e.g., where the user discontinues use of the CGM system 104 and/or the CGM platform 112), a subsequent solution stage (e.g., where the user uses a different CGM system deployed by an entity that is different from the CGM platform 112), and so on.

As discussed in more detail below, the multi-state engagement system 318 may identify such states using one or more machine learning models. The multi-state engagement system 318 may identify these states with such models using data captured about the user population 110, such as the CGM packages 302 and additional data, where the additional data may include the third party data 314, data from the IoT 114, and so forth. In one or more implementations, this additional data may also include physiological data (e.g., data related to the body, such as heart rate, breathing rate, and so forth), environmental data, socioeconomic data, attitudinal data (e.g., data indicative of user perception towards a brand or manufacturer of the CGM system), behavioral data (e.g., user actions with respect to the CGM system), purchase history data (e.g., user purchases of components of the CGM system), complaint data (e.g., negative user communications regarding the CGM system), and payment data (e.g., user payments for components of the CGM system). It is to be appreciated, therefore, that the additional data may include a variety of different data types collected from a variety of different sources. Moreover, the additional data, in some cases, may include both data describing multiple users in a user population (e.g., socioeconomic data or environmental data applicable to users in a particular country, state, city, or zip code) as well as data that is personalized to specific users (e.g., physiological data and behavioral data for a specific user).

In addition to identifying different states from this data describing the user population 110, the multi-state engagement system 318 is also configured to determine which of these identified states correspond to a particular user at a given time, such as determining that a user is a patient and currently in an erratic use stage with the CGM system 104. The multi-state engagement system 318 may determine such states by providing data (e.g., a feature vector) describing the user as input to the machine learning models and receive output from these models indicating the one or more states.

The multi-state engagement system 318 not only may determine which states correspond to a user at a given time but also may detect when a user transitions between states, e.g., when a user transitions from an active use stage to an erratic use stage. Based on determining which state corresponds to a user and/or detecting transitions between states, the multi-state engagement system 318 can generate notifications indicative of the states and/or state changes, and communicate the notifications to a predetermined recipient, e.g., to a patient, to a caregiver, to a health care provider, to a customer service representative for intervention, and so forth. Determined user state and/or state transition can also be used to customize delivery of at least one of the prediction 320 or the recommendation 322. In the context of generating one or more predictions which serve as a basis for the recommendation 322, consider the following discussion of FIG. 4.

Figure 4:
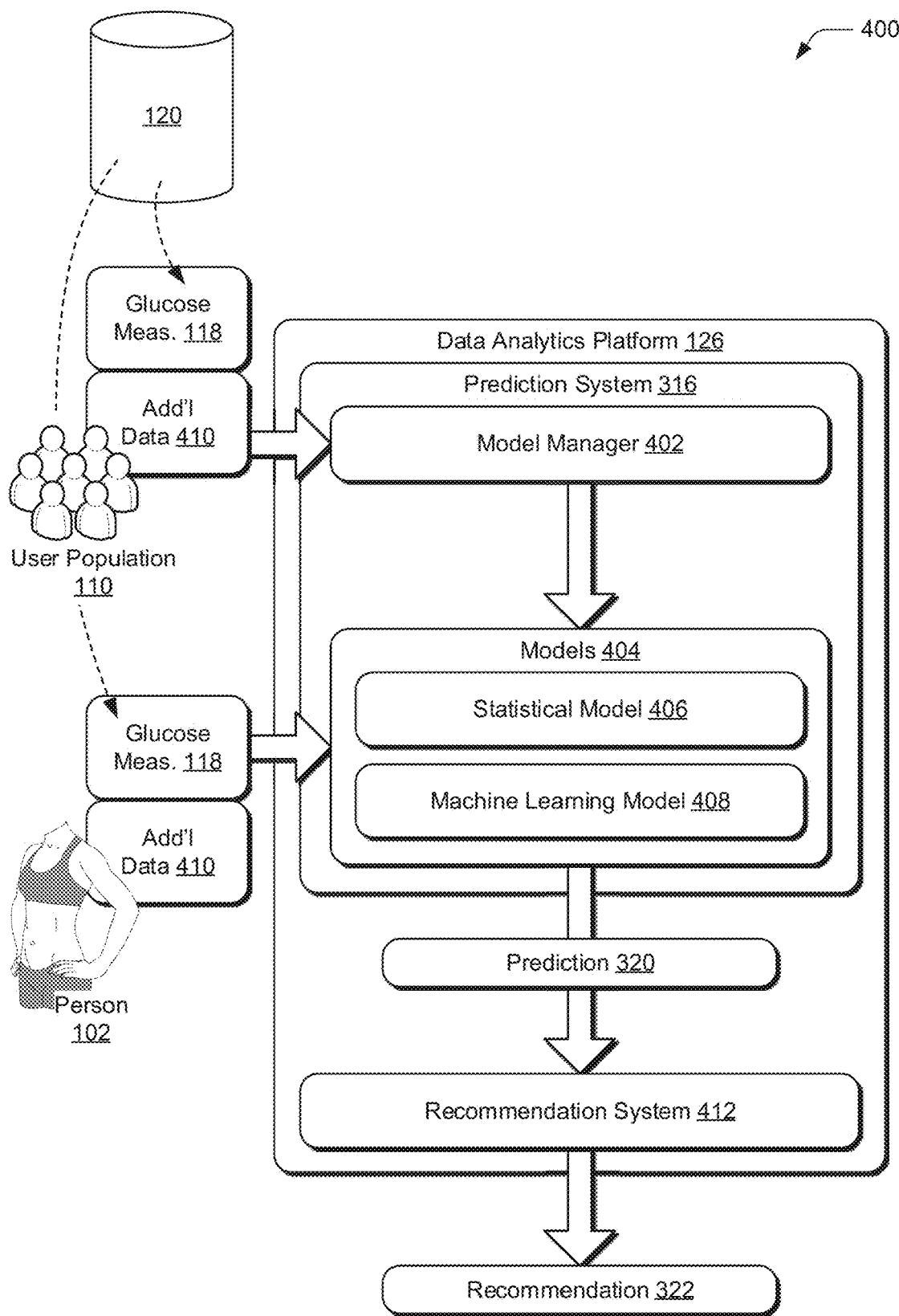
FIG. 4 depicts an example implementation of the prediction system of FIG. 3 in greater detail.

FIG. 4 depicts an example implementation 400 of the prediction system 316 in greater detail. As in FIG. 3, the prediction system 316 is included as part of the data analytics platform 126, although in other scenarios the prediction system 316 may also or alternately be, in part or entirely, included in other devices such as the computing device 108.

In the illustrated example 400, the prediction system 316 includes model manager 402, which manages models 404, including a statistical model 406 and an additional machine learning model 408, e.g., a neural network. It is to be appreciated that the models 404 may include different models without departing from the spirit or scope of the described techniques, such as multiple, different statistical models, multiple machine learning models configured as neural network, and/or multiple other types of machine learning models. These different machine learning models may be built or trained (or the model otherwise learned), respectively, using different data, according to different statistical modeling techniques, having different architectures, according to different algorithms, and so on. Accordingly, it is to be appreciated that the following discussion of the model manager 402's functionality is applicable to a variety of machine learning models. For explanatory purposes, however, the functionality of the model manager 402 will be described generally in relation to the statistical model 406 and the additional machine learning model 408.

In general, the model manager 402 is configured to manage the models 404. This model management includes, for example, building the statistical model 406, building the machine learning model 408, training the machine learning model 408, updating these models, and so on. Specifically, the model manager 402 is configured to carry out this model management using, at least in part, the wealth of data maintained in the storage device 120 of the CGM platform 112. As illustrated, this data includes the glucose measurements 118 and additional data 410 of the user population 110. Said another way, the model manager 402 builds the statistical model 406, builds the machine learning model 408, trains the machine learning model 408 (or otherwise learns a policy deployed by it), and updates these models using the glucose measurements 118 and the additional data 410 of the user population 110.

Generally, the CGM platform 112 obtains the additional data 410 of the user population from various devices, sensors, applications, or services. Thus, the additional data may be obtained from one or more "sources" that are different from the CGM system 104 from which the glucose measurements 118 are detected. In one or more implementations, this additional data 410 may include at least one or more portions of the CGM device data 214 additional to the glucose measurements 118 (e.g., the sensor identification 216 and sensor status 218 data), the supplemental data 304, the third party data 314, data from the IoT 114, and so forth.

The additional data 410 may include, by way of example and not limitation, health-related data, application interaction data, environmental data, demographic data, device data in addition to the glucose measurements (e.g., sensor identification data, incident reports), supplemental data added by the computing device, third party data, and so forth. Health-related data may include activity data (e.g., steps, exercise frequency, sleep data), biometric data (e.g., insulin level, ketone levels, heart rate, temperature, stress, temperature), nutrition data (e.g., food and drink logs, scanned restaurant receipts, carb consumption, fasting), medical records (e.g., A1C, cholesterol, electrocardiogram results, and data related to other medical tests or history), to name just a few. Application interaction data may include data extracted from application logs describing user interactions with a particular applications, clickstream data describing clicks, taps, and presses performed in relation to input/output interfaces of the computing device, gaze data describing where a user is looking (e.g., in relation to a display device associated with the computing device or when the user is looking away from the device), voice data describing audible commands and other spoken phrases of the user or other users (e.g., including passively listening to users), and so forth. Environmental data may include data describing various environmental aspects associated with the user, such as the user's location, a temperature and/or weather at the user's location, altitude of the user, barometric pressure, and so forth. Demographic data may include data describing the user, such as age, sex, height, weight, and so forth. The above-discussed types of the additional data are merely examples and the additional data may include more, fewer, or different types of data without departing from the spirit or scope of the techniques described herein.

Unlike conventional systems, the CGM platform 112 stores (e.g., in the storage device 120) or otherwise has access to glucose measurements 118 obtained using the CGM system 104 for hundreds of thousands of users of the user population 110 (e.g., 500,000 or more). Moreover, these measurements are taken by sensors of the CGM system 104 at a continuous rate. As a result, the glucose measurements 118 available to the model manager 402 for model building and training numbers in the millions, or even billions. With such a robust amount of data, the model manager 402 can build and train the models 404 to accurately mimic real-life effects of different behaviors on glucose levels. Absent the robustness of the CGM platform 112's glucose measurements 118, conventional systems simply cannot build or train models to cover state spaces in a manner that suitably represents how various behaviors affect glucose levels. Failure to suitably cover these state spaces can result in glucose predictions or predictions of other health indicators that are inaccurate, which can lead to recommending unsafe actions or behaviors that could cause death. Given the gravity of generating inaccurate predictions, it is important to build models 404 using an amount of glucose measurements 118 that is robust against rare events.

In one or more implementations, the model manager 402 builds the statistical model 406 by extracting from the glucose measurements 118 and the additional data 410 observed values corresponding to at least one attribute. Once built, the statistical model 406 is configured to predict values of this at least one attribute and output them—values of the at least one attribute do not serve as input to the model. In scenarios where the statistical model 406 is a regression model, for instance, these values may correspond to one or more dependent variables of the statistical model 406. The values of these attributes—corresponding to the statistical model 406's dependent variables—may be referred to as a first set of values in the following discussion. Also, the model manager 402 extracts from the glucose measurements 118 and the additional data 410 observed values corresponding to at least one other attribute. Once built, values of this at least one other attribute are to serve as input to the statistical model 406, e.g., as a vector of such values. In scenarios where the statistical model 406 is a regression model, the at least one other attribute may correspond to one or more explanatory (or independent) variables. The extracted values of these independent variables may be referred to as a second set of values in the following discussion.

Given the first set of values and the second set of values, the model manager 402 uses one or more known approaches for "fitting" these values to an equation so that it produces values of the first set from the values of the second set within some tolerance. Examples of such fitting approaches include using a least squares approach, using a least absolute deviations regression, minimizing a penalized version of the least squares cost function (e.g., ridge regression or lasso), and so forth. By "fitting" it is meant that the model manager 402 estimates model parameters for the equation using the one or more approaches and these sets of data. The estimated parameters include, for instance, weights to apply to values of the independent variables when the values are input to the statistical model 406 during operation. The model manager 402 incorporates these parameters estimated from the observed values into the equation to generate the statistical model 406. In operation, the prediction system 316 inputs values of the independent variables into the statistical model 406 (e.g., as one or more vectors or a matrix), the statistical model 406 applies the estimated weights to these input values, and then outputs values for the one or more dependent variables. This output is represented as prediction 320.

In one statistical-model building scenario, the model manager 402 uses the glucose measurements 118 of the user population 110 having timestamps before a particular timestamp and also uses corresponding additional data 410 (e.g., with timestamps that correspond to the glucose measurements 118 and are associated with users corresponding to the glucose measurements) as values of the independent variables for the statistical model 406. In this scenario, the model manager 402 may use the glucose measurements 118 of the user population 110 having timestamps after the particular timestamp as values of the dependent variables for the statistical model 406. Here, the model manager 402 uses one or more known approaches for fitting an equation to the pre- and post-timestamp data. In so doing, the model manager 402 estimates parameters of the equation so that by inputting the pre-timestamp data values, the post-timestamp glucose measurements 118 (or values within some tolerance of those measurements) are output.

The model manager 402 then incorporates the estimated parameters into the equation and persists this incorporation as the statistical model 406, such that the statistical model 406 preserves the estimated parameters with the equation. In this way, the model manager 402 builds a statistical model 406 capable of generating a prediction 320 of glucose measurements after a particular time when it receives as input glucose measurements before the particular time and also corresponding additional data. In operation and continuing with this scenario, the prediction system 316 may thus obtain a subset of the glucose measurements 118 of the person 102 before a particular time (e.g., a current time) along with the additional data 410 of the person 102 that corresponds to the independent variable used to train the statistical model 406. The prediction system 316 may then provide this data of the person 102 to the statistical model 406 as input. In the continuing scenario, the statistical model 406 generates the prediction 320 as glucose measurements of the person 102 after the particular time, e.g., the current time.

Although prediction of glucose measurements after a particular time (e.g., a current time) is discussed in relation to building and actually using the statistical model 406, the model manager 402 may build the statistical model 406 to predict different aspects from patterns in the observed glucose measurements 118 and additional data 410. By way of example, the model manager 402 may build the statistical model 406 to predict upward or downward trends in health indicators of the person 102, maintained health indicators of the person 102 over some period of time, and so forth—and use the glucose measurements 118 and the additional data 410 of the user population 110 to build the model to persist correlations with these health indicators and trends among the user population 110.

Returning now to a discussion of the additional machine learning model 408 (e.g., configured as a neural network) in accordance with the described techniques. In a similar manner as with the statistical model 406, the model manager 402 extracts a first set of observed values corresponding to at least one attribute and a second set of the values corresponding to at least one other attribute—both sets extracted from the glucose measurements 118 and the additional data 410 of the user population 110. The model manager 402 uses these sets of values to train the machine learning model 408 or provide feedback to the machine learning model 408 about its predictions so that it learns a policy for generating the predictions.

Also similar to the statistical model 406, once the additional machine learning model 408 is trained or learns at least an initial policy to deploy, the machine learning model 408 is configured to predict values of the at least one attribute corresponding to the first set and output those values. Further, the machine learning model 408, once trained or used to deploy at least an initial policy, is configured to receive values of the at least one other attribute of the second set as input, e.g., as a vector of such values. In scenarios where the machine learning model 408 is a neural network, for instance, the machine learning model 408 during operation may thus receive as input one or more vectors (e.g., feature vectors) that represent values of the at least one other attribute. In such scenarios, the machine learning model 408 during operation may also output one or more vectors (e.g., feature vectors) that represent values of the at least one attribute.

In the context of training, the model manager 402 may train the machine learning model 408 by providing an instance of data from the second set of values as input to the machine learning model 408. Responsive to this, the machine learning model generates the prediction 320, e.g., a prediction of a value for the at least one attribute corresponding to the first set. The model manager 402 obtains this training prediction from the machine learning model 408 as output and compares the training prediction to the actual extracted value of the first set that corresponds to the instance of data input. By way of example, the model manager 402 compares the training prediction to the actual extracted value using a cost function. Based on this comparison, the model manager 402 adjusts internal weights of the machine learning model 408 so that the machine learning model can substantially reproduce the actual extracted value when the instance of data is provided as input in the future.

This process of inputting instances of observed data into the machine learning model 408, receiving training predictions from the machine learning model 408, comparing the training predictions to expected output values (observed) that correspond to the input instances (e.g., using a cost function), and adjusting internal weights of the machine learning model 408 based on these comparisons, can be repeated for hundreds, thousands, or even millions of iterations—using an instance of training data per iteration.

The model manager 402 may perform such iterations until the machine learning model 408 is able to generate predictions 320 that consistently and substantially match an expected output, e.g., that substantially match the observed values of the first set of data. The capability of a machine learning model to consistently generate predictions that substantially match an expected output may be referred to as "convergence." Given this, it may be said that the model manger 402 trains the machine learning model 408 until it "converges" on a solution, e.g., the internal weights of the model have been suitably adjusted due to training iterations so that the model consistently generates predictions that substantially match expected output.

It is to be appreciated that this is just one additional example of a machine learning model 408 and how it may be trained. Indeed, machine learning models may be configured according to various paradigms (e.g., supervised learning, unsupervised learning, reinforcement learning, and so on) and trained using different approaches without departing from the spirit or scope of the described techniques. By way of example, the machine learning model 408 may be initially trained on the glucose measurements 118 and the additional data 410 of the user population and then the training may be further updated using training instances from the glucose measurements 118 and the additional data 410 of the person 102, e.g., to further tune various parameters of the machine learning model 408

Regardless, once the machine learning model 408 is trained using, at least in part, the glucose measurements 118 and the additional data 410 of the user population 110, the machine learning model 408 may be used in operation to generate the predictions 320 for a user corresponding to the person 102. Consider the following implementation example, which parallels the above-discussed statistical-model building scenario and use, but instead of leveraging the statistical model 406 leverages the machine learning model 408.

In this machine learning example, the model manager 402 uses the glucose measurements 118 of the user population 110 which have timestamps before a particular timestamp and also uses corresponding additional data 410 (e.g., with timestamps that correspond to the glucose measurements 118 and are associated with users corresponding to the glucose measurements) as training input to the machine learning model 408. In this scenario, the model manager 402 may use the glucose measurements 118 of the user population 110 which have timestamps after the particular timestamp as expected output (target or label) of the machine learning model 408. Here, the model manager 402 uses one or more known approaches for adjusting parameters of the model to predict the post-timestamp data given the pre-timestamp data as input. Examples of these approaches include supervised learning approaches such as gradient descent, stochastic gradient descent, and so on. Certainly, other approaches may be used without departing from the spirit or scope of the described techniques.

By using these approaches, the model manager 402 adjusts internal weights of the machine learning model 408 so that by inputting the pre-timestamp data values, the post-timestamp glucose measurements 118 (or values within some tolerance of those measurements) are output. Further, the machine learning model 408 preserves these internal weights, e.g., in connection with particular nodes of the model. In this way, the model manager 402 builds a machine learning model 408 capable of generating a prediction 320 of glucose measurements after a particular time when it receives as input glucose measurements before the particular time and also corresponding additional data.

In operation and continuing with this scenario, the prediction system 316 may thus obtain a subset of the glucose measurements 118 of the person 102 before a particular time (e.g., a current time) along with the additional data 410 of the person 102 that corresponds to the input data used to train the machine learning model 408. The prediction system 316 may then provide this data of the person 102 to the machine learning model 408 as input. In the continuing scenario, the machine learning model 408 generates the prediction 320 as glucose measurements of the person 102 after the particular time, e.g., the current time. In one or more implementations, the machine learning model 408 outputs this prediction in the form of a vector.

Although prediction of glucose measurements after a particular time (e.g., a current time) is discussed in relation to training and actually using the machine learning model 408, the model manager 402 may build the machine learning model 408 to predict different aspects from patterns in the observed glucose measurements 118 and additional data 410. By way of example, the model manager 402 may build the machine learning model 408 to predict upward or downward trends in health indicators of the person 102, maintained health indicators of the person 102 over some period of time, and so forth—and use the glucose measurements 118 and the additional data 410 of the user population 110 to build the model to persist correlations with these health indicators and trends among the user population 110. Due, in part, to training the machine learning model 408 with vast amounts of training data, the machine learning model 408 is capable of capturing latent features in the data, which may include hidden relationships and spurious correlations within the data, which are virtually impossible for human analysts to uncover absent them randomly happening upon the relationship.

Regardless of whether the statistical model 406, the additional machine learning model 408, or some combination (ensemble) of statistical and/or additional machine learning models is used to generate the prediction 320, it may be obtained by the recommendation system 412. The recommendation system 412 is configured to generate the recommendation 322 based on the prediction 320. The recommendation system 412 may be implemented using, or otherwise have access, to logic, which configures the recommendation 322 according to the prediction. By way of example, if the prediction 320 indicates a positive health trend for the person 102 (e.g., her A1C is lower), the recommendation system 412 can generate the recommendation 322 to recommend continuing various behaviors.

The logic used by the recommendation system 412 to generate the recommendation 322 may vary in complexity without departing from the spirit or scope of the described techniques, such as from a heuristic manually coded to one or more additional machine learning models for configuring recommendations based on receiving the prediction 320 as input. Further implementation examples of the types of predictions and recommendations that may be produced by the models 404 and the recommendation system 412, respectively, are discussed in further detail below. Now, though, consider the following discussion of FIG. 5 in relation to a validation service and decision support platform in accordance with the described techniques.

Figure 5:
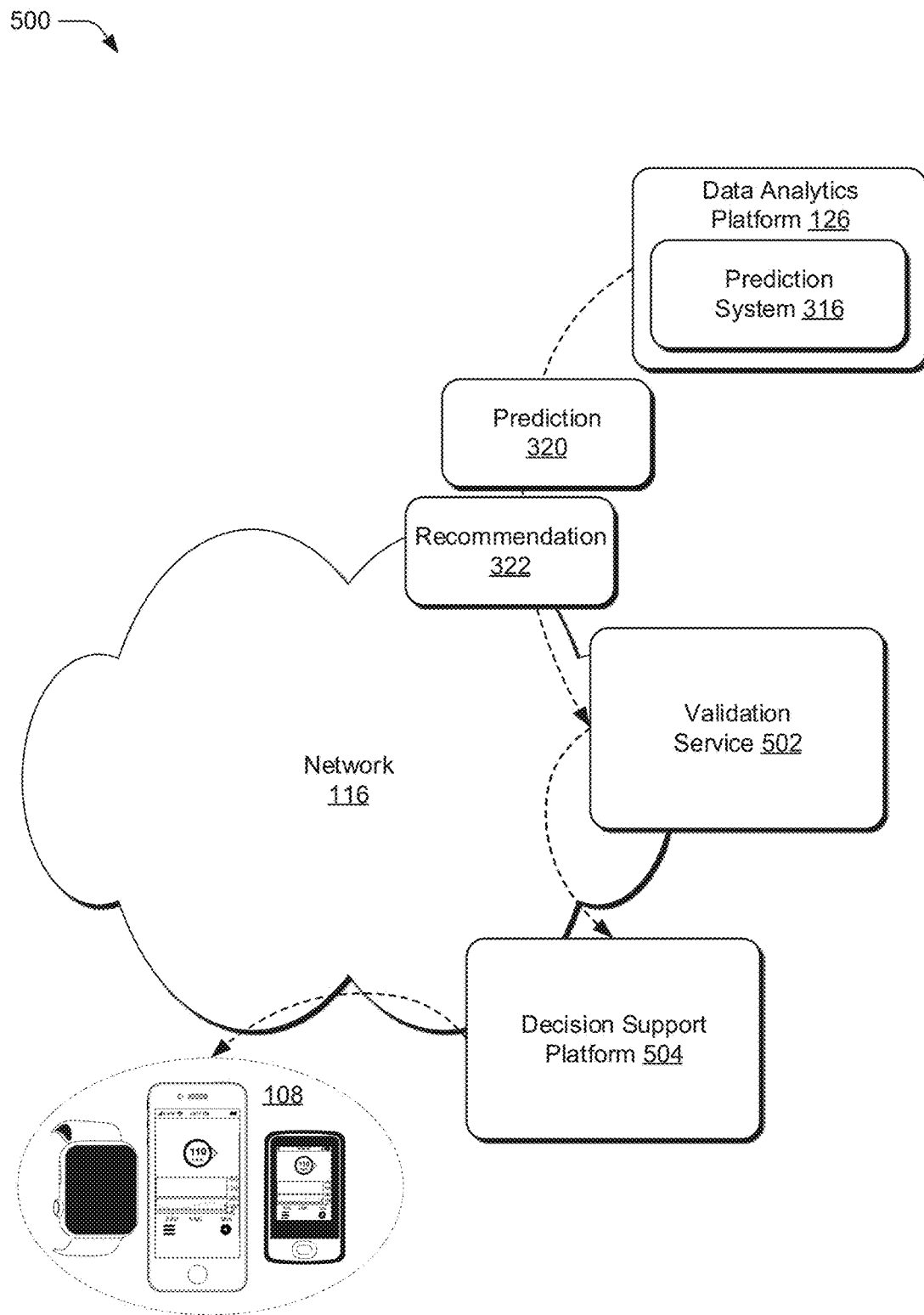
FIG. 5 depicts an example of an implementation in which at least one of predictions or recommendations produced by the data analytics platform are routed to at least one of a validation service or decision support platform.

FIG. 5 depicts an example 500 of an implementation in which at least one of predictions or recommendations produced by the data analytics platform are routed to at least one of a validation service or decision support platform.

The illustrated example 500 includes the computing device 108 and the data analytics platform 126 having the prediction system 316. In this example 500, the data analytics platform 126 is depicted communicating the prediction 320 and the recommendation 322. Here, the recommendation 322 relates to a user of the computing device 108, e.g., the person 102. By way of example, the prediction 320 includes information about the person (e.g., a predicted glucose level over an upcoming time period, a predicted health trend over an upcoming time period, and so on), and the recommendation 322 includes one or more suggestions intended for the user (e.g., one or more actions to perform or to eliminate, behaviors to adopt or eliminate, and so on).

In contrast to the illustrated example 300 of FIG. 3, the illustrated example 500 includes a validation service 502 and a decision support platform 504 as intermediaries between the data analytics platform 126 and the computing device 108. Accordingly, the prediction 320 and/or the recommendation 322 may be routed to either one or both of the validation service 502 or the decision support platform 504. Although the validation service 502 and the decision support platform 504 are not depicted in FIG. 3 it is to be appreciated that the predictions 320 and recommendations 322 generated in scenarios discussed in relation to FIG. 3 may also be routed through the validation service 502 and/or the decision support platform 504.

In accordance with the described techniques, the validation service 502 is configured to validate the recommendation 322. This means determining whether the recommendation is valid (e.g., safe) and can be further communicated to the decision support platform 504 and/or directly to the computing device 108. The validation service 502 may expose the recommendation 322 to a user that has been authenticated by the validation service 502 as authorized to validate recommendations, e.g., a clinician. By way of example, the validation service 502 may email the recommendation 322 to the clinician, provide the recommendation 322 through a clinician portal (e.g., where the clinician can review multiple recommendations and validate them or not), provide a notification of the recommendation 322 on a screen of a mobile device—allowing the clinician to approve, decline, or obtain additional information with mere gestures, just to name a few. The validation service 502 may surface recommendations to users that are allowed to validate the recommendations (e.g., clinicians) in a variety of ways without departing from the spirit or scope of the techniques described herein.

Responsive to a recommendation being validated (e.g., by a clinician or logic of the validation service 502), the recommendation may be further routed to the decision support platform 504 or directly to the computing device 108. When a recommendation is not validated (i.e., it is rejected), the recommendation may not be further routed to the decision support platform 504 or to the computing device 108. Instead, the validation service 502 may modify the recommendation (e.g., according to clinician input) and/or provide a notification back to the data analytics platform 126 that the recommendation is not validated. In this scenario, the data analytics platform 126 may be able to add an indication of non-validation as input to the prediction system and initiate generation of a different prediction 320 and/or recommendation 322.

Indeed, the models 404 may be updated based on validations and non-validations received from the validation service 502. In scenarios where the validation service 502 validates the recommendation 322 and consequently allows the recommendation 322 to be forwarded directly to the computing device 108, the computing device 108 may output the recommendation 322, such as via a display device, via an audio device (e.g., speakers, headphones, ear buds), via tactile feedback, and so on, as described above and below. An example of how recommendations may be surfaced by the validation service 502 to users that are allowed to validate recommendations (e.g., clinicians) is discussed in more detail below in relation to FIG. 13.

As mentioned above, the prediction 320 and/or the recommendation 322 may be communicated to the decision support platform 504 by the validation service 502 or alternately may be communicated to the decision support platform 504 directly from the data analytics platform 126, bypassing the validation service 502. The decision support platform 504 is configured to provide support to users of the CGM platform 112 for managing one or more health conditions, e.g., diabetes. Responsive to receiving the recommendation 322, for example, the decision support platform 504 may provide the recommendation to a customer support specialist, e.g., via email, a support-specialist portal, and so on.

Based on the recommendation 322, as well as based on other information accessible about the corresponding user, the customer service specialist may determine how to support the user. By way of example, the customer service specialist may determine to call the user to provide voice support during a phone call, to select (e.g., via a support-specialist portal) one or more pre-configured messages to send to the user (e.g., text message, mobile phone notifications, email messages, and so on), to build one or more messages to send to the user from pre-configured message components, to simply forward the recommendation 322 to the computing device 108, to contact a clinician or other medical professional associated with the user, to contact emergency services, to contact a caregiver or other guardian (e.g., parent) of the user, and so forth. The decision support platform 504 may provide tools, content, and services for supporting users' management of their health conditions based on the prediction 320 and the recommendation 322 in a variety of ways without departing from the spirit or scope of the described techniques.

Figure 6:
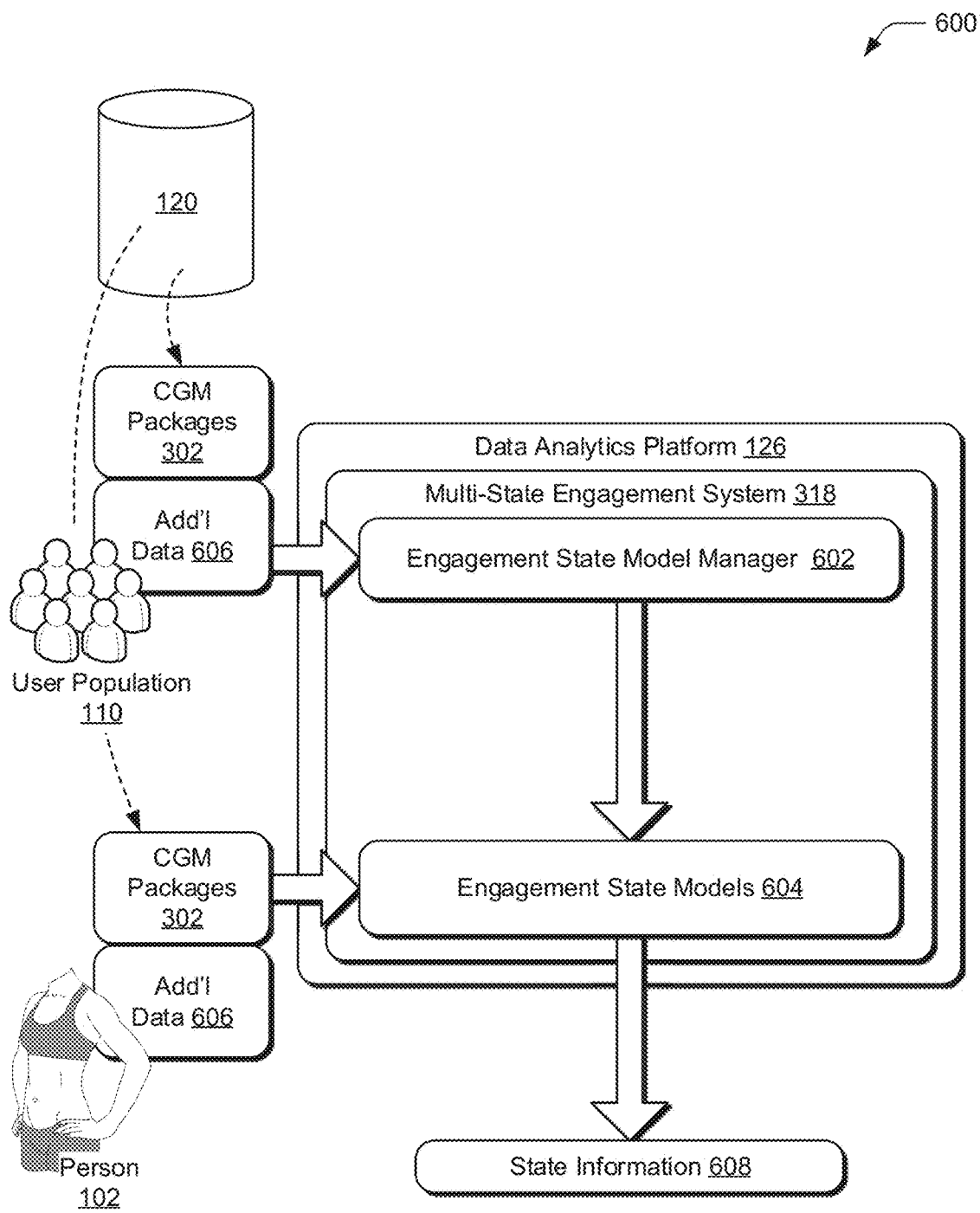
FIG. 6 depicts an example implementation of the multi-state engagement system of FIG. 3 in greater detail.

FIG. 6 depicts an example implementation 600 of the multi-state engagement system 318 in greater detail. As in FIG. 3, the multi-state engagement system 318 is included as part of the data analytics platform 126, although in other scenarios the multi-state engagement system 318 may also or alternately be, in part or entirely, included in other devices such as the computing device 108.

In the illustrated example 600, the multi-state engagement system 318 includes engagement state model manager 602 and engagement state models 604, which may include one or more of a variety of machine learning models, e.g., classifiers, autoencoders, neural networks, decision trees, logistic regression models, Markov models, reinforcement learning models, to name just a few. These various machine learning models and/or various ensembles of machine learning models may be built or trained (or the model otherwise learned), using different data, according to different statistical modeling techniques, having different architectures, according to different algorithms, and so on. Accordingly, it is to be appreciated that the following discussion of the engagement state model manager 602's functionality is applicable to a variety of machine learning models.

In general, the engagement state model manager 602 is configured to manage the engagement state models 604. This model management includes, for example, generating the engagement state models 604, such as by training one or more models (e.g., neural networks), providing data to one or more of the models to enable them to identify patterns in the data indicative of different states, deploying an initial policy for identifying different states and then updating the policy as feedback is received regarding output of one or more models (e.g., reinforcement learning models), updating these models, and so on. Specifically, the engagement state model manager 602 is configured to carry out this model management using, at least in part, the wealth of data maintained in the storage device 120 of the CGM platform 112. As illustrated, this data includes the CGM packages 302 (or at least portions of them) and additional data 606 of the user population 110. Said another way, the engagement state model manager 602 builds the engagement state models 604, trains the engagement state models 604 (or otherwise learns data patterns indicative of multiple, different states of engagement), and updates these models using the CGM packages 302 and the additional data 606 of the user population 110. It is to be appreciated that the additional data 606 may correspond to the additional data 410 in one or more implementations. Alternately, the additional data 606 may describe aspects of the user population 110 that differ, entirely or just in part, from those described by the additional data 410.

In a similar fashion as the additional data 410, the CGM platform obtains the additional data 606 of the user population 110 from various devices, sensors, applications, or services. Thus, the additional data 606 may be obtained from one or more "sources" that are different from the CGM packages 302. This additional data 606 may include, by way of example and not limitation, purchase history data (e.g., describing purchases of the CGM systems 104, portions thereof (e.g., disposable sensor application assemblies), and/or services provided by the CGM platform 112), complaint data, customer service data (e.g., describing user interactions with customer service representatives such as whether a user responds to an attempt by a customer service representative to contact the user), physiological data, socioeconomic data, attitudinal data, behavioral data, purchase history, complaint data, and payment data.

The additional data 606 may also include data describing health-related online activity of the user population 110, such as data describing search queries related to health conditions (e.g., search queries for "urination," "high blood sugar," "diabetes," "thirsty," names of glucose monitoring systems, and so on), data describing navigation to health- or diabetes-related websites, data describing interactions with health-related mobile applications, data describing social networking interactions with health-related profiles on one or more social networks (e.g., following users, hashtags, liking posts, commenting), data describing health-related social networking interactions (e.g., posts or comments) on one or more social networks, and so forth.

Unlike conventional systems, the CGM platform 112 stores (e.g., in the storage device 120) or otherwise has access to CGM packages 302 for hundreds of thousands of users of the user population 110 (e.g., 500,000 or more). Moreover, the CGM measurements 118 included in these CGM packages 302 are taken by sensors of the CGM system 104 at a continuous rate. As a result, the glucose measurements 118, and the data describing these measurements (e.g., the CGM packages 302), available to the engagement state model manager 602 for building and training machine learning models amounts to millions, or even billions of data points. With such a robust amount of data, the model manager 402 can build and train the engagement state models 604 to accurately identify multiple, different states of engagement by the user population 110 with the CGM system 104 and the CGM platform 112.

Absent the robustness of the CGM platform 112's glucose measurements 118—as well as data describing characteristics of these measurements and receipt by the CGM platform 112 of the CGM packages 302—conventional systems simply cannot build or train models to cover state spaces in a manner that suitably represents how users actually engage in the real world with the CGM system 104 and the CGM platform 112. Failure to suitably cover these state spaces can result in predicting states of use with the CGM system 104 and the CGM platform 112 that are inaccurate, which can lead to intervention that is too late (or is never carried out) to prevent potentially unsafe conditions with the CGM system 104 or prevent discontinued use of the CGM system 104 and the CGM platform 112. Given the gravity of inaccurately identifying states which indicate how users actually interact with the CGM system 104, it is important to build the engagement state models 604 using an amount of CGM packages 302 that is robust enough to capture patterns of any spurious correlations or hidden relationships in the data.

Broadly speaking, the engagement state model manager 602 generates the engagement state models 604 using the CGM packages 302 and the additional data 606. The engagement state model manager 602 may do so in various ways so that the engagement state models 604 in operation generate and output state information 608 that identifies one or more states to which an individual user (e.g., the person 102) corresponds at a given time. By way of example, the engagement state model manager 602 may generate the engagement state models 604 using supervised and/or unsupervised learning approaches.

In a supervised learning approach, for instance, the engagement state model manager 602 may generate training instances from the CGM packages 302 and the additional data 606 of the user population. Each of these instances may also be associated with one or more labels indicative of a state, where a given label is associated with instances having a common pattern in their data. Where CGM packages 302 are being received for a user but the amount received or frequency of receipt is less than some threshold over time, for example, a respective training instance may be associated with an 'erratic use' label. In such scenarios, the engagement state model manager 602 exposes the engagement state models 604 to the data of the instances and compares (e.g., using a cost function or other supervised learning algorithm) the state information 608 output during training to the labels associated with each of the training instances—the output state information 608 in this example may correspond to probabilities that the training instance's data corresponds to each available label. The engagement state model manager 602 then adjusts internal weights of the engagement state models 604 based on the comparison, e.g., according to the cost function or other supervised learning algorithm.

Alternately or in addition, training instances may be formed based on an observed behavior that corresponds to a particular state (e.g., discontinued use of the CGM system 104), such that data describing the behavior is extracted from the CGM packages 302 and the additional data 606 and also such that data describing other observed behaviors (e.g., occurring in time before the observed behavior) is extracted from the CGM packages 302 and the additional data 606. Here, the engagement state model manager 602 exposes the engagement state models 604 to instances comprising the data describing the other observed behaviors and compares (e.g., using a cost function or other supervised learning algorithm) the state information 608 output during training to the data describing the observed behavior of the respective instances. The output state information 608 in this example may correspond to a probability that the user associated with the training instance discontinues use of the CGM system 104 within some amount of time. The engagement state model manager 602 then adjusts internal weights of the engagement state models 604 based on the comparison. Although these two examples of supervised learning are described, it is to be appreciated that the engagement state model manager 602 may use a variety of supervised learning techniques to generate the engagement state models 604 so that they can identify multiple, different states of engagement with the CGM system 104 and the CGM platform 112 without departing from the spirit or scope of the described techniques.

In an unsupervised approach, the engagement state model manager 602 generates training instances from the CGM packages 302 and the additional data 606 of the user population 110. By way of example, the engagement state model manager 602 generates a number of feature vectors from the CGM packages 302 and the additional data 606 of the user population 110, where each feature vector corresponds to a user of the user population 110. Here, the features represent aspects described by the CGM packages 302 and the additional data 606. Each instance of training data for a particular model is configured to represent a same set of aspects (e.g., features) of the data, however, a value for a given aspect in one instance may vary from a value of the given aspect in another instance depending on how the aspect is described by the CGM packages 302 and the additional data 606 of a first and second user.

In such unsupervised approaches, the engagement state model manager 602 then exposes the generated training instances to the engagement state models 604. During training with an unsupervised approach, the engagement state models 604 identify patterns indicative of multiple, different states among the training instances (e.g., by grouping or otherwise segmenting the instances) according to respective algorithms Said another way, an unsupervised learning model, according to an algorithm with which it is implemented, learns an underlying model from the data and uses the underlying model to segment the training instances based on patterns observed in the data. Some example unsupervised learning approaches include, for instance, clustering (e.g., k-means), anomaly detection, and neural networks (e.g., autoencoders, Hebbian learning, generative adversarial networks), to name just a few.

In operation—whether configured as supervised, unsupervised, or reinforcement models—the engagement state models 604 receive as input data derived from the CGM packages 302 and the additional data 606 of the person 102, identify which of the one or more states correspond to the person 102 based on the input data, and output the state information 608 indicative of the identified states. By way of example, the state information 608 may be configured as one or more labels representing one or more identified states, probabilities that the person 102 corresponds to the different states (e.g., a first probability that the person 102 is in an active use stage, a second probability that the person 102 is in an erratic use stage, a third probability that the person 102 is in a discontinued use stage, and so on), indications of behaviors that are likely to cause other behaviors (e.g., indications of behaviors that are likely to cause the person 102 to discontinue use of the CGM system 104), indications that the person 102 is transitioning or has transitioned between states, and so forth. In one or more implementations, the state information 608 may include a Markov matrix, which visually conveys performance of a corresponding Markov model. It is to be appreciated that the state information 608 may describe a variety of aspects about the multiple, different states of engagement with the CGM system 104 without departing from the spirit or scope of the described techniques.

As discussed in more detail below, this state information 608 can be used to control communication with users of the CGM platform 112. For instance, when the state information 608 includes a probability—of the person 102 being in an erratic use stage at a current time—that is higher than a threshold probability, an intervention platform may deliver one or more communications to the person 102 and/or deliver them to a customer service representative, e.g., notifications alerting the representative of erratic use. In this way, the intervention platform may communicate with the person 102 (e.g., intervene) to determine if use of the CGM system 104 has actually become erratic (or there is some error causing the use to appear erratic), why use has become erratic, and provide information to cause use to return to the "active" level. The state information 608 may also be used to automatically customize the predictions 320 and/or the recommendations 322 communicated to the computing device 108. The multiple, different states, as identified by the state information 608, may be used in a variety of ways without departing from the spirit or scope of the techniques described herein. As one example of states that may be modeled by the engagement state models 604, consider the following discussion of FIG. 7.

Figure 7:
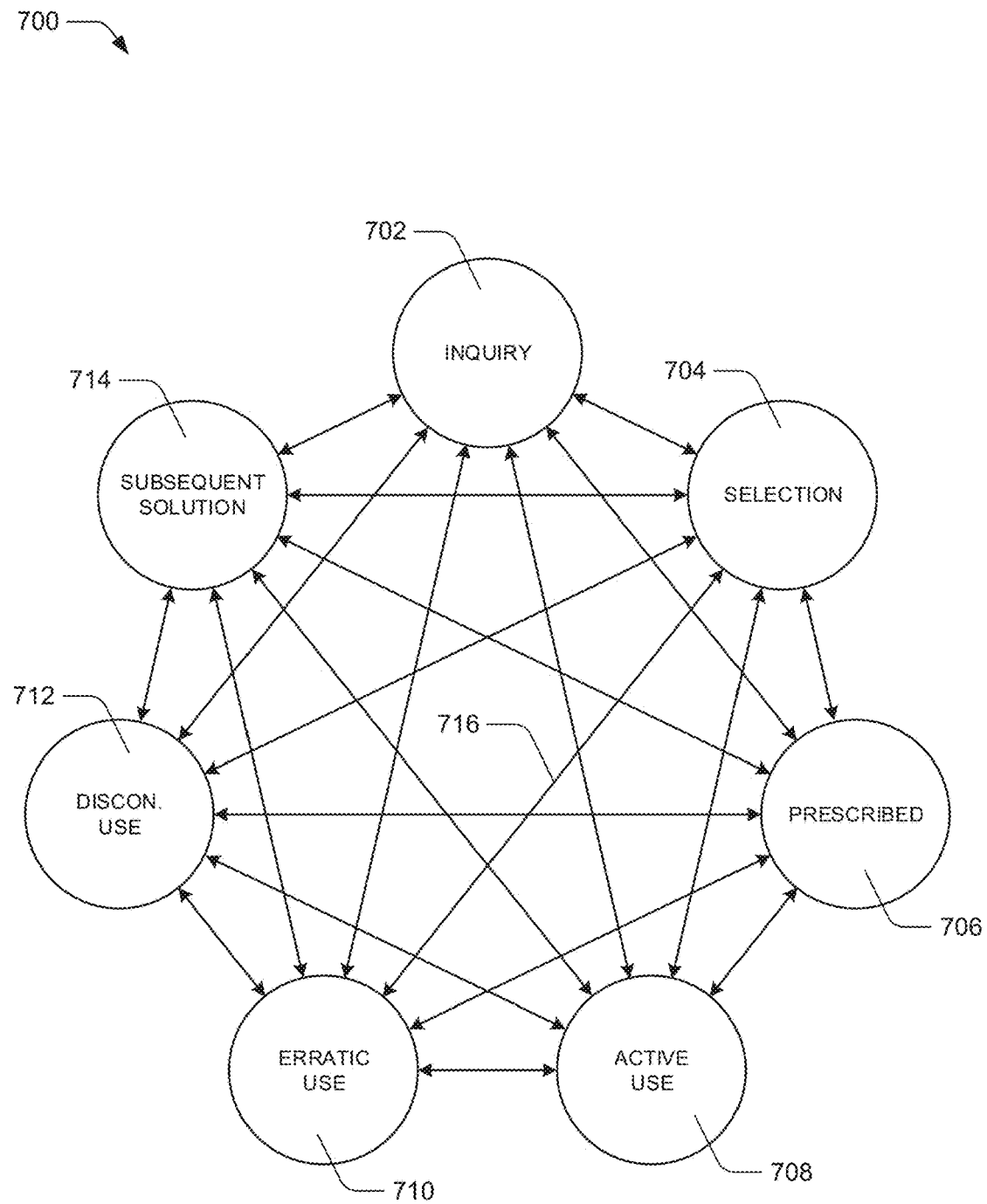
FIG. 7 depicts an example state space of multiple, different states of engagement with a CGM system.

FIG. 7 depicts an example state space 700 of multiple, different states of engagement with a CGM system.

The illustrated example 700 includes states 702, 704, 706, 708, 710, 712, 714. These states may represent a plurality of labels used in connection with training and using an engagement state model 604 configured as a classifier, such that the classifier predicts one of the classifications when given input data (e.g., a feature vector) describing aspects of the CGM packages 302 and the additional data 606 of the person 102. Alternately or additionally, the illustrated states 702, 704, 706, 708, 710, 712, 714 may represent a plurality of states learned by the engagement state models 604 using an unsupervised learning technique.

The illustrated example 700 also includes a plurality of edges representing transitions between the different states 702, 704, 706, 708, 710, 712, 714. It is to be appreciated that although the example 700 includes bidirectional edges between each state, in one or more implementations, there may be no transitions between certain states and/or transitions may only occur in one direction between certain states—not bi-directionally. Edge 716 is one example of these edges. Although the state space 700 is illustrated with these edges, the engagement state models 604 in operation may simply be configured to generate the state information 608 as probabilities of a user to transition from a current state to the different state or the probability that a user has already transitioned to a different state (through comparison with previously generated state information). The states may be modeled as distributions—not as vertices with edges.

In this example 700, the states 702, 704, 706, 708, 710, 712, 714 represent an example sequence of stages by which a user, that is a patient and may be prescribed the CGM system 104, may engage with the CGM system. Here, the state 702 represents an inquiry stage (e.g., where a user inquires about or otherwise demonstrates interest in the CGM system 104 or inquires about medical conditions related to diabetes), the state 704 represents a selection stage (e.g., where the user is actively selecting among glucose monitoring solutions), the state 706 represents a prescribed stage, the state 708 represents an active use stage (e.g., where the user actively uses the CGM system 104 along with functionality of the CGM platform 112), the state 710 represents an erratic use stage (e.g., where a user's activity level declines some amount from a previous active use level and/or drops below a threshold amount of use), the state 712 represents a discontinued use stage (e.g., where the user discontinues use of the CGM system 104 and/or the CGM platform 112), and the state 714 represents a subsequent solution stage (e.g., where the user uses a different CGM system deployed by an entity that is different from the CGM platform 112).

This is merely one example of multiple states in relation to which users may engage with the CGM system 104. Certainly, other states may be used and the engagement state models 604, using particular algorithms, may identify a variety of states (e.g., segments of users) indicative of how different users engage with the CGM system 104 and the CGM platform 112 without departing from the spirit or scope of the described techniques.

Figure 8:
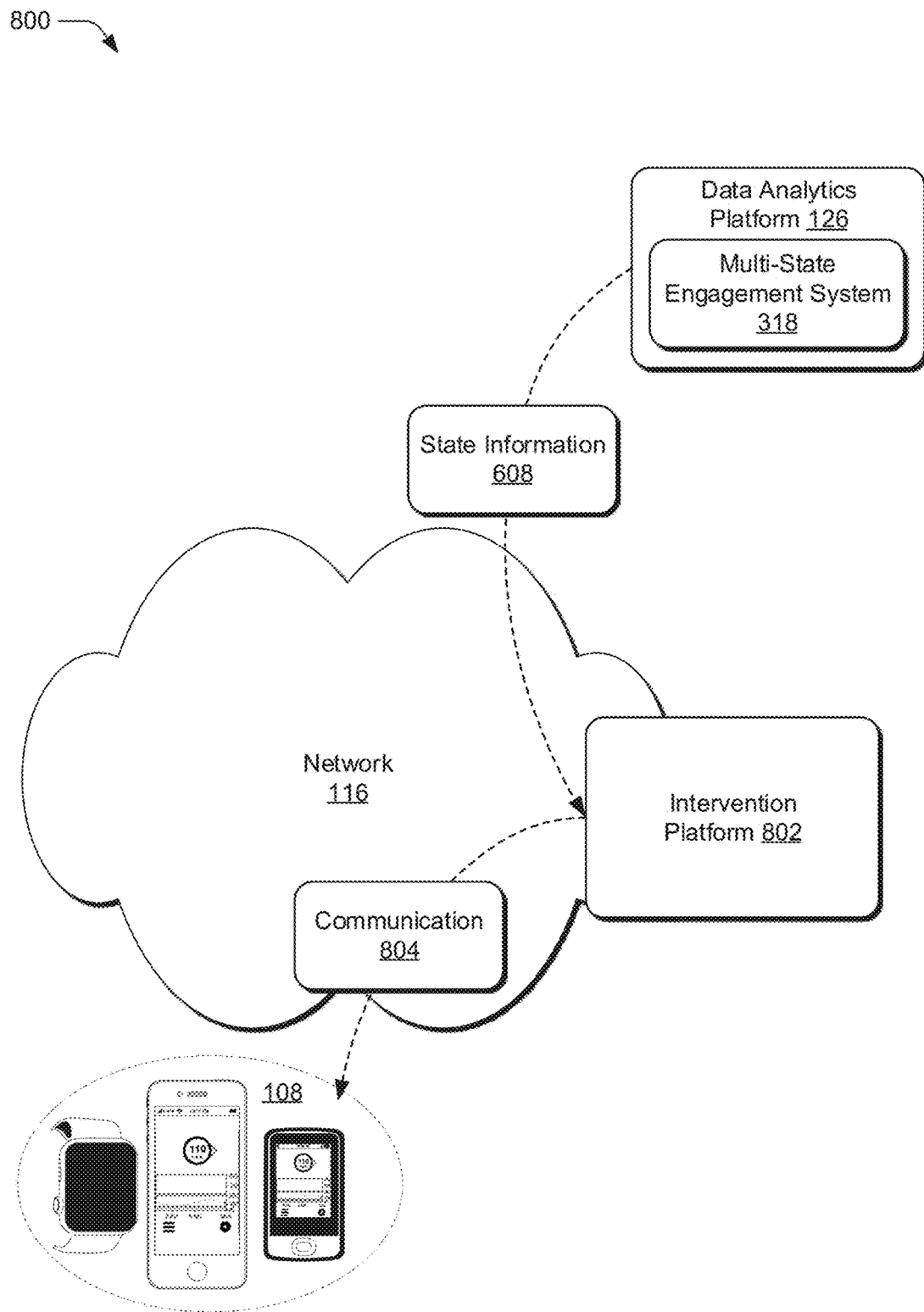
FIG. 8 depicts an example of an implementation in which information about state of engagement with a CGM system is routed to an intervention platform.

FIG. 8 depicts an example 800 of an implementation in which information about state of engagement with a CGM system is routed to an intervention platform.

The illustrated example 800 includes the computing device 108 and the data analytics platform 126 having the multi-state engagement system 318. In this example, the data analytics platform 126 is depicted communicating the state information 608 to the intervention platform 802.

In accordance with the described techniques, the intervention platform 802 is configured to communicate with a user associated with the computing device 108 based on the state information 608. By way of example, the state information 608 may include an indication of a stage of engagement with the CGM system 104 for the person 102. For instance, the state information 608 may include probabilities that the user is in each of a plurality of stages of interaction with the CGM system 104, where a current state may be identified as the stage with the highest probability. Additionally or alternately, the state information 608 may include a probability that a user transitions from a current state to a new state, along with driving factors predicted by the multi-state engagement system 318 as likely to drive the transition to the new state.

The intervention platform 802 may expose the state information 608 to a user that has been authenticated to the intervention platform 802 and authorized to intervene in certain scenarios by communicating with users, e.g., a customer service representative, clinician, and so forth. By way of example, the intervention platform 802 may provide the state information 608 (or notifications derived based on the state information 608) through an intervention portal, e.g., where a customer service representative can review state information for multiple users.

The exposed state information 608 may enable an authorized user of the intervention platform 802 to determine whether to communicate with a user associated with the state information 608 or not, such as whether to initiate a telephone call to the user, send an email to the user, send an SMS message to the user and so forth. Inclusion of the factors likely driving a predicted transition from a current state to a new state can also be used to customize strategies for intervention. By way of example, if the state information 608 indicates that faulty equipment (e.g., a faulty sensor 202) is being used and an amount of use has dropped since beginning use of the faulty equipment, a customer service representative may deploy a strategy specific to replacing the faulty equipment, e.g., sending new, properly working equipment. The intervention platform 802 may also expose tools via a user interface that enable its customer service representatives to communicate with users. Communication 804 represents a communication from the intervention platform 802 based on the state information 608. The communication 804 may be a telephone call, an email, an SMS message, an instant message, a mobile application notification, and so forth.

Although customer service representatives are discussed just above, in some implementations the state information 608 may not be exposed to a user of the intervention platform 802—such that the user decides whether and how to communicate with the user of the computing device 108. Instead, the intervention platform 802 may be configured to automatically generate and communicate the communication 804 based on the state information 608, such as according to logic that instructs the intervention platform 802 to communicate in particular ways depending on the state information 608. If the state information 608 indicates that a user transitions from an erratic use stage to an active use stage, for instance, the intervention platform 802 may automatically communicate a congratulatory SMS message to the computing device 108. It is to be appreciated that responsive to the state information 608, the intervention platform 802 may both automatically generate and send a personalized communication 804 to the computing device 108 and also expose the state information 608 (or information derived from it) via a user interface to a user (e.g., customer service representative of the intervention platform 802). The intervention platform 802 may provide tools, content, and services for initiating actions based on the state information 608 of a user in a variety of ways without departing from the spirit or scope of the described techniques.

Having discussed the CGM system 104 as well as how data collected from various sources is used to identify and predict multiple, different states of engagement with CGM systems, consider the following implementation examples.

Generating Predictions and Recommendations Using a Model

Figure 9:
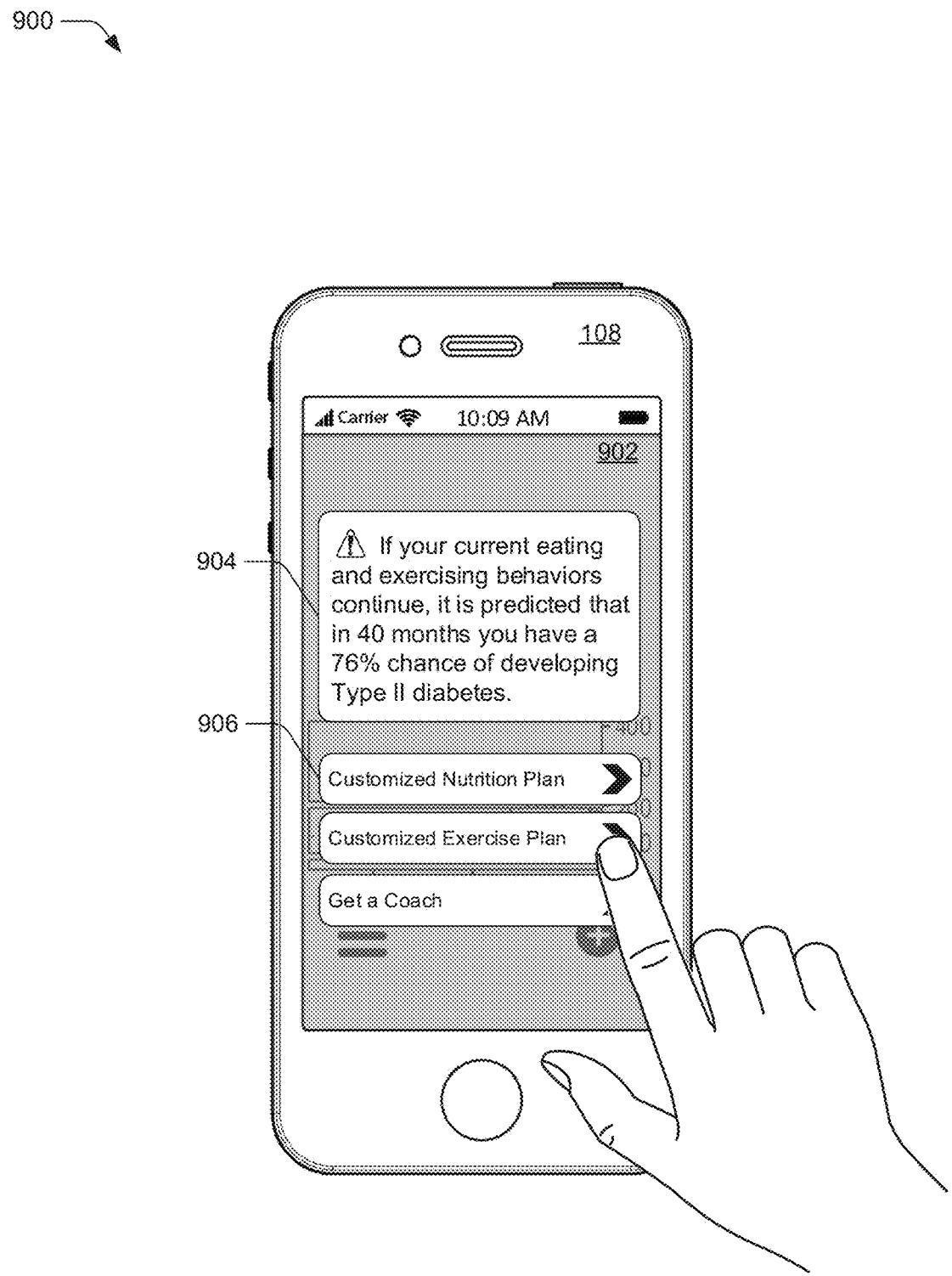
FIG. 9 depicts an example implementation of a user interface of the CGM platform displayed on a computing device coupled to a CGM system.

FIG. 9 depicts an example 900 of a user interface of the CGM platform displayed on a computing device coupled to a CGM system.

The illustrated example 900 includes a CGM user interface 902 displayed by the computing device 108. In this example, the CGM interface 902 is depicted as displaying a prediction 904 along with a recommendation 906. As described throughout, the prediction 904 is generated by the prediction system 316 to predict a health indicator of the user by processing the glucose measurements 118 and additional data 410 of a user using one or more models, such as statistical model 406 or additional machine learning model 408.

For purposes of this example, assume that a user begins using a CGM system 104 to measure glucose levels after receiving A1C and fasting glucose test results indicating that the user has "pre-diabetes," which puts the user at risk for developing Type II diabetes in the near future. In view of this, the user begins wearing the CGM system 104, which automatically provides the glucose measurements 118 to the prediction system 316. The CGM platform 112 processes the glucose measurements 118 collected for the user to determine that the user's blood glucose is increasingly in the "high" range (e.g., >250 mg/dl).

Along with the glucose measurements 118, the prediction system 316 obtains nutrition data of the user, such as food and drink purchase data provided by various third parties 306 (e.g., grocery stores, restaurants, liquor stores) and/or user provided nutrition data (e.g., food logs, captured images of foods and drinks consumed, scanned restaurant or grocery store receipts). This nutrition data indicates that, on average, the user consumes a one-liter bottle of soda each week, eats at fast food restaurants three times per week, and drinks beer and eats potato chips most weekends. The prediction system 316 may also make various inferences based on food or drinks which are not consumed by the user. In this case, the prediction system 316 analyzes the nutrition data to determine that the user rarely purchases "whole foods," such as fruit, vegetables, or meat. Additionally, the prediction system 316 obtains activity data for the user which includes steps data indicating that the user rarely walks more than 5,000 steps per day and does not work out, and also includes sleep data indicating that the user sleeps an average of just five hours each night.

The prediction system applies the models 404 to the glucose measurements 118 and the additional data 410, which in this example, includes the above-discussed nutrition data and activity data of the user. In view of the user's increasing blood glucose measurements, poor diet choices, and lack of activity, the prediction system 316 generates prediction 904 which indicates that the user has a 76% chances of developing Type II diabetes in 40 months.

Along with the prediction 904, the CGM user interface 902 displays recommendation 906 generated by the recommendation system 412 of the data analytics platform 126. The recommendation 906 includes one or more actions or behaviors that the user can take to improve the user's predicted negative health condition. In this case, the recommendation 906 includes a recommendation for a customized eating plan, a recommendation for a customized exercise plan, and a recommendation to get a coach that can help the user stay on track with the recommended nutrition and exercise plan. In FIG. 9, the user is shown selecting the customized exercise plan recommendation in order to obtain more detailed information regarding the recommended exercise plan.

Continuing with this example, assume that the user follows the actions and behaviors recommended by the prediction system 316, such as by switching to a whole food diet and tracking the diet using an online food log, walking 10,000 steps per day and tracking steps using a smart watch with a pedometer, and working out three times per week and logging each work out with an online workout log. In this case, the prediction system 316 continuously gathers the glucose measurements 118, nutrition data, and activity data for the user, and determines that the user's improved nutrition choices and exercise frequency is correlated with a decrease in the user's average blood glucose measurements 118.

Figure 10:
FIG. 10 depicts an example implementation of the user interface outputting an updated prediction and an updated recommendation.

Based on this continuous analysis of the user's updated glucose measurements 118 from the CGM sensor and the additional data 410 indicating the user is making better food choices (as indicated by the user's nutrition log) and exercising more frequently (as indicated by the steps data and exercise log), the prediction system 316 generates an updated prediction, which is communicated to the computing device 108 for display as a notification 1002 as shown in FIG. 10. In this example, the updated prediction of notification 1002 indicates that the user is now "unlikely" to develop Type II diabetes in the next 40 months. Notably, the updated prediction of notification 1002 provides positive feedback to the user, which may further incentivize the user to continue eating healthy and exercising. Conversely, in cases where an updated prediction indicates a worsening health condition, the updated prediction may be helpful motivation to get the user back on track.

Generating Application Recommendations for Similar Users

As described throughout, the CGM platform 112 leverages one or more CGM platform APIs 310 to enable the communication of glucose measurements 118 from the CGM platform 112 to various third parties 306, as well as the communication of third party data 314 from the third parties 306 to the CGM platform 112. Due to this, applications and services provided by such third parties 306 which leverage the glucose measurements 118 are increasingly becoming available and can often be downloaded via an "App Store". Once downloaded to computing device 108, the user can authorize the third party 306 to access the user's glucose measurements 118 via the CGM Platform API 310. Doing so enables third parties 306 to leverage the glucose measurements 118 in a variety of different ways to improve the user's health. In this way, third parties 306 may be able to provide various applications and services that use the glucose measurements 118, even though such third parties 306 may not manufacture and deploy their own CGM systems. As the number of third party "apps" and services increase, it becomes increasingly difficult for users of the population to discover the apps and services that would work best for their individual situation.

The CGM platform 112 may include an "ingress" API 310 which enables the CGM platform 112 to receive third party data 314 from the various third parties 306 (e.g., via third party servers of the third party 306). The third party data 314 may include application interaction data describing user interactions with third party services or applications. Such data, for example, may include data extracted from application logs describing user interactions with a particular applications, clickstream data describing clicks, taps, and presses performed in relation to input/output interfaces of the computing device, and so forth.

The CGM platform 112 can aggregate the application interaction data, along with the glucose measurements 118 and additional data in order to determine whether a user's interaction with a particular application or service correlates to improvement of the user's health. For example, based on the glucose measurements 118, the CGM platform 112 can objectively determine an improvement in a health condition of a user. The CGM platform 112 can consider a variety of different factors, based on the glucose measurements, when determining whether application usage improves a user's health, including improvements in average blood glucose level, time-in-range, mitigation of specific undesired patterns, or any combination thereof. Additionally, the CGM platform 112 may provide various controls to account for differences in the glucose measurements 118, such as sensor utilization and calibration frequency. The CGM platform 112 may also consider data provided by the third parties 306 when determining an improvement in a user's health. The CGM platform 112 can then correlate the improvement or decline in the user's health with usage of a particular application based on the application interaction data. For example, if the CGM platform 112 detects an improvement with the user's health that coincides with heavy usage of a particular application, then the CGM platform 112 may determine that the particular application is correlated with the improvement. Based on the amount of data available to the CGM platform 112, the correlation of a particular application with improvement in a health condition may be determined for a subset of users of the user population 110.

The recommendation system 412 can then identify a similar user having the health condition, and generate a recommendation to the similar user to utilize the particular application that helped to improve the health condition of the subset of similar users. To do so, the recommendation system 412 can predict a probability of a similar improvement in a health condition through usage of a particular application by other users in the user population and recommend applications with a high probability of improving health to other target users. Such application recommendations may be targeted to individual users who are similar to the subset of users with an improved health condition that correlates to the usage of the particular application. For instance, if use of a particular application is correlated with improving the glycemia of a subset of users in the user population, then the CGM platform 112 can recommend use of the particular application to similar users in the user population 110.

Identification of a similar user may be based on at least one of demographics or observed patterns in glucose measurements of the similar user. For example, a similar user may be identified as having a same health condition based, in part, on glucose measurements 118 provided by a CGM system 104 worn by the user. The CGM platform 112 may first generate a user profile for new users who begin wearing the CGM system 104 that includes demographic data, such as age, gender, location, existing medical records, and so forth. As the CGM platform 112 collects glucose measurements 118 and additional data 410 from the user, the CGM platform 112 refines the user's similarity scores with other users. For example, a user who is 22 years old, female, has a mean glucose of 162 mg/dL, and experiences patterns of nighttime low glucose measurements, may have a high similarity score with other users in that age, gender, mean glucose measurement, and pattern experience.

Then, to determine application recommendations, the similarity score is combined with the prior application success of similar users. For instance, if users that are similar to a target user downloaded and used a particular application, and then saw their glycemia improve (e.g., as evidenced by reduced mean glycemia and reduced nighttime lows), then the recommendation system 412 can be configured to generate a high recommendation score for the particular application for the target user. Conversely, if other applications did not show such improvement, these applications would have lower recommendation scores for the target user. The application recommendations can be communicated to the computing device 108 for output.

Figure 11:
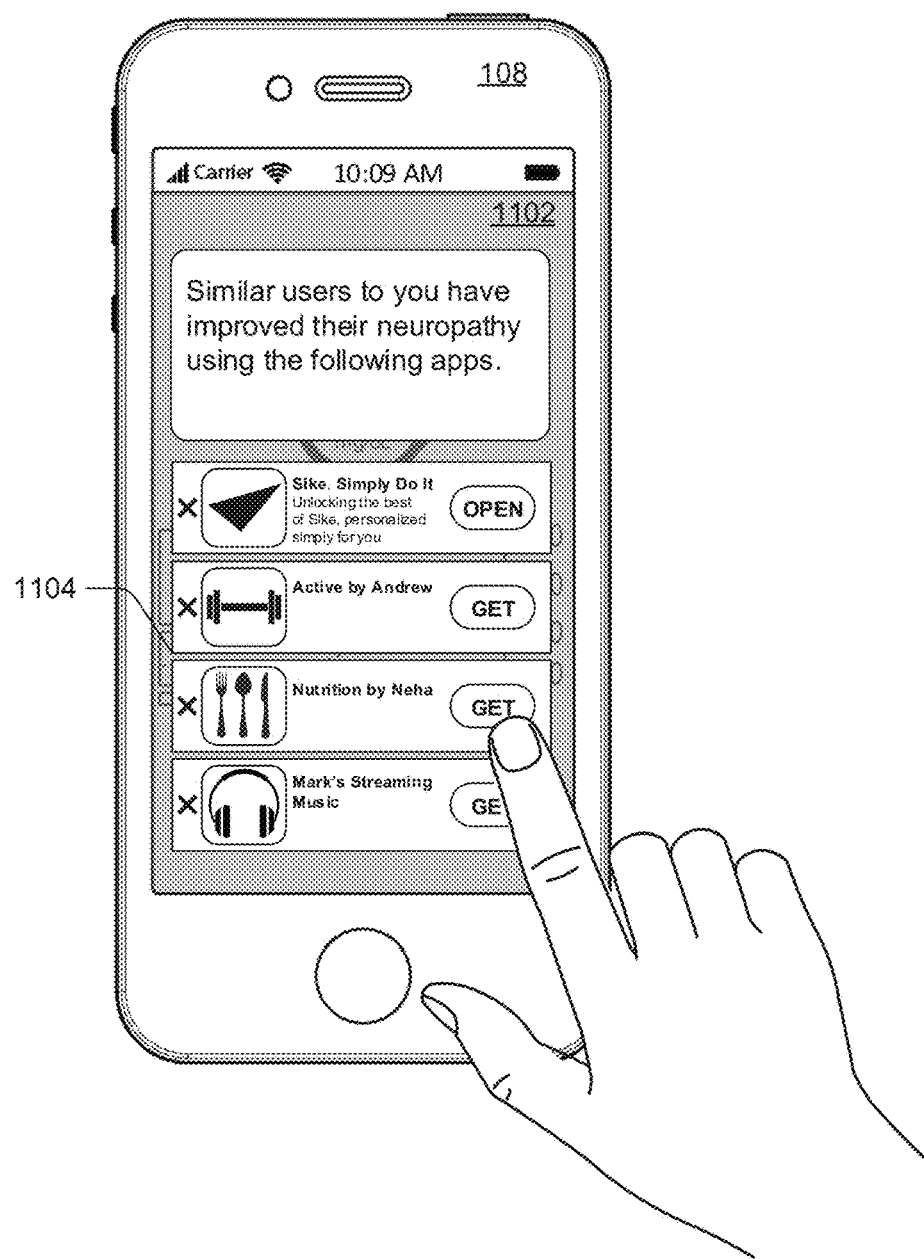
FIG. 11 depicts another example implementation of a user interface outputting a prediction and recommendation for supporting diabetes treatment decisions.

In the context of generating application recommendations, consider FIG. 11 which depicts an additional example 1100 of a user interface of the CGM platform displayed on a computing device coupled to a CGM system. The illustrated example 1100 includes a CGM user interface 1102 displayed by computing device 108. In this example, the CGM user interface 1102 is depicted as displaying recommended applications 1104. As discussed throughout, the recommended applications 1104 may be determined by the recommendation system 412 to improve a health condition of a target user based on the similarity of the user to other users in the user population 110 whose health condition improved based on usage of at least one of the recommended applications 1104. In this case, the recommended applications 1104 correspond to various third party applications. In FIG. 11, a user is depicted as selecting the application "Nutrition by Neha" in order to download this application to the user's smartphone.

Notably, the recommendation system 412 can further reinforce the application recommendations as the target user downloads and uses applications, thus reinforcing or negating prior recommendations and leading to improved follow-on recommendations in the future. For example, if the recommendation system 412 obtains glucose measurements 118 from the similar user indicating an improvement in the health condition of the similar user, then this feedback will positively reinforce the correlation between the improvement to the health condition of the subset of users and usage of the particular application. Conversely, if the glucose measurements 118 from the similar user indicates no improvement in the health condition (or a worsening of the health condition) of the similar user, then this feedback will negatively reinforce the correlation between the improvement to the health condition of the subset of users and usage of the particular application With regards to FIG. 11, for example, as the user begins interacting with the "Nutrition by Neha" application, application interaction data may be communicated to the CGM platform 112 via the CGM Platform API 310 and correlated with the user's glucose measurements 118 and additional data. In this way, the CGM platform 112 may continually update the models 404 used to recommend applications based on feedback received from application usage by the user population 110. In configurations where the machine learning model 408 is updated based on feedback, for instance, the model may be configured as a reinforcement learning model. The updated models 404 are then used to generate improved application recommendations.

Figure 12:
FIG. 12 depicts an example implementation of the user interface outputting information about a health trend.

Moreover, if the CGM platform 112 detects that usage of a particular application is improving the health condition of the user based on the updated glucose measurements 118, then the CGM platform 112 may communicate a notification of the improvement to the computing device 108 for output. In FIG. 12, for example, a notification 1202 is displayed by computing device 108 and indicates that usage of the "Nutrition by Neha" application has caused the user's neuropathy to improve. It is to be appreciated that this positive notification may incentivize the user to continue to use the application.

Validation Service

Figure 13:
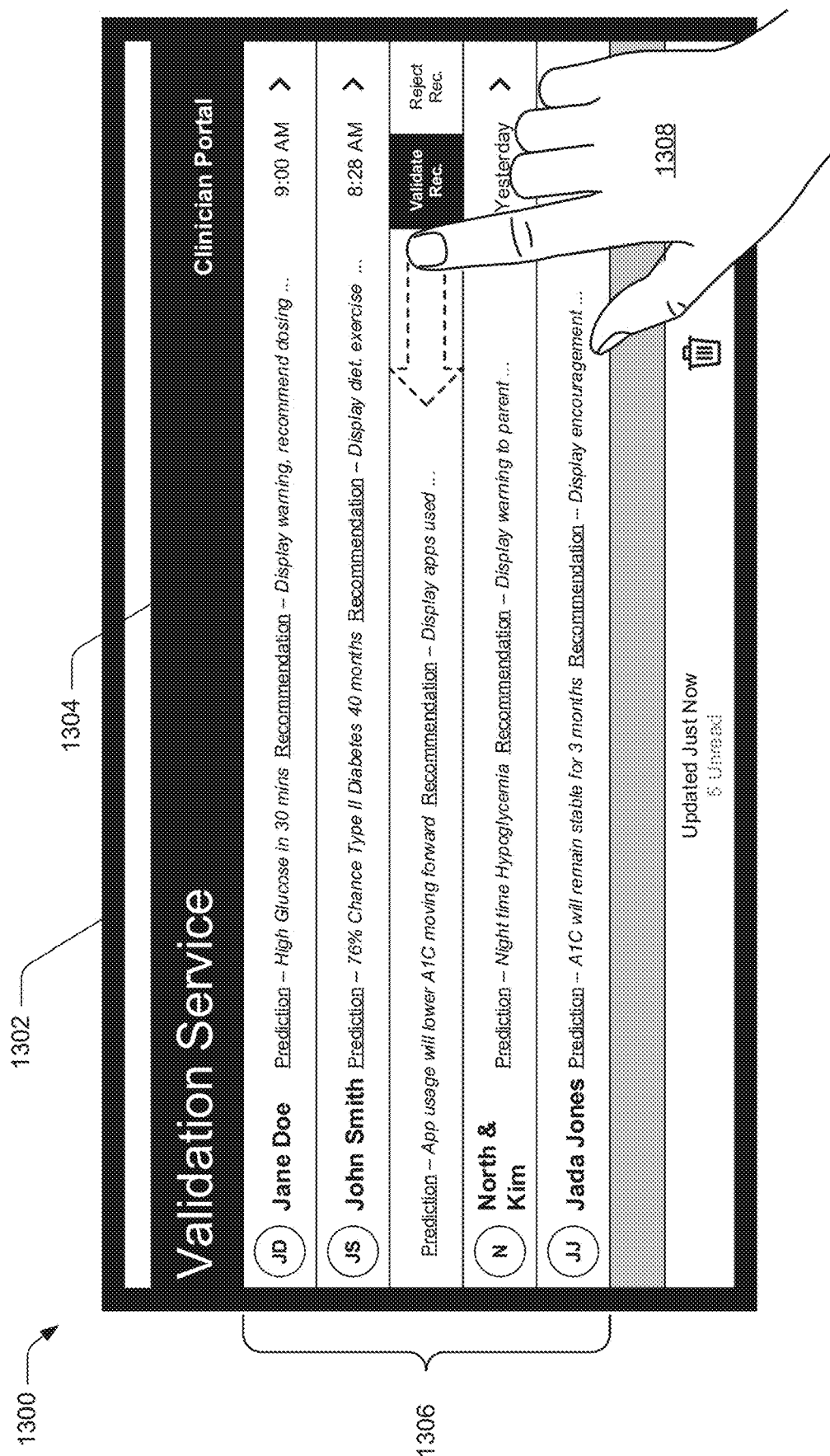
FIG. 13 depicts an example implementation of a user interface of a validation service with which an approved user can interact to validate recommendations generated by a CGM platform.

FIG. 13 depicts an example implementation 1300 of a user interface of a validation service with which an authorized user can interact to validate recommendations generated by a CGM platform.

In the illustrated example 1300, display device 1302 is depicted displaying a user interface 1304 of the validation service 502. Broadly speaking, interface elements of the user interface 1304 enable an authorized user to interact with those elements to validate or reject recommendations that are provided by the data analytics platform 126 and are intended for delivery to users, e.g., the person 102. Responsive to receiving input via a user interface element validating a recommendation (e.g., recommendation 322), the validation service 502 may route the recommendation to the computing device 108 of the respective user. As discussed above, the validation service 502 may also route the recommendation to the decision support platform 504. Responsive to receiving input via user interface element of the user interface 1304 rejecting a recommendation, the validation service 502 does not communicate the recommendation to the computing device 108. Instead, the validation service may communicate a notification to the data analytics platform 126 indicating that the recommendation is rejected. Additionally or alternately, an approved user of the validation service 502 may modify the recommendation and then send the modified recommendation to the computing device 108 of the user. As mentioned above, users that are authorized to validate recommendations provided by the data analytics platform 126 may include clinicians or other health care professionals, qualified to deliver health instruction to patients.

In the illustrated example 1300, the user interface 1304 displays stubs 1306 of recommendations provided to the validation service 502 by the data analytics platform 126. These stubs 1306 are configured as interactive elements with which a user can interact to review, validate, reject, and/or take some other course of action (e.g., modify) in relation to a respective recommendation. Although recommendation stubs are depicted in this example, other user interface elements may be used that enable authorized users to review, validate, reject, and/or take some other course of action (e.g., modify) in relation to a respective recommendation without departing from the spirit or scope of the described techniques.

In this example 1300, each of the stubs 1306 includes a user or patient name, an indication of the prediction 320 on which the respective recommendation 322 is based, and also an indication of the recommendation 322. User 1308 is depicted performing a gesture in relation to one of the stubs 1306—in this case a right-to-left swiping gesture—to expose further interface elements that are selectable to validate the respective recommendation 322 or reject it. It is to be appreciated that elements to validate or reject a respective recommendation may be exposed in other ways such as displayed as part of each of the stubs without requiring interaction such as the swiping gesture, displayed as part of a menu launched responsive to some interaction (e.g., right click with a mouse) on a stub, and so on. Although not illustrated, the stubs 1306 may also be selectable to expose a recommendation-specific user interface that outputs an entirety of the prediction and an entirety of the recommendation for review as well as a plurality of options for handling the recommendation—including the options to validate and reject the recommendation and other options.

Fault Detection and System Configuration Issues

Figure 14:
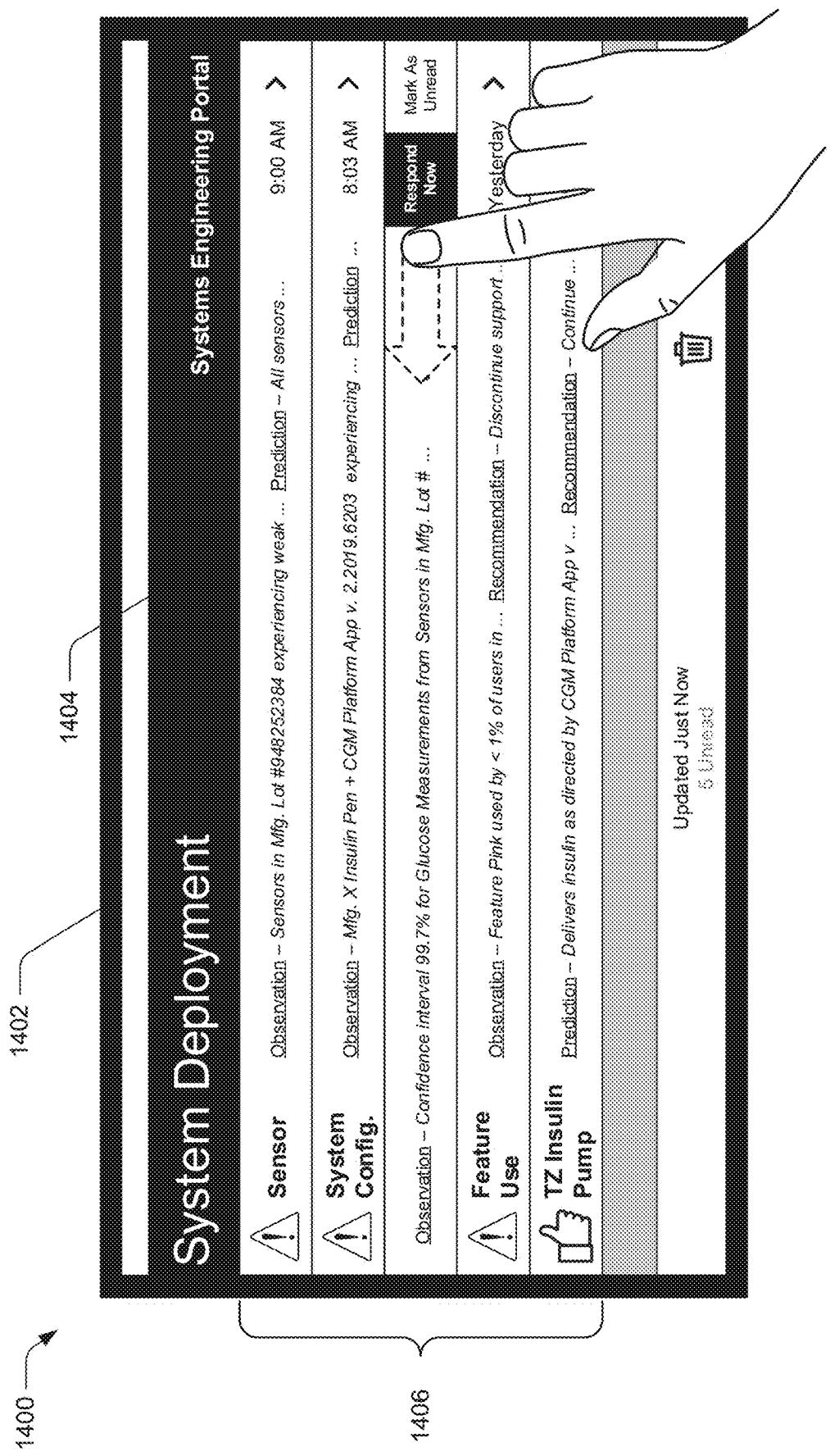
FIG. 14 depicts an example implementation of a user interface that outputs information about detected faults and system configuration issues in connection with use of the CGM platform.

FIG. 14 depicts an example implementation 1400 of a user interface that outputs information about detected faults and system configuration issues in connection with use of the CGM platform.

In the illustrated example, display device 1402 is depicted displaying a user interface 1404 of a fault detection and system configuration service. In one or more implementations, the fault detection and system configuration service may be included as part of or otherwise accessible to the CGM platform 112. It is also to be appreciated that portions of the user interface 1404 may be provided and displayed to other entities through respective portals, such as to manufacturers or service providers that provide devices or services, respectively, that can be used in connection with the CGM system 104. These devices may include one or more of the computing devices 108, the insulin delivery system 106, myriad physiological marker measuring devices, various components of the CGM system 104, and so forth.

The user interface 1404 displays stubs 1406 for a plurality of detected faults and system configuration issues. Although a variety of faults and issues are displayed in the user interface 1404, the faults and/or issues displayed to a given entity (e.g., a particular manufacturer or a regulatory body such as the U.S. Food and Drug Administration (FDA)) may be limited (e.g., to faults or issues involving the particular manufacturer's device or to information required by law to be exposed to the regulatory body). By way of contrast, users authenticating to the CGM platform 112 as employee or similar users (e.g., engineers, quality assurance, development partners, and so on) may have authorization to be shown all faults and/or issues related to the CGM platform 112.

In this example 1400, the stubs 1406 include stubs for events (e.g., faults) reported by one or more devices communicably coupled or otherwise related to the CGM platform 112, such as reported by the CGM system 104 about the sensor 202, the computing device 108, the insulin delivery system 106, third parties 306, just to name a few. The stubs 1406 also include stubs that relate to issues that arise in connection with particular system configurations which include the CGM system 104 but different combinations of other devices, such as configurations having a particular computing device 108 (e.g., particular manufacturer), a particular ensemble of computing devices 108 (e.g., a mobile phone corresponding to a first manufacturer and a smart watch corresponding to a second manufacturer), particular insulin delivery systems (e.g., insulin pen versus insulin pump and from different manufacturers), particular firmware and software versions, and so on.

The stubs 1406 also include stubs that convey one or more measures of confidence, e.g., confidence of data obtained by various components (e.g., a manufacturing lot of sensors 202), system configurations, in connection with users having various demographics, and so forth. In one or more implementations, the measures of confidence are confidence intervals. Additionally, the stubs 1406 include stubs indicating use of platform features (e.g., functionality and/or user interface elements of applications corresponding to the CGM platform 112). This information can be used by system developers to determine whether to continue developing and/or providing support in relation to the different features.

In relation to stubs that describe events reported by one or more devices, it is difficult if not impossible for developers corresponding to the CGM platform 112 to test, prior to deployment, all combinations of devices that may be used in connection with the CGM system 104 and applications of the CGM platform 112, e.g., mobile phone and smart watch applications. Instead, those developers may limit testing to combinations of devices most likely to be used (e.g., most popular mobile devices or insulin delivery systems 106) and/or the combinations recommended in content dispersed by the CGM platform 112, e.g., via publications, webpages, packaging, emails, advertising, and so forth. To this extent, developers may be aware of only a subset of issues with the tested combinations of devices, and have fixed them, but not issues with untested combinations.

By collecting and maintaining vast amounts of the glucose measurements 118, the CGM device data 214, and the supplemental data 304 in the storage device 120, the data analytics platform 126 can train and then leverage the models 404 to identify issues (e.g., faults) with the different combinations of devices used by the user population 110, such as issues observed with both tested and untested combinations during real world use. Indeed, the tested combinations of devices may not have been tested in the various ways in which they are actually used by the user population 110 in the real world. Accordingly, by using the models 404 to identify these issues, the data analytics platform 126 can notify developers of the issues, so that the developers can develop fixes for the issues and then deploy them, e.g., as firmware or software updates, as updates to the models 404, and so on.

Alternately or in addition, the data analytics platform 126 may use identification of these issues to adjust predictions and recommendations for the combinations experiencing the issues. By way of example, if a combination of devices used by a small subset of the user population (e.g., 1%) provides glucose measurements 118 to the CGM platform 112 that are consistently (and predictably) lower than glucose measurements 118 provided by other combinations, this information can be used to update real-time glucose measurements 118 presented to users via their computing devices 108.

This information can also be used by the models 404 to predict that a user having the combination of devices will experience the same issues as the subset of the population. Notably, this information can be used to ensure that valid (e.g., safe) recommendations are generated and provided to these users. The data analytics platform 126 may use the capability to identify issues, such as faults, with different combinations of devices in a variety of ways without departing from the spirit or scope of the described techniques.

In relation to stubs that describe use of platform features, this information may be used to determine whether to continue developing and/or providing support in relation to the different features, as noted above. In one or more implementations, the data analytics platform 126 can analyze the data maintained in the storage device 120 to determine a cost to a company corresponding to the CGM platform 112 of supporting various features of the CGM platform 112, such as various functionality provided by its CGM system 104 and applications. As part of this, the data analytics platform 126 is configured to measure a variation, co-variation, and statistical dependence between each functionality deployed by the CGM platform 112, such as variation, co-variation, and statistical dependence between functionality of the CGM system 104 to measure the person 102's temperature, functionality of the CGM platform 112's mobile phone application to identify likely occurrence of hypoglycemia during the night, functionality of the CGM platform 112's smart watch application to use tactile feedback (e.g., vibrations) in connection with outputting notifications, and so on.

In one or more implementations, the data analytics platform 126 determines the variation and co-variation by generating a matrix with dimensions that correspond to a predetermined number of users sampled from the user population 110 (e.g., 50,000 users) and to a number of features (e.g., functionalities) deployed by the CGM platform 112—or the number of features under consideration for potentially discontinuing development or support. In the following discussion, the predetermined number of users is represented by the term m and the number of features is represented by the term n. To this end, the data analytics platform 126 constructs an m×n matrix, where each cell of the matrix indicates whether a sampled user uses the corresponding feature. The data analytics platform 126 may determine that a user uses a feature in a variety of ways, and use may be defined differently for different features. For example, the data analytics platform 126 may determine that a user has used a feature if the data from the storage device 120 indicates that the user has ever used the feature, has spent more than a threshold amount of time using the feature or with the feature being active, has used the feature more than a threshold number of times, has allowed the feature to be active (e.g., allows notifications), and so on.

Using the m×n matrix, the data analytics platform 126 computes a variation score of a given feature i as a function of a number of users a that "use" the given feature i from the number of sampled users m. In one example, the data analytics platform 126 computes the variation according to the following:

$$\varphi(i) = \log\frac{a}{m}$$

Here, the term φ(i) represents the variation score. The data analytics platform 126 is also configured to compute a co-variation score of the given feature i and another feature j as a function of the number of users a that use the given feature i and as a function of a second number of users b that use the other given feature j from the number of sampled users m. The data analytics platform 126 also computes the co-variation as a function of a third number of users c that use the given feature i and the other feature j, concurrently. In one example, the data analytics platform 126 computes the co-variation score according to the following:

$$\varphi(i, j) = \log\frac{c}{m} - \varphi(i) - \varphi(j)$$

Here, the term φ(i,j) represents the co-variation score and the term φ(j) represents the variation score of the other given feature j.

The data analytics platform 126 measures the statistical independence between the different features by constructing a contingency table for each pair of the features, such that each feature is paired with m−1 features and contingency tables are generated for every pair. The data analytics platform 126 performs a known independence test on each table. In one or more implementations, the known independence test comprises a Chi-Square Test for Independence, the output of which is a P-value, e.g., the probability of observing a sample statistic as extreme as a test statistic. The data analytics platform 126 then compares the output of the known independence test (e.g., the P-value) for each table to a significance level threshold. If the output satisfies the significance level threshold, then the data analytics platform identifies the pair of features as dependent features.

The data analytics platform 126 then determines the cost of the given feature i as a function of the given feature's variation φ(i) plus the pairwise scores φ(i,j) for other features that are statistically dependent with the given feature i. The data analytics platform 126 may then present these scores to authorized users (e.g., engineers, marketing persons, and so on) corresponding to the CGM platform 112, such as by display via the user interface 1404 or some other interface. It is to be appreciated that a cost of the CGM platform 112's features may also be determined in other ways.

Engagement State Transition Prediction

Figure 15:
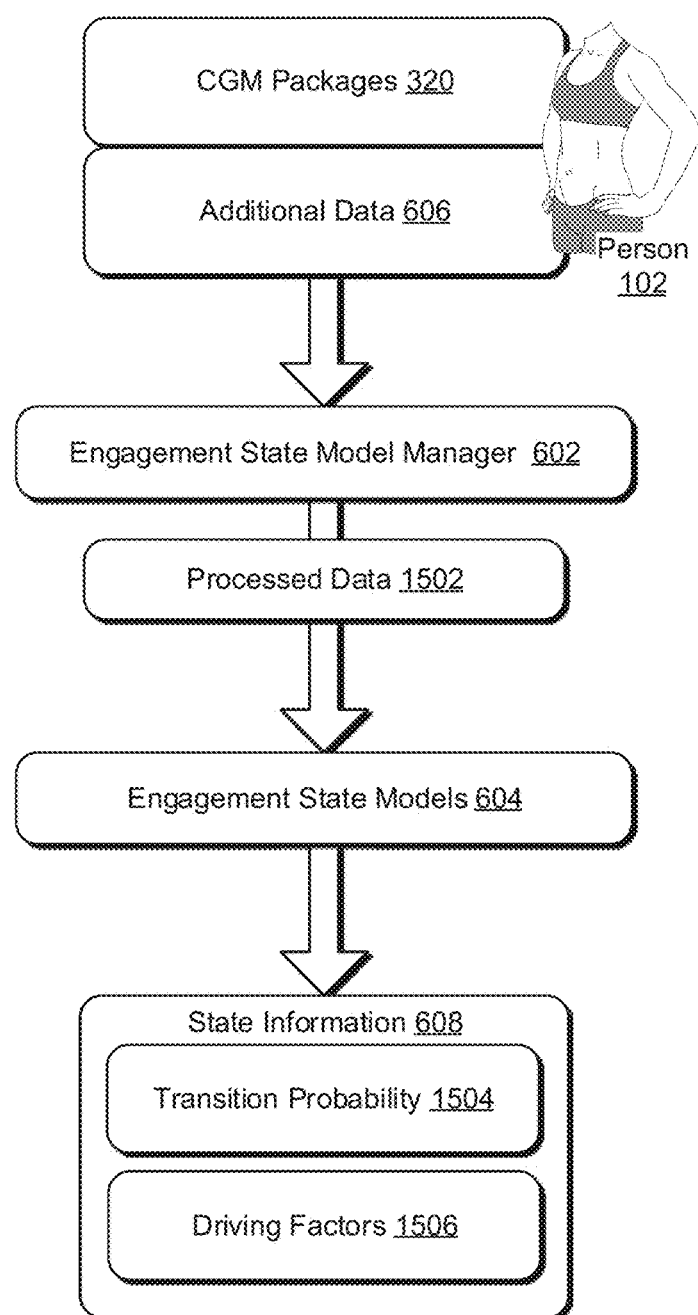
FIG. 15 depicts an example implementation of the multi-step engagement system generating state information including a probability of transitioning from a current state to a new state and predicted driving factors of the transition.

FIG. 15 depicts an example implementation 1500 of the multi-step engagement system generating state information including a probability of transitioning from a current state to a new state and predicted driving factors of the transition.

In the illustrated example 1500, the engagement state model manager 602 is depicted obtaining the CGM packages 302 and the additional data 606 of the person 102. Generally speaking, this data is processed using the engagement state model manager 602 and the engagement state models 604 to generate the state information 608. This example includes processed data 1502, which the engagement state model manager 602 generates based on the CGM packages 302 and the additional data 606 of the person 102 and provides as input to the engagement state models 604.

By way of example, the engagement state model manager 602 may generate the processed data 1502 as a feature vector which has features determined pertinent to identifying a state of engagement with the CGM system 104 and based on which the model is generated. When configured as a feature vector, the processed data 1502 has values for the features that are derived from the CGM packages 302 and the additional data 606 of the person 102. In an scenario where the engagement state models 604 predict a probability of the person 102 to discontinue use of the CGM system 104— such that the transition probability 1504 is a probability that the person 102 will transition to a discontinued use stage— the processed data 1502 may have features describing a CGM data history of the person, where the CGM data history is derived from the glucose measurements 118 of the CGM packages 302, data indicative of receipt of those packages by the CGM platform 112, and purchase history in relation to the CGM system 104 or portions thereof as well as purchase history of services provided by the CGM platform 112. In this scenario, the processed data 1502 may also have features describing a complaint history of the person 102, census data features, payment information features, and so on.

In this example 1500, the engagement state models 604 are configured to receive the processed data 1502 as input. In operation, a given engagement state model 604 is configured to generate state information 608 for processed data 1502 configured in a particular format, e.g., having a particular number of features with values in an expected format. Based on the processed data 1502 and the underlying model learned through a machine learning approach as discussed above (e.g., supervised learning, unsupervised learning, reinforcement learning), the engagement state models 604 output the state information 608. Here, the engagement state models 604 generate the transition probability 1504 and the driving factors 1506. The transition probability 1504 may represent a probability of the person 102 to transition from a current state to a new state, e.g., the discontinued use state. In one or more implementations, the state information 608 may include transition probabilities for each of a plurality of possible states. The driving factors 1506 may indicate which factors likely drive a transition from the current state to the new state. In the implementation where the transition probability 1504 corresponds to a probability the person 102 will transition to a discontinued use stage, the driving factors 1506 indicate the factors that are likely driving the person to transition to the discontinued use stage. In one or more implementations, the engagement state models 604 may compute probabilities of each factor (e.g., feature) represented in the processed data to cause transition to the next state and designate the features as driving or not based on those probabilities, e.g., the top-k features or having probabilities above some threshold.

In the continuing example where the transition probability 1504 represents a probability of the person 102 to transition to a discontinued use stage and the driving factors 1506 indicate the aspects described by the processed data 1502 that are causing the transition, the state information 608 may be communicated to an intervention platform 802. The intervention platform 802 may deploy different strategies to intervene (or not) based on the transition probability 1504 and the driving factors 1506.

Diabetes Search Queries

Figure 16:
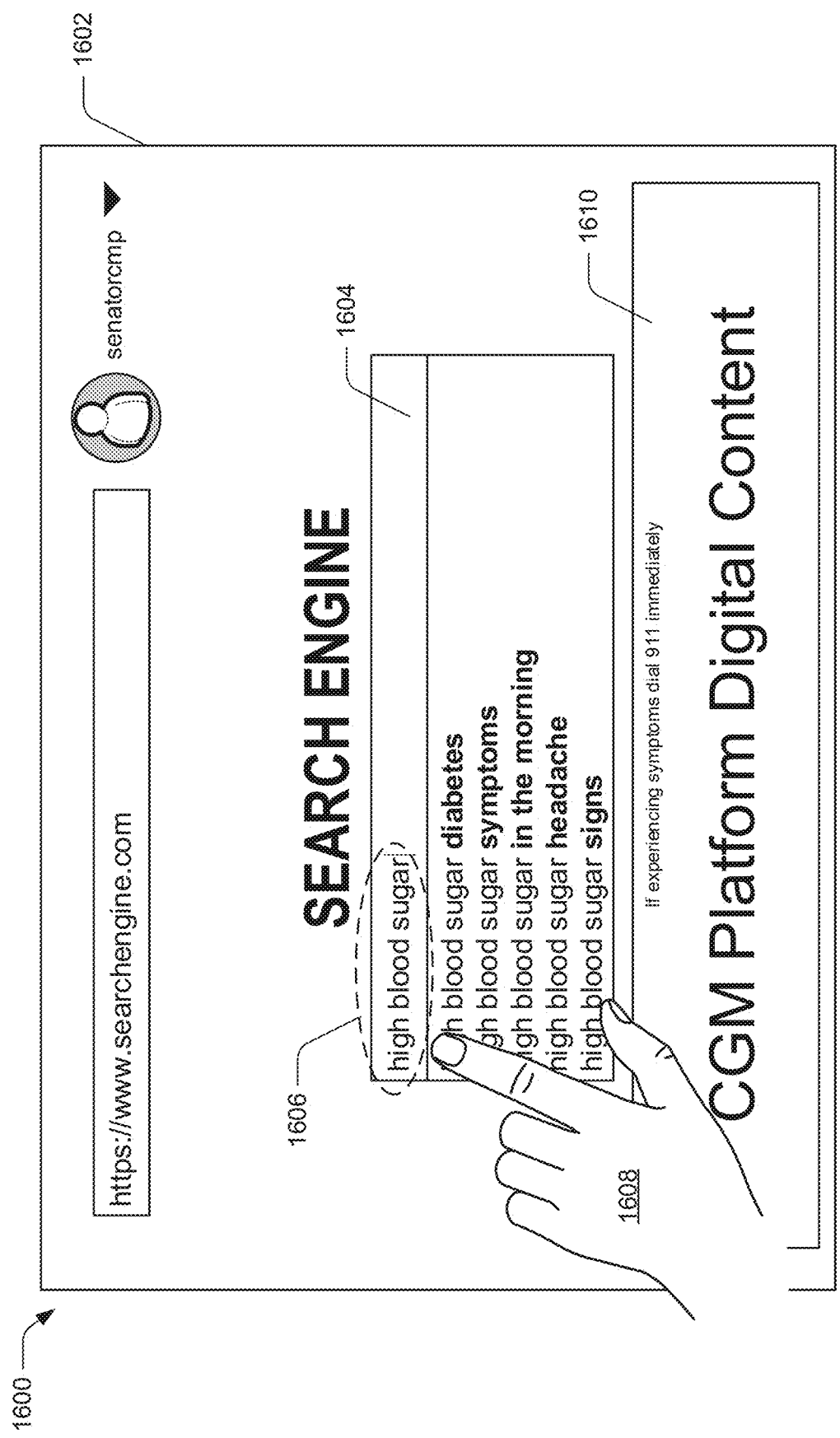
FIG. 16 depicts an example implementation of a user interface that receives search queries related to diabetes.

FIG. 16 depicts an example implementation 1600 of a user interface that receives search queries related to diabetes.

The illustrated example 1600 includes a user interface 1602. The user interface 1602 includes search query input element 1604 which enable a user to input a search query. It is to be appreciated that although the search query input element 1604 is illustrated as a text entry field, a search query may be received in a variety of ways without departing from the spirit or scope of the described techniques, such by receiving a voice command via a voice assistant device.

In the illustrated example 1600, a search query 1606 for "high blood sugar" is received based on input from a user 1608. In accordance with the described techniques, this particular search query 1606 may be referred to as a health-related, or more specifically, a diabetes-related search query. Other examples of diabetes-related search queries may include "urination," "headaches," "veins," and "diabetes," to name just a few. Indeed, health- and diabetes-related search queries may include a variety of terms and combinations of those terms, including terms related to nutrition and exercise. In any case, receipt of such search queries may be captured by tracking a user's online activity, and data may be generated describing the receipt of these search queries. This search-query data may be one source of the additional data 606. Accordingly, the engagement state models 604 may be generated, in part, using search-query data in one or more implementations, e.g., to learn an underlying model for stages of engagement with the CGM system 104. In this particular example, searching for health- and diabetes-related information may correspond to an inquiry or selection stage of engagement in relation to the CGM system 104, such that the engagement state models 604 predict that a user submitting such search queries corresponds to at least one of those stages.

Practically, however, a user submitting such search queries may be experiencing dangerous health conditions and/or likely to experience dangerous health conditions in the near future due to diabetes. To this end, providing this user with support based on the user's predicted state so that the user can monitor glucose may be paramount to preventing or mitigating dangerous health conditions. The described systems may thus use the search queries to educate the user about glucose monitoring. The described systems may also use the search queries to cause the user to obtain diagnostic solutions or a CGM system 104 and utilize the CGM platform 112 sooner than the user otherwise would have received such support with conventional approaches. By leveraging search query information, rather than waiting for the user to schedule an appointment with a medical provider, for instance, the CGM platform 112 can sooner provide information in the form of delivered digital content to the user or otherwise initiate communication with the user about health conditions, diagnostic solutions, and potential treatment options, if necessary.

The illustrated example 1600 includes digital content component 1610. The digital content component 1610 represents just one manner in which the CGM platform 112 can communicate with the user 1608 based on receiving health- and diabetes-related search queries. In particular, the digital content component 1610 is depicted being displayed via the user interface 1602, where the display may be responsive to receiving the search query 1606. The digital content component 1610 may correspond to a digital advertisement displayed via the user interface 1602, a search result displayed via the user interface 1602, a pop-up or toast notification displayed via the user interface 1602, and so on. Certainly, the digital content component 1610 may be configured in a variety of ways without departing from the spirit or scope of the techniques, such as audible information output via a voice assistant device, mobile notifications (e.g., via a mobile phone or smart watch), information presented via one or more social networks, an SMS message, and so forth. Alternately or additionally, the CGM platform 112 may initiate other types of communication with the user based on the health- and diabetes-related search queries, such as by sending mail to the user, calling the user, and so forth. Other types of communication may include communicating with a caregiver of the user (e.g., parent or guardian), or a medical professional associated with the user, to name just a few.

The digital content component 1610 may provide support so that the user can monitor glucose and prevent or mitigate dangerous health conditions, such as by providing further information about health conditions that arise due to diabetes, how to contact medical providers, how to contact customer support representatives of the CGM platform 112, information about the ease of using the CGM system 104, information about the CGM system 104, information about other persons with diabetes and their lives, and so forth. Indeed, the digital content component 1610 may include a variety of information without departing from the spirit or scope of the described techniques. It is further to be appreciated that these techniques may also be deployed to communicate with potential "commercial" users of the CGM system 104 and the CGM platform 112, such as when users enter search queries like "tracking blood sugar," "how does blood sugar affect performance," "blood glucose athletic performance," "blood glucose and mental performance," and so forth. Such users may also be determined, using the engagement state models 604, to be in a state that captures their stage as being in an inquiry stage or selection stage, but with a "commercial" user role rather than a "patient" role.

Intervention Strategy Implementations

As discussed above, the CGM packages 302 and the additional data 606 of the user population 110 are used by the engagement state model manager 602 to generate the engagement state models 604, which, based on the particular machine learning techniques used to generate these models, segments the data of the user population 110 into various states (or segments), e.g., clusters of data exhibiting similar patterns. As also noted above, the different states may capture roles of users of the user population 110 in relation to the CGM system 104 as well as stages along a journey of engagement with the CGM system 104. Accordingly, the engagement state models 604 may model states corresponding to patients prescribed and using the CGM system 104 (e.g., a first role) and states corresponding to non-prescribed, commercial users of the CGM system 104 (e.g., a second role), among various other roles. Notably, a patient prescribed and using the CGM system 104 and that also uses a first application of the CGM platform 112 may correspond to a different state modeled by the engagement state models 604 than a patient prescribed and using the CGM system 104, but that is not using the first application.

Regardless, these states, and specifically the roles corresponding to the states may affect an intervention strategy deployed, if any. Moreover, various patterns in the data considered may indicate different states and state transitions for the different roles. Consider an example in which a first user is a patient that is prescribed and uses the CGM system 104 (e.g., in connection with treatment for diabetes) and in which a second user is a commercial user of the CGM system 104 (e.g., in an attempt to optimize athletic performance).

Consider also in this example that the CGM packages 302 of the first user (the patient) include glucose measurements 118 that vary wildly (outside of a desired range) while the CGM packages 302 of the second user (the commercial user) include glucose measurements 118 that vary little (and are consistently within the desired range). In both cases, the engagement state models 604 may identify that the users are likely to transition to a discontinued use state, as indicated by the state information 608 specifically the transition probability 1504 output by the engagement state models 604. In reality, this may be due to the first user's treatment plan being ineffective, or not followed, to "level-out" his or her glucose levels causing the user to be frustrated with the CGM system 104. In contrast, the second user may, through use of the CGM system 104 over a period of time, have identified behaviors that cause his or her glucose level to spike and eliminated those behaviors from his or her life, e.g., eating certain foods, failing to exercise, and so forth.

In any case, the strategies to prevent the first and second users from discontinuing use of the CGM system 104 (transitioning to a discontinued use state) may be drastically different. As noted above, these strategies may be generated based on the driving factors 1506 that are likely to cause the users to transition to a different state. Indeed, the driving factors for the first and second users may be drastically different—the first user's driving factors 1506 may include inconsistent glucose measurements 118, high stress levels, and inconsistent nutrition (although unbeknownst to the first user), for example, while the second user's driving factors 1506 may include consistent glucose measurements 118, elimination of foods that formerly caused spikes in the glucose measurements 118, and use of a smart watch to monitor stress. Regardless of the actual driving factors 1506, they may be utilized to generate or otherwise develop an intervention strategy.

By way of example, the intervention platform 802 may obtain the state information 608 for the first and second users, indicating their transition probabilities 1504 of transitioning from a current state to a new state of discontinuing use of the CGM system 104 as well as indicating their driving factors 1506 likely to drive the transition. Given this information, the intervention platform 802 customizes the intervention strategy for the different users. This may also be carried out using an engagement state model 604 or other logic, which has been learned from data describing historical intervention strategies (both that have worked and that have not worked with particular users).

In relation to the first user, the intervention platform 802 may deliver information about success stories with the CGM system, notify a coach to contact the first user, provide information about consistent nutrition, and/or communicate in other ways, based on interventions that have worked previously for users having a same or similar state (and driving factors) as the first user. In relation to the second user, though, the intervention platform 802 may deliver information about other products or services of the CGM platform 112 for purchase (e.g., to further optimize athletic performance), deliver information about behaviors that users who discontinue use of the CGM system 104 fail to consider without the constant surveillance of the system, deliver information about further optimizations that can be made while using the CGM system 104, and/or communicate in other ways, based on interventions that have worked previously for users having a same or similar state (and driving factors) as the second user. Indeed, intervention strategies may be customized in a variety of ways depending on the state information 608 generated for a user and based on strategies that have worked previously for similar users, e.g., as indicated by a machine learning model or other logic.

Example Procedures

This section describes example procedures for recommendations based on continuous glucose monitoring (CGM). Aspects of the procedures may be implemented in hardware, firmware, or software, or a combination thereof. The procedures are shown as a set of blocks that specify operations performed by one or more devices and are not necessarily limited to the orders shown for performing the operations by the respective blocks. In at least some implementations the procedures are performed by a data analytics platform, such as data analytics platform 126 of CGM platform 112 that makes use of a prediction system 316 and a recommendation system 412.

Figure 17:
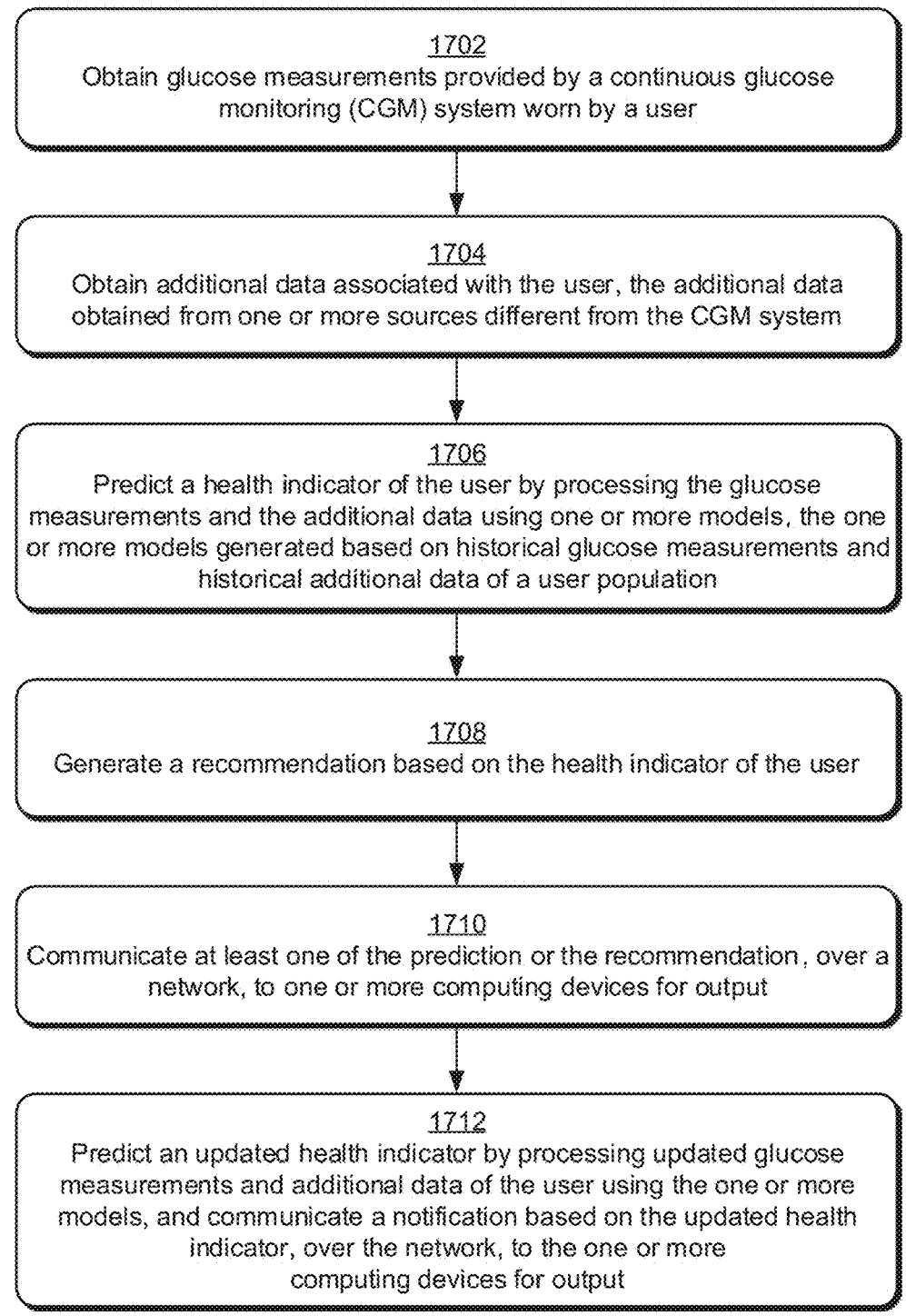
FIG. 17 depicts a procedure in an example implementation in which a prediction and a recommendation are generated based on both glucose measurements and additional data of a user.

FIG. 17 depicts an example procedure 1700 in which a prediction and a recommendation are generated based on both glucose measurements and additional data of a user.

Glucose measurements provided by a CGM system worn by a user are obtained (block 1702). By way of example, the CGM platform 112 obtains glucose measurements 118 detected by the CGM system 104 worn by person 102. As discussed throughout, the CGM system 104 is configured to monitor glucose of the person 102 continuously. For instance, the CGM system 104 may be configured with sensor 202 that is inserted subcutaneously into skin 206 of the person 102, and continuously measures analytes indicative of the person 102's glucose for generating glucose measurements. In one or more implementations, the CGM platform 112 obtains the glucose measurements 118 from a computing device 108 that is communicatively coupled to the CGM system 104, such as a mobile phone or wearable device of the user.

Additional data associated with the user is obtained (block 1704). By way of example, the CGM platform 112 obtains additional data 410 from various devices, sensors, applications, or services. Thus, in accordance with the principles discussed herein, the additional data may be obtained from one or more "sources" that are different from the CGM system 104 from which the glucose measurements 118 are provided. The additional data 410 may include least one or more portions of the CGM device data 214 additional to the glucose measurements 118, the supplemental data 304, the third party data 314, data from the IoT 114, and so forth.

A health indicator of the user is predicted by processing the glucose measurements and the additional data using one or more models (block 1706). In accordance with the principles discussed herein, the one or more models are generated based on historical glucose measurements and historical additional data of a user population. By way of example, the prediction system 316 of the data analytics platform 126 generates a prediction 320 that includes a health indicator by processing the glucose measurements 118 and additional data 410 of the person 102 using one or more models 404. The one or more models 404 are generated based on the glucose measurements 118 and the additional data 410 of the user population 110. The one or more models 404 may include, by way of example and not limitation, a statistical model 406 and/or an additional machine learning model 408.

A recommendation is generated based on the health indicator of the user (block 1708). By way of example, regardless of whether the statistical model 406, the machine learning model 408, or some combination of statistical and/or machine learning models is used to generate the prediction 320, the prediction 320 is obtained by the recommendation system 412 of the data analytics platform 126. The recommendation system 412 is configured to generate the recommendation 322 based on the prediction 320. In some cases, the health indicator corresponds to a predicted negative health condition, such as a prediction that the user will develop Type II diabetes in the next 40 months. In this scenario, the recommendation system 412 can generate the recommendation 322 based on logic that associates the predicted negative health condition with one or more actions or behaviors that mitigate the predicted negative health condition. As such, the recommendation 322 may include the one or more actions or behaviors intended to mitigate the predicted negative health condition.

At least one of the prediction or the recommendation is communicated, over a network, to one or more computing devices for output (block 1710). By way of example, the data analytics platform 126 communicates the prediction 320 and/or the recommendation 322 to the computing device 108 for output. The computing device 108 can then display the prediction 320 and/or the recommendation 322 in a CGM interface. As shown in FIG. 9, for example, CGM user interface 902 displays a prediction 904 along with a recommendation 906. In this example, the prediction 904 indicates that the user has a 76% chance of developing Type II diabetes in 40 months. The recommendation 906 includes one or more actions or behaviors that the user can take to improve the user's predicted negative health condition. In FIG. 9, for example, the recommendation 906 includes a recommendation for a customized eating plan, a recommendation for a customized exercise plan, and a recommendation to get a coach that can help the user stay on track with the recommended nutrition and exercise plan.

In one or more implementations, the prediction or the recommendation can be communicated to a validation service 502 and/or a decision support platform 504 prior to, or instead of, being communicated to the computing device 108 of the user. In this way, the validation service 502 and the decision support platform 504 may act as intermediaries between the data analytics platform 126 and the computing device 108. In the scenario in which the prediction or recommendation is communicated to the validation service 502, the validation service 502 can validate the recommendation 322. This means determining whether the recommendation 322 is valid (e.g., safe) and can be further communicated to the decision support platform 504 and/or directly to the computing device 108. The validation service 502 may expose the recommendation 322 to a user that has been authorized by the validation service 502, such as a clinician, to validate recommendations.

Responsive to a recommendation being validated (e.g., by a clinician or logic of the validation service 502), the recommendation may be further routed to the decision support platform 504 or directly to the computing device 108. When a recommendation is not validated (i.e., it is rejected), the recommendation may not be further routed to the decision support platform 504 or directly to the computing device 108. Instead, the validation service 502 may modify the recommendation (e.g., according to clinician input) and/or provide a notification back to the data analytics platform 126 that the recommendation is rejected. In this scenario, the data analytics platform 126 may be able to add an indication of rejection as input to the prediction system and initiate generation of a different prediction 320 and/or recommendation 322. Indeed, the models 404 may be updated based on validations and rejections received from the validation service 502. In scenarios where the validation service 502 validates the recommendation 322 and consequently allows the recommendation 322 to be forwarded directly to the computing device 108, the computing device 108 may output the recommendation 322, such as via display, via speakers, via tactile feedback, and so on, as described above and below.

As mentioned above, the recommendation 322 may also be communicated to the decision support platform 504 by the validation service 502 or alternately may be communicated to the decision support platform 504 directly from the data analytics platform 126, bypassing the validation service. Based on the recommendation 322, as well as based on other information accessible about the corresponding user, the customer service specialist may determine how to support the user. By way of example, the customer service specialist may determine to call the user to provide voice support during a phone call.

An updated health indicator is predicted by processing updated glucose measurements and additional data of the user using the one or more models, and a notification based on the updated health indicator is communicated, over the network, to the one or more computing devices for output (block 1712). By way of example, the data analytics platform 126 continuously gathers the glucose measurements 118 and additional data 410 for the user. As such, the prediction system 316 can predict an updated health indicator by processing the updated glucose measurements and additional data using the one or more models 404. As shown in FIG. 10, for example, based on the continuous analysis of the user's updated glucose measurements 118 from the CGM system 104 and the additional data 410 indicating the user is making better food choices (as indicated by the user's nutrition log) and exercising more frequently (as indicated by the steps data and exercise log), the prediction system 316 generates an updated prediction, which is communicated to the computing device 108 for display as notification 1002.

Figure 18:
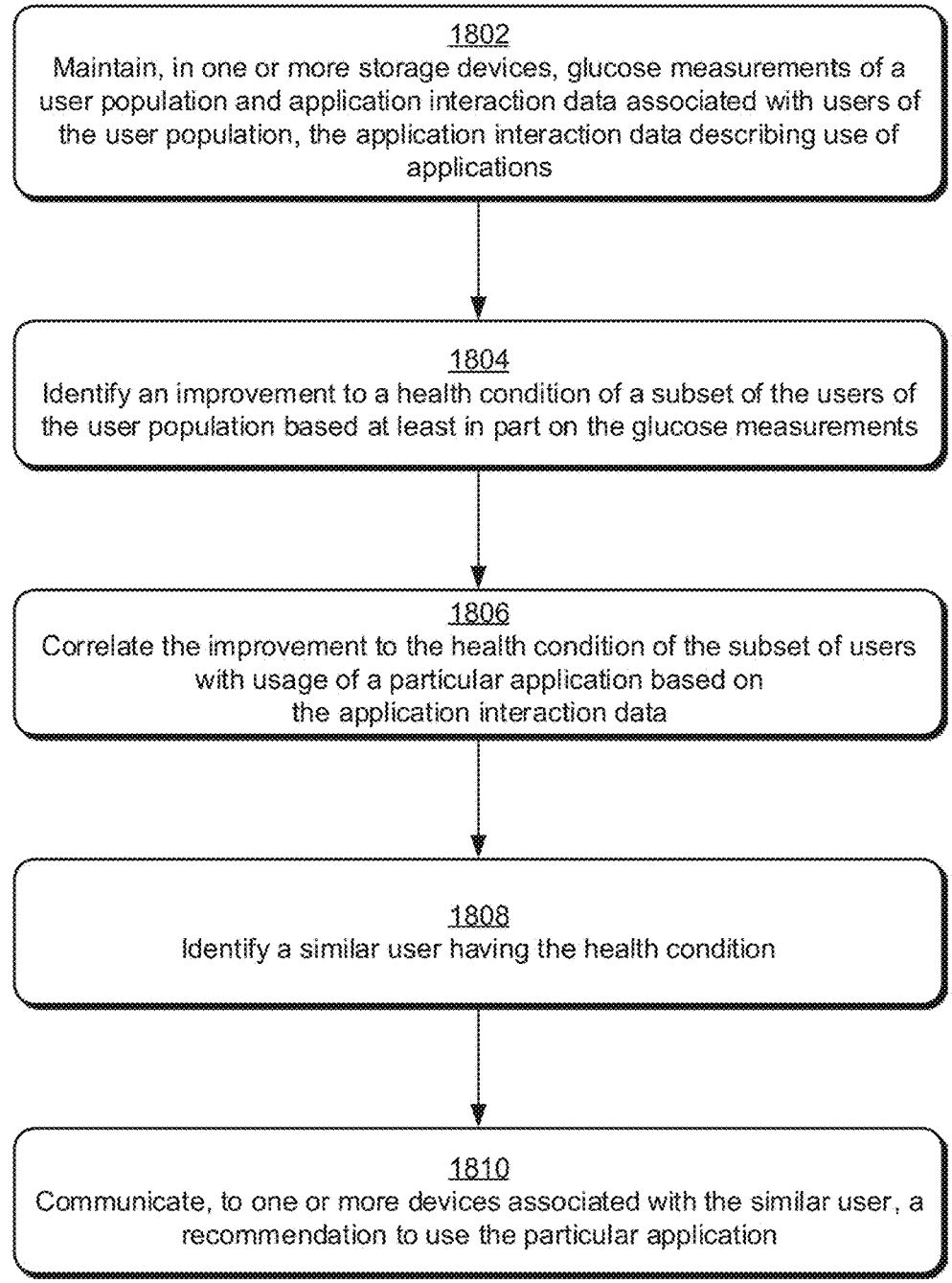
FIG. 18 depicts a procedure in an example implementation in which a recommendation to use a particular application is communicated to one or more devices of a similar user.

FIG. 18 depicts an example procedure 1800 in which a recommendation to use a particular application is communicated to one or more devices of a similar user.

Glucose measurements of a user population and application interaction data associated with users of a user population are maintained in one or more storage devices (block 1802). In accordance with the principles discussed herein, the application interaction data describes usage of applications (e.g., usage of "apps" by various users of the user population). By way of example, the CGM platform 112 obtains glucose measurements 118 detected by the CGM system 104 worn by person 102 and maintains the glucose measurements 118 in storage device 120. Additionally, the CGM platform obtains application interaction data from various applications, such as applications provided by third parties 306.

An improvement to a health condition of a subset of the users of the user population is identified based at least in part on the glucose measurements (block 1804), and the improvement to the health condition of the subset of users is correlated with usage of a particular application based on the application interaction data (block 1806). By way of example, the CGM platform 112 can aggregate the application interaction data, along with the glucose measurements 118 and additional data in order to determine whether a user's interaction with a particular application or service correlates to improvement of the user's health. For example, based on the glucose measurements 118, the CGM platform 112 can objectively determine an improvement in a health condition of a user. The CGM platform 112 can then correlate the improvement or decline in the user's health with usage of a particular application based on the application interaction data. For example, if the CGM platform detects an improvement with the user's health that coincides with heavy usage of a particular application, then the CGM platform may determine that the particular application is correlated with the improvement.

A similar user having the health condition is identified (block 1808), and a recommendation to use the particular application is communicated to one or more devices associated with the similar user (block 1810). By way of example, the recommendation system 412 can identify a similar user having the health condition, and generate a recommendation to the similar user to utilize the particular application that helped to improve the health condition of the subset of similar users. To do so, the recommendation system 412 can predict a probability of a similar improvement in a health condition through usage of a particular application by other users in the user population and recommend applications with a high probability of improving health to other similar users.

The application recommendations can be communicated to computing device 108 for output. By way of example, as shown in FIG. 11, the CGM user interface 1102 is depicted as displaying recommended applications 1104. In this case, the recommended applications 1104 correspond to various third party applications. In FIG. 11, a user is depicted as selecting the application "Nutrition by Neha" in order to download this application to the user's mobile phone.

Figure 19:
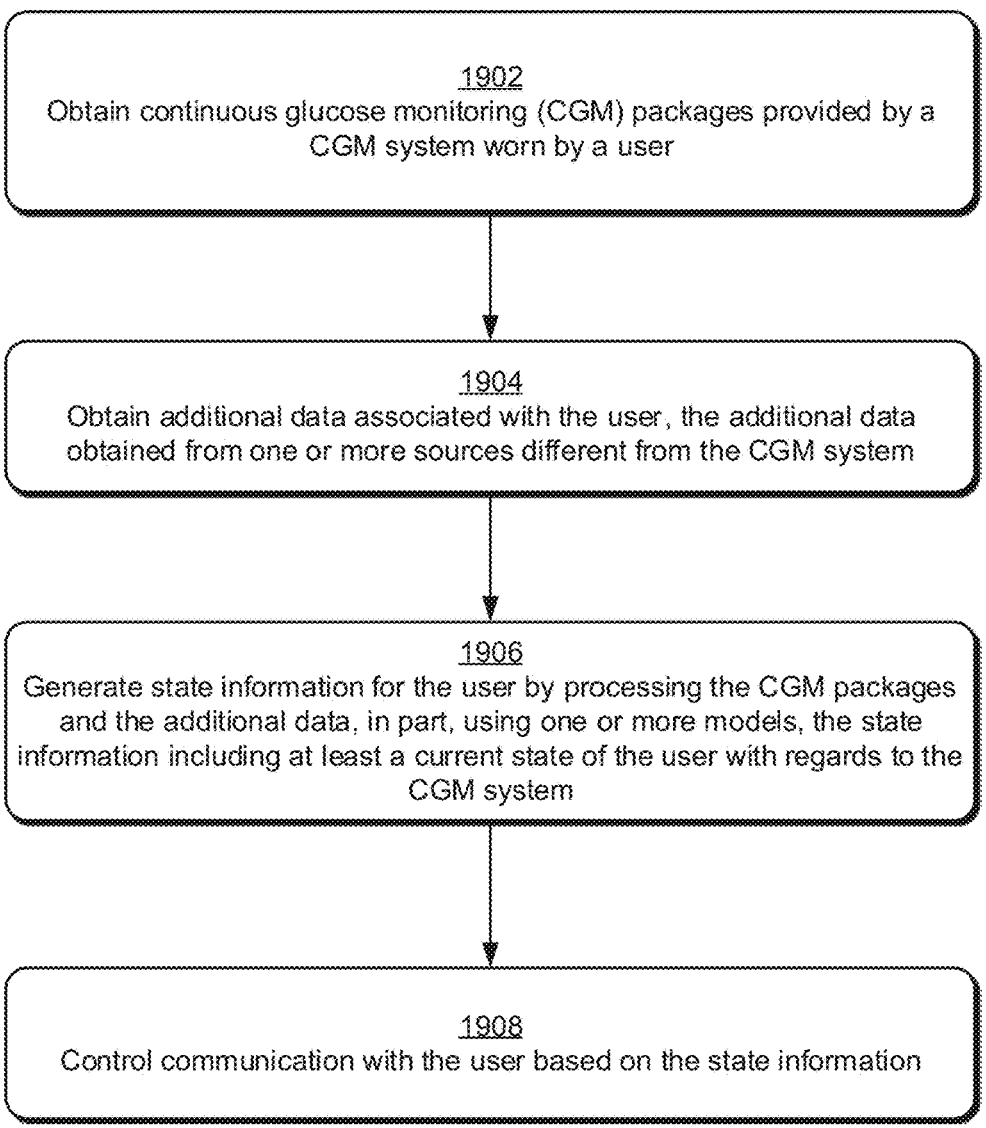
FIG. 19 depicts a procedure in an example implementation in which state information is generated to control communication with a user.

FIG. 19 depicts an example procedure 1900 in which state information is generated to control communication with a user.

CGM packages provided by a CGM system worn by a user are obtained (block 1902). By way of example, the multi-state engagement system 318 obtains CGM packages 302 provided by CGM system 104 worn by person 102. The CGM package data may include one or more of glucose measurements, characteristics of the measurements, or characteristics of receipt by a CGM platform of the CGM package data.

Additional data associated with the user is obtained (block 1904). In accordance with the principles discussed herein, the additional data may be obtained from one or more sources different from the CGM system. By way of example, the multi-state engagement system 318 obtains additional data 606 of the user population 110. This additional data 606 may include, by way of example and not limitation, purchase history data (e.g., describing purchases of the CGM systems 104, portions thereof (e.g., disposable sensor application assemblies), and/or services provided by the CGM platform 112), complaint data, customer service data (e.g., describing user interactions with customer service representatives such as whether a user responds to an attempt by a customer service representative to contact the user), physiological data, socioeconomic data, attitudinal data, behavioral data, purchase history, complaint data, and payment data.

The additional data 606 may also include data describing health-related online activity of the user population 110, such as data describing search queries related to health conditions (e.g., search queries for "urination," "high blood sugar," "diabetes," "thirsty," names of glucose monitoring systems, and so on), data describing navigation to health- or diabetes-related websites, data describing interactions with health-related mobile applications, data describing social networking interactions with health-related profiles on one or more social networks (e.g., following users, hashtags, liking posts, commenting), data describing health-related social networking interactions (e.g., posts or comments) on one or more social networks, and so forth. In addition to these, the additional data 606 may describe any one or more of the aspects enumerated in the discussion of the additional data 410.

State information is generated for the user by processing the CGM packages and the additional data, in part, using one or more models (block 1906). By way of example, the engagement state model manager 602 generates state information 608 by processing the CGM packages 302 and the additional data 606 of the person 102 using engagement state models 604 (e.g., machine learning models). In accordance with the principles discussed herein, the state information includes at least a current state of the user with regards to the CGM system. The current state may correspond to a current role of the user in relation to the CGM platform, e.g., patient, caregiver, health care provider, customer service representative, third-party service provider, commercial user (e.g., athlete, life hacker, etc.), performance coach, and so forth. Alternately or additionally, the current state may correspond to a current stage of a plurality of stages of interaction with the CGM system. In the context of a patient, such stages of interaction may include, an inquiry stage (e.g., where a user inquires about or otherwise demonstrates interest in the CGM system or inquires about medical conditions related to diabetes), a selection stage (e.g., where the user is actively selecting among glucose monitoring solutions), a prescribed stage, an active use stage (e.g., where the user actively uses the CGM system along with functionality of the CGM platform), an erratic use stage (e.g., where a user's activity level declines some amount from a previous active use level and/or drops below a threshold amount of use), a discontinued use stage (e.g., where the user discontinues use of the CGM system and/or the CGM platform), a subsequent solution stage (e.g., where the user uses a different CGM system deployed by an entity that is different from the CGM platform), and so on.

As discussed throughout, the state information may also include one or more transition probabilities 1504 and driving factors 1506. The transition probability 1504 may represent a probability of the person 102 to transition from a current state to a new state, e.g., the discontinued use state. In one or more implementations, the state information 608 may include transition probabilities for each of a plurality of possible states. The driving factors 1506 may indicate which factors likely drive a transition from the current state to the new state. In the implementation where the transition probability 1504 corresponds to a probability the person 102 will transition to a discontinued use stage, the driving factors 1506 indicate the factors that are likely driving the person to transition to the discontinued use stage.

Communication with the user is controlled based on the state information (block 1908). By way of example, the state information 608 can be used to control communication with users of the CGM platform 112. Based on determining which state corresponds to a user and/or detecting transitions between states, the multi-state engagement system 318 can generate notifications indicative of the states and/or state changes, and communicate the notifications to a predetermined recipient, e.g., to a patient, to a health care provider, to a customer service representative for intervention, and so forth. In some cases, the communication with the user is controlled by generating intervention strategies to prevent users from transitioning to a negative state such as discontinuing use of the CGM system.

FIG. 20 depicts an example procedure 2000 in which intervention strategies are generated to prevent users from transitioning to a negative state.

CGM packages and additional data of a user population of users of a CGM system is maintained in a storage device (block 2002). By way of example, storage device 120 maintains CGM packages 302 and additional data 606 of user population 110.

State information is generated for users of the user population by processing at least a portion of the CGM packages and the additional data using one or more models (block 2004). By way of example, the engagement state model manager 602 generates state information 608 by processing the CGM packages 302 and the additional data 606 using engagement state models 604 (e.g., machine learning models). In accordance with the principles discussed herein, the state information 608 may include transition probabilities 1504 that respective users of the user population will transition from a current state to a negative state and driving factors 1506 that are likely to drive the transition of the respective users from the current state to the negative state.

Users of the user population that are likely to transition to the negative state are identified based on the transition probabilities (block 2006). By way of example, based on the transition probabilities and the driving factors, the intervention platform 802 can identify users of the user population 110 that are likely to transition to the negative state (e.g., a discontinued use stage) based on the transition probability of the identified users being above a predetermined threshold.

Intervention strategies are generated to prevent the users from transitioning to the negative state based on the transition probabilities and the driving factors (block 2008). By way of example, the intervention platform 802 generates various intervention strategies to prevent the users from transitioning to the negative state based on the transition probabilities 1504 and the driving factors 1506. Such intervention strategies may include exposing the state information to a user that is authorized to intervene in certain scenarios by communicating with users, e.g., a customer service representative, clinician, and so forth. The intervention platform 802 may provide the state information (or notifications derived based on the state information) through an intervention portal, e.g., where a customer service representative can review state information for multiple users. The exposed state information may enable an authorized user of the intervention platform to determine whether to communicate with a user associated with the state information or not, such as whether to initiate a telephone call to the user, send an email to the user, send an SMS message to the user and so forth. Alternately or additionally, the intervention platform 802 may be configured to automatically generate and communicate the communication based on the state information, such as according to logic that instructs the intervention platform to communicate in particular ways depending on the state information.

Regardless of whether the intervention strategy includes exposing transition information to a human or is automated, the intervention platform can customize the intervention strategy based on the determined factors driving the predicted transition from the current state to the new state. By way of example, if the state information indicates that faulty equipment (e.g., a faulty sensor) is being used and an amount of use has dropped since beginning use of the faulty equipment, a customer service representative may deploy a strategy specific to replacing the faulty equipment, e.g., sending new, properly working equipment. As another example, if the state information indicates abnormally high blood glucose readings is causing user frustration which will likely lead to discontinued use, then the intervention system may communicate a message to the user that includes success stories of other users in the population who have reduced their blood glucose levels while wearing the CGM system through diet and exercise.

Figure 21:
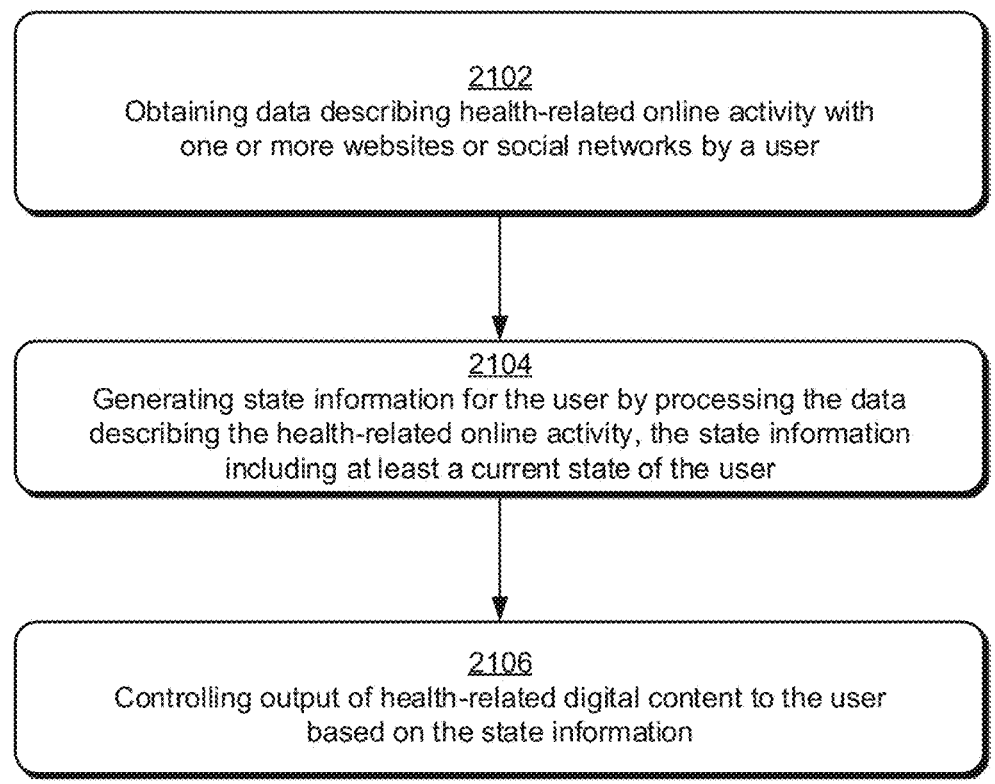
FIG. 21 depicts a procedure in an example implementation in which the output of health-related digital content is controlled based on state information determined from health-related online activity.

FIG. 21 depicts an example procedure 2100 in which the output of health-related digital content is controlled based on state information determined from health-related online activity.

Data describing health-related online activity with one or more websites or social network platforms is obtained (block 2100). By way of example, the CGM platform 112 obtains additional data 606 which may include data describing health-related online activity, such as data describing search queries related to health conditions (e.g., search queries for "urination," "high blood sugar," "diabetes," "thirsty," names of glucose monitoring systems, and so on), data describing navigation to health- or diabetes-related websites, data describing interactions with health-related mobile applications, data describing social networking interactions with health-related profiles on one or more social networks (e.g., following users, hashtags, liking posts, commenting), data describing health-related social networking interactions (e.g., posts or comments) on one or more social networks, and so forth.

The data describing the health-related online activity may be received in a variety of different ways. For example, as depicted in FIG. 16, search queries related to health conditions can be received via a search query input element 1604 implemented in a user interface 1602. The user interface 1602 may be implemented at one or more websites (e.g., a search engine website), within a social network, and the like. It is to be appreciated that although the search query input element 1604 is illustrated as a text entry field, a search query may be received in a variety of ways without departing from the spirit or scope of the described techniques, such by receiving a voice command via a voice assistant device.

In accordance with the described techniques, a particular search query may be referred to as a health-related, or more specifically, a diabetes-related search query. Other examples of diabetes-related search queries may include "urination," "headaches," "veins," and "diabetes," to name just a few. Indeed, health- and diabetes-related search queries may include a variety of terms and combinations of those terms, including terms related to nutrition and exercise. In any case, receipt of such search queries may be captured by tracking a user's online activity, and data may be generated describing the receipt of these search queries.

State information for the user is generated by processing the data describing health-related online activity (block 2104). In accordance with the principles discussed herein, the state information includes at least a current state of the user. By way of example, searching for health- and diabetes-related information may correspond to an inquiry or selection stage of engagement in relation to the CGM system 104, such that the engagement state models 604 predict that a user submitting such search queries corresponds to at least one of those stages.

The output of health-related digital content to the user is controlled based on the state information (block 2106). By way of example, the CGM platform can control the output of health-related digital content, such as via the digital content component 1610 which is shown as being displayed in the user interface 1602 in response to receiving the search query 1606. The digital content component 1610 may correspond to a digital advertisement displayed via the user interface 1602, a search result displayed via the user interface 1602, a pop-up or toast notification displayed via the user interface 1602, and so on. Certainly, the digital content component 1610 may be configured in a variety of ways without departing from the spirit or scope of the techniques, such as audible information output via a voice assistant device, mobile notifications (e.g., via a mobile phone or smart watch), information presented via one or more social networks, an SMS message, and so forth. Alternately or additionally, the CGM platform 112 may initiate other types of communication with the user based on the health- and diabetes-related search queries, such as by sending mail to the user, calling the user, and so forth. Other types of communication may include communicating with a caregiver of the user (e.g., parent or guardian), or a medical professional associated with the user, to name just a few.

The digital content component 1610 may provide support so that the user can monitor glucose and prevent or mitigate dangerous health conditions, such as by providing further information about health conditions that arise due to diabetes, how to contact medical providers, how to contact customer support representatives of the CGM platform 112, information about the ease of using the CGM system 104, information about the CGM system 104, information about other persons with diabetes and their lives, and so forth. Indeed, the digital content component 1610 may include a variety of information without departing from the spirit or scope of the described techniques.

It is further to be appreciated that these techniques may also be deployed to communicate with potential "commercial" users of the CGM system 104 and the CGM platform 112, such as when users enter search queries like "tracking blood sugar," "how does blood sugar affect performance," "blood glucose athletic performance," "blood glucose and mental performance," and so forth. Such users may also be determined, using the engagement state models 604, to be in a state that captures their stage as being in an inquiry stage or selection stage, but with a "commercial" user role rather than a "patient" role.

The output of the health-related digital content may be controlled, in part, by customizing the health-related digital content based on the current state of the user. In other words, the system can customize, select, or generate health-related digital content that includes information that is pertinent to the user's current role and stage of engagement with the CGM system. For example, if the system determines that a user is in an inquiry stage or selection stage in a commercial user role, then the CGM platform may customize the health-related digital content to include information pertaining to using the CGM system to improve user health. In contrast, if system determines that the user is in an inquiry stage or a selection stage, but also that the user likely has pre-diabetes based on the user's health related search queries, then the system may customize the health-related digital content to include further information about health conditions that arise due to diabetes, how to contact medical providers, and so forth. Thus the information included in the health-related digital content, as well as the delivery method, can vary dynamically to account for different states of users.

Having described example procedures in accordance with one or more implementations, consider now an example system and device that can be utilized to implement the various techniques described herein.

Example System and Device

Figure 22:
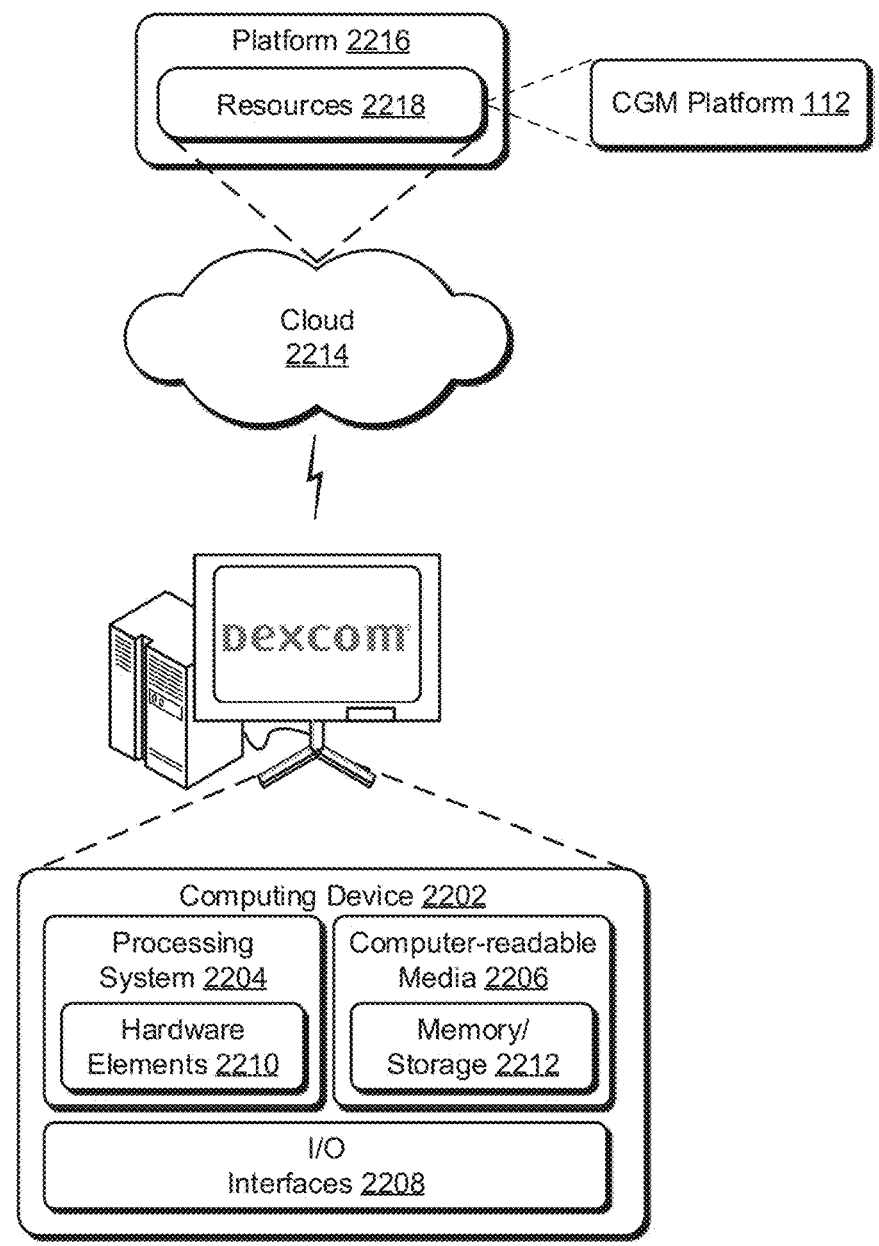
FIG. 22 illustrates an example system including various components of an example device that can be implemented as any type of computing device as described and/or utilized with reference to FIGS. 1-21 to implement embodiments of the techniques described herein.

FIG. 22 illustrates an example system generally at 2200 that includes an example computing device 2202 that is representative of one or more computing systems and/or devices that may implement the various techniques described herein. This is illustrated through inclusion of the CGM platform 112. The computing device 2202 may be, for example, a server of a service provider, a device associated with a client (e.g., a client device), an on-chip system, and/or any other suitable computing device or computing system.

The example computing device 2202 as illustrated includes a processing system 2204, one or more computer-readable media 2206, and one or more I/O interfaces 2208 that are communicatively coupled, one to another. Although not shown, the computing device 2202 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 2204 is representative of functionality to perform one or more operations using hardware. Accordingly, the processing system 2204 is illustrated as including hardware elements 2210 that may be configured as processors, functional blocks, and so forth. This may include implementation in hardware as an application specific integrated circuit or other logic device formed using one or more semiconductors. The hardware elements 2210 are not limited by the materials from which they are formed or the processing mechanisms employed therein. For example, processors may be comprised of semiconductor(s) and/or transistors (e.g., electronic integrated circuits (ICs)). In such a context, processor-executable instructions may be electronically-executable instructions.

The computer-readable media 2206 is illustrated as including memory/storage 2212. The memory/storage 2212 represents memory/storage capacity associated with one or more computer-readable media. The memory/storage component 2212 may include volatile media (such as random access memory (RAM)) and/or nonvolatile media (such as read only memory (ROM), Flash memory, optical disks, magnetic disks, and so forth). The memory/storage component 2212 may include fixed media (e.g., RAM, ROM, a fixed hard drive, and so on) as well as removable media (e.g., Flash memory, a removable hard drive, an optical disc, and so forth). The computer-readable media 2206 may be configured in a variety of other ways as further described below.

Input/output interface(s) 2208 are representative of functionality to allow a user to enter commands and information to computing device 2202, and also allow information to be presented to the user and/or other components or devices using various input/output devices. Examples of input devices include a keyboard, a cursor control device (e.g., a mouse), a microphone, a scanner, touch functionality (e.g., capacitive or other sensors that are configured to detect physical touch), a camera (e.g., which may employ visible or non-visible wavelengths such as infrared frequencies to recognize movement as gestures that do not involve touch), and so forth. Examples of output devices include a display device (e.g., a monitor or projector), speakers, a printer, a network card, tactile-response device, and so forth. Thus, the computing device 2202 may be configured in a variety of ways as further described below to support user interaction.

Various techniques may be described herein in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. The features of the techniques described herein are platform-independent, meaning that the techniques may be implemented on a variety of commercial computing platforms having a variety of processors.

An implementation of the described modules and techniques may be stored on or transmitted across some form of computer-readable media. The computer-readable media may include a variety of media that may be accessed by the computing device 2202. By way of example, and not limitation, computer-readable media may include "computer-readable storage media" and "computer-readable signal media."

"Computer-readable storage media" may refer to media and/or devices that enable persistent and/or non-transitory storage of information in contrast to mere signal transmission, carrier waves, or signals per se. Thus, computer-readable storage media refers to non-signal bearing media. The computer-readable storage media includes hardware such as volatile and non-volatile, removable and non-removable media and/or storage devices implemented in a method or technology suitable for storage of information such as computer readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable signal media" may refer to a signal-bearing medium that is configured to transmit instructions to the hardware of the computing device 2202, such as via a network. Signal media typically may embody computer readable instructions, data structures, program modules, or other data in a modulated data signal, such as carrier waves, data signals, or other transport mechanism. Signal media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media.

As previously described, hardware elements 2210 and computer-readable media 2206 are representative of modules, programmable device logic and/or fixed device logic implemented in a hardware form that may be employed in some embodiments to implement at least some aspects of the techniques described herein, such as to perform one or more instructions. Hardware may include components of an integrated circuit or on-chip system, an application-specific integrated circuit (ASIC), a field-programmable gate array (FPGA), a complex programmable logic device (CPLD), and other implementations in silicon or other hardware. In this context, hardware may operate as a processing device that performs program tasks defined by instructions and/or logic embodied by the hardware as well as a hardware utilized to store instructions for execution, e.g., the computer-readable storage media described previously.

Combinations of the foregoing may also be employed to implement various techniques described herein. Accordingly, software, hardware, or executable modules may be implemented as one or more instructions and/or logic embodied on some form of computer-readable storage media and/or by one or more hardware elements 2210. The computing device 2202 may be configured to implement particular instructions and/or functions corresponding to the software and/or hardware modules. Accordingly, implementation of a module that is executable by the computing device 2202 as software may be achieved at least partially in hardware, e.g., through use of computer-readable storage media and/or hardware elements 2210 of the processing system 2204. The instructions and/or functions may be executable/operable by one or more articles of manufacture (for example, one or more computing devices 2202 and/or processing systems 2204) to implement techniques, modules, and examples described herein.

The techniques described herein may be supported by various configurations of the computing device 2202 and are not limited to the specific examples of the techniques described herein. This functionality may also be implemented all or in part through use of a distributed system, such as over a "cloud" 2214 via a platform 2216 as described below.

The cloud 2214 includes and/or is representative of a platform 2216 for resources 2218. The platform 2216 abstracts underlying functionality of hardware (e.g., servers) and software resources of the cloud 2214. The resources 2218 may include applications and/or data that can be utilized while computer processing is executed on servers that are remote from the computing device 2202. Resources 2218 can also include services provided over the Internet and/or through a subscriber network, such as a cellular or Wi-Fi network.

The platform 2216 may abstract resources and functions to connect the computing device 2202 with other computing devices. The platform 2216 may also serve to abstract scaling of resources to provide a corresponding level of scale to encountered demand for the resources 2218 that are implemented via the platform 2216. Accordingly, in an interconnected device embodiment, implementation of functionality described herein may be distributed throughout the system 2200. For example, the functionality may be implemented in part on the computing device 2202 as well as via the platform 2216 that abstracts the functionality of the cloud 2214.

CONCLUSION

Although the systems and techniques have been described in language specific to structural features and/or methodological acts, it is to be understood that the systems and techniques defined in the appended claims are not necessarily limited to the specific features or acts described. Rather, the specific features and acts are disclosed as example forms of implementing the claimed subject matter.

What is claimed is:

1. A method comprising:
at each computing device of a plurality of computing devices coupled to a network:
receiving glucose values from a continuous glucose monitoring (CGM) system worn by a user,
forming CGM packages based, at least in part, on the glucose values, and
transmitting the CGM packages to a storage device over the network;
at a data analytics server coupled to the network:
generating state information for the users by processing at least a portion of the CGM packages and additional user data stored on the storage device using one or more models, the state information including current states and transition probabilities that the users will transition from a current state to a new state and driving factors that are likely to drive the transition, each state describing a state of engagement of the user with the CGM system, the new state comprising a negative state; and
at an intervention server coupled to the network:
receiving the state information from the data analytics server over the network,
identifying users that are likely to transition to the negative state based on the transition probabilities; and
generating intervention strategies to prevent the identified users from transitioning to the negative state based on the transition probabilities and the driving factors, the generating including transmitting, over the network, a notification or message to the computing device of each identified user to prevent the transition of the identified user to the negative state.

2. The method as described in claim 1, wherein the negative state comprises a discontinued use state.

3. The method as described in claim 1, wherein the identifying comprises identifying users that are likely to transition as users having a transition probability above a threshold.

4. The method as described in claim 1, further comprising initiating, at the intervention server, communication of the driving factors to a recipient associated with each identified user as part of an intervention strategy.

5. The method as described in claim 1, further comprising initiating, at the intervention server, communication of one or more messages to a recipient associated with each identified user to prevent the transition to the negative state as part of the intervention strategy.

6. The method as described in claim 5, further comprising automatically customizing, at the intervention server, the one or more messages based on the driving factors.

7. The method as described in claim 1, wherein the one or more models are generated based on at least a portion of historical CGM packages and historical additional data of the users using one or more machine learning techniques.

8. A system comprising:
a plurality of continuous glucose monitoring (CGM) systems, each CGM system worn by a user, and each CGM system configured to measure glucose values of the user;
a plurality of computing devices, each computing device coupled to a network, and each computing device configured to:
receive, from one of the CGM systems, the measured glucose values,
form CGM packages based, at least in part, on the glucose values, and
transmit, over the network, the CGM packages to a storage device;
a data analytics server, coupled to the network, configured to generate state information for the users by processing at least a portion of the CGM packages and additional user data using one or more models, the state information including current states and transition probabilities that the users will transition from a current state to a new state and driving factors that are likely to drive the transition, each state describing a state of engagement of the user with the CGM system, the new state comprising a negative state; and
an intervention server, coupled to the network, configured to:
receive, over the network, the state information from the data analytics server,
identify users that are likely to transition to the negative state based on the transition probabilities, and
generate intervention strategies to prevent the identified users from transitioning to the negative state based on the transition probabilities and the driving factors, including transmit, over the network, a notification or message to the computing device of each identified user to prevent the transition of the identified user to the negative state.

9. The system as described in claim 8, wherein the negative state comprises a discontinued use state.

10. The system as described in claim 8, wherein the intervention server identifies users that are likely to transition as users having a transition probability above a threshold.

11. The system as described in claim 8, wherein an intervention strategy includes the intervention server initiating communication of the driving factors to a recipient associated with the each identified user.

12. The system as described in claim 8, wherein an intervention strategy includes the intervention server initiating communication of one or more messages to each identified user to prevent the transition to the negative state.

13. The system as described in claim 12, wherein the intervention server automatically customizes the one or more messages based on the driving factors.

14. The system as described in claim 8, wherein the one or more models are generated based on at least a portion of historical CGM packages and historical additional data of the users using one or more machine learning techniques.

15. A system, comprising:
a plurality of computing devices, each computing device configured to:
receive glucose values from a continuous glucose monitoring (CGM) system worn by a user,
form CGM packages based, at least in part, on the glucose values, and
transmit, over a network, the CGM packages to a storage device;
a data analytics server, coupled to the network, configured to:
process the CGM packages and additional user data stored on the storage device to generate state information for each user, the state information including a current state and transition probabilities that the user will transition from a current state to a new state, each state describing a state of engagement of the user with the CGM system, the new state comprising a negative state; and an intervention server, coupled to the network, configured to:
receive, over the network, the state information from the data analytics server,
identify users that are likely to transition to the negative state based on the transition probabilities, and
transmit, over the network, a notification or message to the computing device of each identified user to prevent the transition of the identified user to the negative state.

16. The system as described in claim 15, wherein the negative state includes a discontinued use state.

17. The system as described in claim 15, wherein the new state comprises an erratic use state, and the intervention server is further configured to:
identify users that are likely to transition to the erratic use state based on the transition probabilities received from the data analytics server over the network; and
transmit, to the computing device of each identified user over the network, a notification or message to indicate a possible transition of the identified user to the erratic use state.

18. The system as described in claim 17, wherein the states further comprise an inquiry state, a selection state, a prescribed state, an active use state, and a subsequent solution state.

19. The system as described in claim 15, wherein the intervention server identifies users that are likely to transition as users having a transition probability above a threshold.

20. The method as described in claim 1, wherein the new state comprises an erratic use state, and the method further comprises:
at the intervention server:
identifying users that are likely to transition to the erratic use state based on the transition probabilities received from the data analytics server over the network; and
transmitting, over the network, a notification or message to the computing device of each identified user to indicate a possible transition of the identified user to the erratic use state.

21. The method as described in claim 20, wherein the states further comprise an inquiry state, a selection state, a prescribed state, an active use state, and a subsequent solution state.

22. The system as described in claim 9, wherein the new state comprises an erratic use state, and the intervention server is further configured to:
identify users that are likely to transition to the erratic use state based on the transition probabilities received from the network data analytics server over the network; and
transmit, over the network, a notification or message to the computing device of each identified user to indicate a possible transition of the identified user to the erratic use state.

23. The system as described in claim 22, wherein the states further comprise an inquiry state, a selection state, a prescribed state, an active use state, and a subsequent solution state.

24. A system comprising:
a data analytics server, coupled to a network, configured to:
retrieve, from a storage device over a network, continuous glucose monitoring (CGM) packages, each CGM package including measured glucose values from a CGM system worn by a user, and
generate, based on the CGM packages and additional user data, state information for each user, the state information including current states and transition probabilities that each user will transition from a current state to a new state, each state describing a state of engagement of the user with the CGM system, the new state comprising a negative state; and
an intervention server, coupled to the network, configured to:
receive, from the data analytics server over the network, the state information,
identify users that are likely to transition to the negative state based on the transition probabilities, and
transmit, over the network, a notification or message to a computing device of each identified user to prevent the transition of the identified user to the negative state.

* * * * *